(12) United States Patent
Marshall et al.

(10) Patent No.: US 11,633,264 B2
(45) Date of Patent: *Apr. 25, 2023

(54) DETERMINING AND TRACKING MOVEMENT

(71) Applicant: VisionX, LLC, Minneapolis, MN (US)

(72) Inventors: Michael C. Marshall, Edina, MN (US); Bruce Willard Hultgren, Victoria, MN (US); Timothy A. Miller, Inver Grove Heights, MN (US)

(73) Assignee: VOYAGER DENTAL, INC., Minneapolis, MN (US)

( * ) Notice: Subject to any disclaimer, the term of this patent is extended or adjusted under 35 U.S.C. 154(b) by 464 days.

This patent is subject to a terminal disclaimer.

(21) Appl. No.: 16/742,623

(22) Filed: Jan. 14, 2020

(65) Prior Publication Data

US 2020/0146790 A1 May 14, 2020

Related U.S. Application Data

(63) and a continuation-in-part of application No. 15/582,275, filed on Apr. 28, 2017, now Pat. No. 10,561,482.

(60) Provisional application No. 62/904,040, filed on Sep. 23, 2019.

(51) Int. Cl.
*A61C 9/00* (2006.01)
*A61C 11/00* (2006.01)
*A61C 19/045* (2006.01)

(52) U.S. Cl.
CPC ............ *A61C 9/0053* (2013.01); *A61C 11/00* (2013.01); *A61C 19/045* (2013.01)

(58) Field of Classification Search
CPC ...... A61C 9/0053; A61C 11/00; A61C 19/045
USPC .......................................................... 433/69
See application file for complete search history.

(56) References Cited

U.S. PATENT DOCUMENTS

| 4,306,861 | A | * | 12/1981 | Dickson | ................ | A61C 19/04 |
| | | | | | | 433/69 |
| 4,495,952 | A | * | 1/1985 | Klett | .................... | A61B 5/1114 |
| | | | | | | 33/791 |
| 4,859,181 | A | * | 8/1989 | Neumeyer | ............ | A61B 5/1114 |
| | | | | | | 433/69 |

(Continued)

FOREIGN PATENT DOCUMENTS

WO 2016196335 A1 12/2016

*Primary Examiner* — Matthew M Nelson
(74) *Attorney, Agent, or Firm* — Barnes & Thornburg LLP

(57) ABSTRACT

Apparatuses, components, devices, methods, and systems for determining and tracking movement are provided. An example apparatus that includes a position indicating system having a first light emitter positioned and oriented to emit light in a first direction, a second light emitter positioned and oriented to emit light in a second direction, the second direction being collinear with and opposite to the first direction; and a third light emitter positioned and oriented to emit light in a third direction, the third direction being different than the first direction and the second direction. The third direction may be offset from the first direction by an offset angle that is an acute angle. The apparatus may also include a screen; an imaging system configured to capture an image of the screen. The first light emitter and the third light emitter may both be configured to emit light toward the screen.

16 Claims, 29 Drawing Sheets

(56) References Cited

U.S. PATENT DOCUMENTS

| | | | | |
|---|---|---|---|---|
| 5,143,086 A * | 9/1992 | Duret | ............... | A61C 19/045 |
| | | | | 433/69 |
| 5,722,828 A * | 3/1998 | Halstrom | ............ | A61C 19/045 |
| | | | | 433/69 |
| 6,120,290 A * | 9/2000 | Fukushima | ............ | A61C 11/00 |
| | | | | 433/64 |
| 8,348,667 B2 | 1/2013 | Evenson | | |
| 8,556,626 B2 * | 10/2013 | Evenson | ............ | A61C 9/0006 |
| | | | | 433/68 |
| 8,794,962 B2 * | 8/2014 | Lauren | ............... | A61C 11/00 |
| | | | | 433/68 |
| 8,834,157 B2 | 9/2014 | Evenson et al. | | |
| 2012/0258431 A1 * | 10/2012 | Lauren | ............... | A61B 5/4542 |
| | | | | 600/595 |
| 2015/0072314 A1 | 3/2015 | Evenson et al. | | |

* cited by examiner

DETERMINING AND TRACKING MOVEMENT

CROSS REFERENCE TO RELATED APPLICATIONS

This application claims priority, as appropriate, to U.S. Ser. No. 62/328,837, titled "DETERMINING JAW MOVEMENT" and filed Apr. 28, 2016, U.S. Ser. No. 15/582,275, titled "DETERMINING JAW MOVEMENT" and filed Apr. 28, 2017, and U.S. Ser. No. 62/904,040, titled "DETERMINING JAW AND FACIAL MOVEMENT" and filed Sep. 23, 2019, the disclosures of which are hereby incorporated by reference in their entirety.

BACKGROUND

Understanding and recording an accurate static relationship between teeth in a patient's upper jaw and lower jaw is an important first step in the art and science of designing dental appliances or restorations and planning dental or surgical interventions that affect dental/skeletal function and aesthetics of the facial musculature system.

Additionally, the dynamic motion of the lower jaw and dentition interacting functionally and aesthetically is even more important in the various reconstructive domains in dentistry and medicine that require precise knowledge and locations of the musculoskeletal-dental components that define this motion. The greater accuracy of motion definition allows for more precise design of restorations (e.g., crowns, implants, full/partial prosthesis) and associated macro procedures such as orthognathic surgery, trauma reconstruction, etc. These physical components can be described in engineering terms as a kinematic linkage system incorporating the relationship of the temporomandibular joint to the dentition and soft tissue of the face. This linkage definition has only been approximated poorly by traditional articulator devices and systems in dentistry.

Dental appliances may be used in the treatment of various dental conditions. Examples of dental appliances include therapeutic appliances and restorative appliances (dental restorations). Non-limiting examples of therapeutic appliances include surgical splints, occlusal splints, orthodontic retainers, and orthodontic aligners. A dental restoration is a type of dental appliance that is used to restore a tooth or multiple teeth. For example, a crown is a dental restoration that is used to restore a single tooth. A bridge is another example of a dental restoration. A bridge may be used to restore one or more teeth. A denture is another example of a dental restoration. A denture can be a full or partial denture. Dentures can also be fixed or removable. An implant is yet another example of a dental restoration. Dental implants are prosthetic devices that are placed in bone tissue of a patient's jaw and used to secure other dental restorations such as implant abutments and crowns, or partial and full dentures. In some circumstances, dental restorations are used to restore functionality after a tooth is damaged. In other circumstances, dental restorations are used to aesthetically improve a patient's dentition.

When complex or multiple dental appliances, dental restorations, or dental therapies are applied to a patient simultaneously, errors or inaccuracies in the representation of dental motion are compounded, resulting in inadequate or suboptimal results for patients. In the worst case, inaccurate motion data can result in the complete failure of the appliances, restorations, or treatment at very high cost clinically, financially, and emotionally.

SUMMARY

In general terms, this disclosure is directed to a system for measuring jaw movement. In one possible configuration and by non-limiting example, a patient assembly is coupled to a patient's dentition and an imaging system captures images of the patient assembly as the patient's dentition moves.

One aspect is an apparatus comprising: a screen; an imaging system configured to capture an image of the screen; and a position indicating system that includes: a housing; a first light emitter disposed within the housing and oriented to emit light in a first direction toward the screen; a second light emitter disposed within the housing and oriented to emit light in a second direction, the second direction being collinear with and opposite to the first direction; and a third light emitter disposed within the housing and oriented to emit light in a third direction, the third direction being different than the first direction and the second direction; wherein the screen is disposed between the position indicating system and the imaging system.

Another aspect is an apparatus comprising: a screen assembly including a first planar screen and a second planar screen; an imaging system including a first camera configured to capture images of the first screen and a second camera configured to capture images of the second screen; a position indicating system including: a first light emitter positioned and oriented to emit light in a first direction toward the first screen; a second light emitter positioned and oriented to emit light in a second direction toward the second screen, the second direction being collinear with and opposite to the first direction; and a third light emitter positioned and oriented to emit light in a third direction toward the first screen, the third direction being different than the first direction and the second direction.

One other aspect is an apparatus configured to be worn on a dentition of a patient, the apparatus comprising: a dentition coupling device configured to couple to the dentition of the patient, the dentition coupling device including an extension member configured to protrude out from the patient's mouth; and a position indicating system rigidly connected to the dentition coupling device, the position indicating system including: a housing configured to rigidly connect to the extension member of the dentition coupling device; a first light emitter disposed within the housing and oriented to emit light in a first direction; a second light emitter disposed within the housing and oriented to emit light in a second direction, the second direction being collinear with and opposite to the first direction; and a third light emitter disposed within the housing and oriented to emit light in a third direction, the third direction being different than the first direction and the second direction and offset from the first direction by an offset angle that is an acute angle. For example, the offset angle may be less than 45 degrees.

Examples are implemented as a computer process, a computing system, or as an article of manufacture such as a device, computer program product, or computer readable medium. According to an aspect, the computer program product is a computer storage medium readable by a computer system and encoding a computer program comprising instructions for executing a computer process.

The details of one or more aspects are set forth in the accompanying drawings and description below. Other features and advantages will be apparent from a reading of the following detailed description and a review of the associated drawings. It is to be understood that the following detailed description is explanatory only and is not restrictive of the claims.

DETAILED DESCRIPTION

Figure 1:
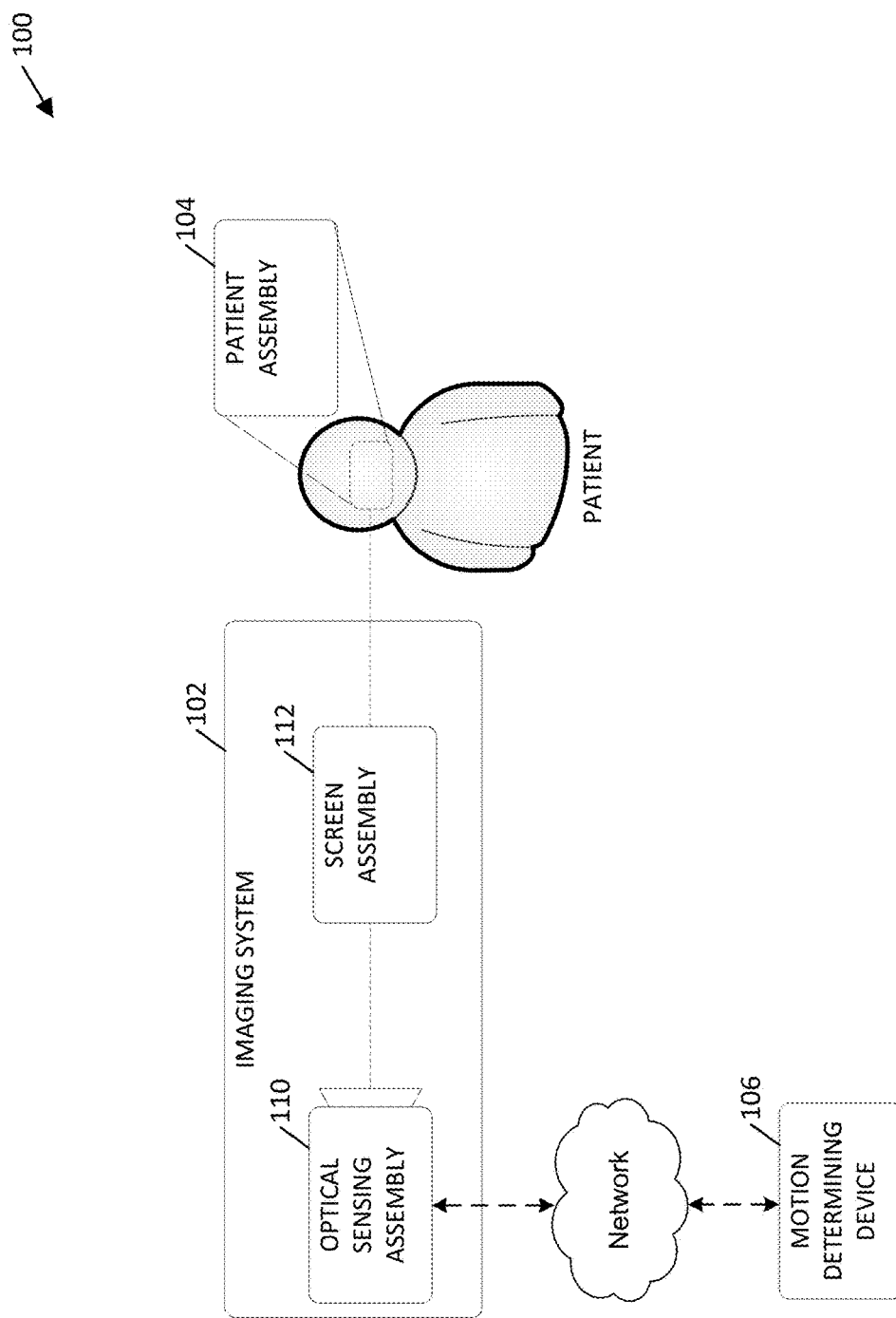
FIG. 1 is a schematic block diagram illustrating an example motion capture system for capturing jaw movement.

Various embodiments will be described in detail with reference to the drawings, wherein like reference numerals represent like parts and assemblies throughout the several views. Reference to various embodiments does not limit the scope of the claims attached hereto. Additionally, any examples set forth in this specification are not intended to be limiting and merely set forth some of the many possible embodiments for the appended claims.

The present disclosure relates to a jaw movement measurement system. For example, the system may record the motion of a patient's mandible relative to the patient's maxilla. In some embodiments, the system operates to infer the approximate location of a screw axis corresponding to the condyloid process of the temporomandibular joint of the patient. Further, the system may generate a model of a range of motion of the mandible relative to the maxilla based on the inferred location of the screw axis, the recorded motion, or both.

In embodiments, the recorded motion is applied to a three-dimensional digital model of at least a portion of the patient's dentition. This motion can then be used while designing dental appliances or planning various dental therapies for the patient. In this manner, the appliances and therapies can be designed based on analysis of a range of actual motion for the patient. This may be especially beneficial when designing complex restorations such as bridges, implants, or implant-supported prosthesis for the treatment of edentulous or partially edentulous dentitions as well as in providing dental therapies such as oral-maxillofacial reconstructive surgery.

FIG. 1 is a schematic block diagram illustrating an example motion capture system 100 for capturing jaw movement. In this example, the motion capture system 100 includes an imaging system 102, a patient assembly 104, and a motion determining device 106. Also shown in FIG. 1 are a patient and a network.

In some embodiments, the imaging system 102 includes an optical sensing assembly 110 and a screen assembly 112. The optical sensing assembly 110 may capture a plurality of images as the patient's jaw moves. For example, the optical sensing assembly 110 may include one or more cameras such as video cameras. In some embodiments, the optical sensing assembly 110 captures a plurality of images that do not necessarily include the patient assembly, but can be used to determine the position of the patient assembly 104. For example, the patient assembly 104 may emit lights that project onto surfaces of the screen assembly 112 and the optical sensing assembly 110 may capture images of those surfaces of the screen assembly 112. In some implementations, the optical sensing assembly 110 does not capture images but otherwise determines the position of the projected light or lights on the surfaces of the screen assembly 112.

The screen assembly 112 may include one or more screens. A screen may include any type of surface upon which light may be projected. Some implementations include flat screens that have a planar surface. Some implementations may include rounded screens, having cylindrical (or partially cylindrical) surfaces. The screens may be formed from a translucent material. For example, the locations of the lights projected on the screens of the screen assembly 112 may be visible from a side of the screens opposite the patient assembly 104 (e.g., the screen assembly 112 may be positioned between the optical sensing assembly 110 and the patient assembly 104).

In addition to capturing the images, the imaging system 102 may capture or generate various information about the images. As an example, the imaging system 102 can generate timing information about the images. Although alternatives are possible, the timing information can include a timestamp for each of the images. Alternatively or additionally, a frame rate (e.g., 10 frames/second, 24 frames/second, 60 frames/second) is stored with a group of images. Other types of information that can be generated for the images includes an identifier of a camera, a position of a camera, or settings used when capturing the image.

The patient assembly 104 is an assembly that is configured to be secured to the patient. The patient assembly 104 or parts thereof may be worn by the patient and may move freely with the patient (i.e., at least a part of the patient assembly 104 may, when mounted to the patient, move in concert with patient head movement). In contrast, in at least some implementations, the imaging system 102 is not mounted to the patient and does not move in concert with patient head movement.

In some embodiments, the patient assembly 104 may include light emitters that emit a pattern of light that projects on one or more surfaces (e.g., screens of the screen assembly 112), which can be imaged to determine the position of the patient assembly 104. For example, the light emitters may emit beams of substantially collimated light (e.g., laser beams) that project onto the surfaces as points. Based on the locations of these points on the surfaces, a coordinate system can be determined for the patient assembly 104, which can then be used to determine a position and orientation of the patient assembly 104 and the patient's dentition.

In some embodiments, the patient assembly 104 includes separate components that are configured to be worn on the upper dentition and the lower dentition and to move independently of each other so that the motion of the lower dentition relative to the upper dentition can be determined. Examples of the patient assembly 104 are illustrated and described throughout, including in FIG. 2.

The motion determining device 106 determines the motion of the patient assembly 104 based on images captured by the imaging system 102. In some embodiments, the motion determining device 106 includes a computing device that uses image processing techniques to determine three-dimensional coordinates of the patient assembly 104 (or portions of the patient assembly) as the patient's jaw is in different positions. For example, images captured by the optical sensing assembly 110 of screens of the screen assembly 112 may be processed to determine the positions on the screens at which light from the patient assembly is projected. These positions on the screens of the screen assembly 112 may be converted to three-dimensional coordinates with respect to the screen assembly 112. From those three-dimensional coordinates, one or more positions and orientations of the patient assembly 104 (or components of the patient assembly 104) may be determined.

Based on the determined positions and orientations of the patient assembly 104, some embodiments determine the relative positions and movements of the patient's upper and lower dentition. Further, some embodiments infer the location of a kinematically derived screw axis that is usable in modeling the motion of the patient's mandible (including the lower dentition) about the temporomandibular joint. Examples of the motion determining device 106 and operations it performs are illustrated and described throughout, including in FIGS. 16, 17, 28, and 29.

Figure 2:
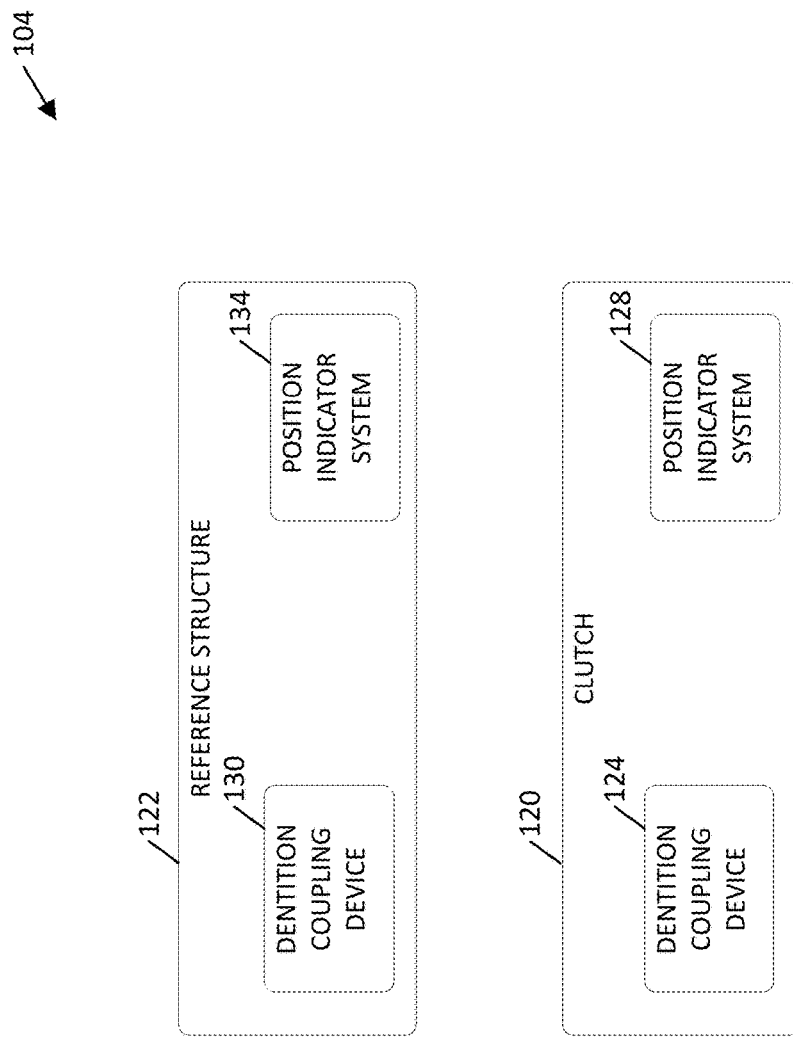
FIG. 2 illustrates a block diagram of an example patient assembly of FIG. 1.

FIG. 2 illustrates a block diagram of an example patient assembly 104. In this example, the patient assembly includes a clutch 120 and a reference structure 122. Here, the clutch 120 and the reference structure 122 are not physically connected and can move independently of one another.

The clutch 120 is a device that is configured to couple to a patient's dentition. For example, the clutch 120 may grip the teeth of the dentition of the patient. In some embodiments, the clutch 120 comprises a dentition coupling device 124 and a position indicator system 128. In some embodiments, the clutch 120 is configured to couple to the lower dentition of the patient so as to move with the patient's mandible. In other embodiments, the clutch 120 may be configured to couple to the patient's upper dentition so as to move with the patient's maxilla.

The dentition coupling device 124 is configured to removably couple to the patient's dentition. In some embodiments, the dentition coupling device 124 rigidly couples to the patient's dentition such that while coupled, the movement of the dentition coupling device 124 relative to the patient's dentition is minimized. Various embodiments include various coupling mechanisms.

For example, some embodiments couple to the patient's dentition using brackets that are adhered to the patient's teeth with a dental or orthodontic adhesive. As another example, some embodiments couple to the patient's dentition using an impression material. For example, some embodiments of the dentition coupling device 124 comprise an impression tray and an impression material such as polyvinyl siloxane. To couple the dentition coupling device 124 to the patient's dentition, the impression tray is filled with impression material and then placed over the patient's dentition. As the impression material hardens, the dentition coupling device 124 couples to the patient's dentition.

Alternatively, some embodiments comprise a dentition coupling device 124 that is custom designed for a patient based on a three-dimensional model of the patient's dentition. For example, the dentition coupling device 124 may be formed using a rapid fabrication machine. One example of a rapid fabrication machine is a three-dimensional printer, such as the PROJET® line of printers from 3D Systems, Inc. of Rock Hill, S.C. Another example of a rapid fabrication machine is a milling device, such as a computer numerically controlled (CNC) milling device. In these embodiments, the dentition coupling device 124 may comprise various mechanical retention devices such as clasps that are configured to fit in an undercut region of the patient's dentition.

Embodiments of the dentition coupling device 124 may be operable to couple to the patient's dentition using a combination of one or more mechanical retention structures, adhesives, and impression materials. For example, the dentition coupling device 124 may include apertures through which a fastening device such as a temporary anchorage device may be threaded to secure the dentition coupling device 124 to the patient's dentition. For example, the temporary anchorage devices may screw into the patient's bone tissue to secure the dentition coupling device 124. An example of a dentition coupling device that is secured using a temporary anchorage device is illustrated and described with respect to at least FIG. 6.

In some embodiments, the dentition coupling device 124 includes one or more fiducial markers, such as hemispherical inserts, that can be used to establish a static relationship between the position of the clutch 120 and the patient's dentition. For example, the dentition coupling device 124 may include three fiducial markers disposed along its surface. The location of these fiducial markers can then be determined relative to the patient's dentition such as by capturing a physical impression of the patient with the clutch attached or using imaging techniques such as capturing a digital impression (e.g., with an intraoral scanner) or other types of images of the dentition and fiducial markers. Some embodiments of the dentition coupling device 124 do not include fiducial markers. One or more images or a digital impression of the patient's dentition captured while the dentition coupling device 124 is mounted may be aligned to one or more images or a digital impression of the patient's dentition captured while the dentition coupling device 124 is not mounted.

The position indicator system 128 is a system that is configured to be used to determine the position and orientation of the clutch 120. In some embodiments, the position indicator system 128 includes multiple fiducial markers. In some examples, the fiducial markers are spheres. Spheres work well as fiducial markers because the location of the center of the sphere can be determined in an image regardless of the angle from which the image containing the sphere was captured. The multiple fiducial markers may be disposed (e.g., non-collinearly) so that by determining the locations of each (or at least three) of the fiducial markers, the position and orientation of the clutch 120 can be determined. For example, these fiducial markers may be used to determine the position of the position indicator system 128 relative to the dentition coupling device 124, through which the position of the position indicator system 128 relative to the patient's dentition can be determined.

Some implementations of the position indicator system 128 do not include separate fiducial markers. In at least some of these implementations, structural aspects of the position indicator system 128 may be used to determine the position and orientation of the position indicator system 128. For example, one or more flat surfaces, edges, or corners of the position indicator system 128 may be imaged to determine the position and orientation of the position indicator system 128. In some implementations, an intraoral scanner is used to capture a three-dimensional model (or image) that includes a corner of the position indicator system 128 and at least part of the patient's dentition while the dentition coupling device 124 is mounted. This three-dimensional model can then be used to determine a relationship between the position indicator system 128 and the patient's dentition. The determined relationship may be a static relationship that defines the position and orientation of the position indicator system 128 relative to a three-dimensional model of the patient's dentition (e.g., based on the corner of the position indicator system 128 that was captured by the intraoral scanner).

In some embodiments, the position indicator system 128 includes a light source assembly that emits beams of light. The light source assembly may emit substantially collimated light beams (e.g., laser beams). In some embodiments, the light source assembly is rigidly coupled to the dentition coupling device 124 so that as the dentition coupling device 124 moves with the patient's dentition, the beams of light move. The position of the dentition coupling device 124 is then determined by capturing images of where the light beams intersect with various surfaces (e.g., translucent screens disposed around the patient). Embodiments that include a light source assembly are illustrated and described throughout.

The reference structure 122 is a structure that is configured to be worn by the patient so as to provide a point of reference to measure the motion of the clutch 120. In embodiments where the clutch 120 is configured to couple to the patient's lower dentition, the reference structure 122 is configured to mount elsewhere on the patient's head so that the motion of the clutch 120 (and the patient's mandible) can be measured relative to the rest of the patient's head. For example, the reference structure 122 may be worn on the upper dentition. Beneficially, when the reference structure 122 is mounted securely to the patient's upper dentition, the position of the reference structure 122 will not be impacted by the movement of the mandible (e.g., muscle and skin movement associated with the mandibular motion will not affect the position of the reference structure 122). Alternatively, the reference structure 122 may be configured to be worn elsewhere on the patient's face or head.

In some embodiments, the reference structure 122 is similar to the clutch 120 but configured to be worn on the dental arch opposite the clutch (e.g., the upper dentition if the clutch 120 is for the lower dentition). For example, the reference structure 122 shown in FIG. 2 includes a dentition coupling device 130 that may be similar to the dentition coupling device 124, and a position indicator system 134 that may be similar to the position indicator system 128.

Figure 3:
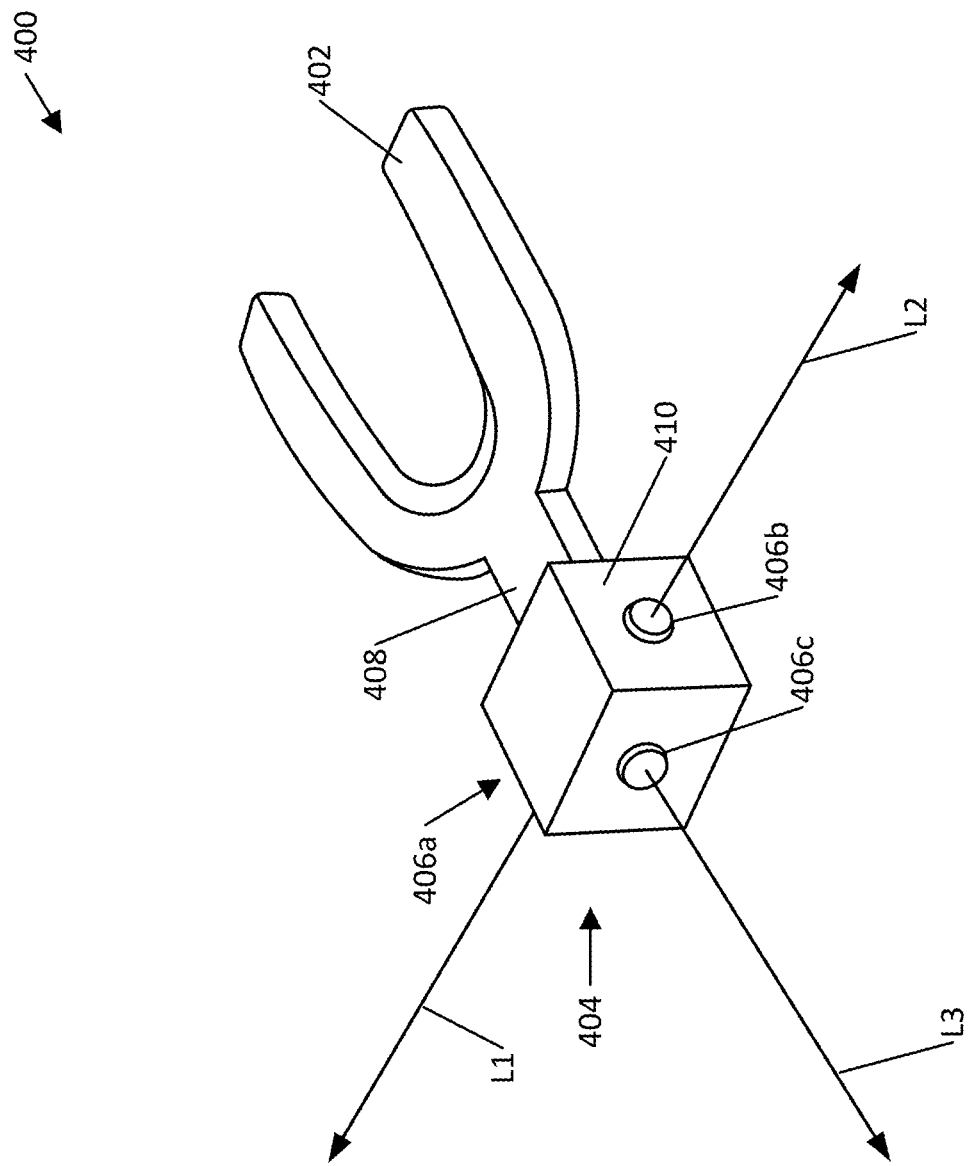
FIG. 3 illustrates an example embodiment of the clutch of FIG. 2.

FIG. 3 illustrates an embodiment of a clutch 400. The clutch 400 is an example of the clutch 120. In this example, the clutch 400 includes a dentition coupling device 402 and a light source assembly 404, and an extension member 408. The dentition coupling device 402 is an example of the dentition coupling device 124, and the light source assembly 404 is an example of the position indicator system 128.

The light source assembly 404, which may also be referred to as a projector, is a device that emits light beams comprising light that is substantially collimated. Collimated light travels in one direction. A laser beam is an example of collimated light. In some embodiments, the light source assembly 404 includes one or more lasers. Although alternatives are possible, the one or more lasers may be semiconductor lasers such as laser diodes or solid-state lasers such as diode-pumped solid-state lasers.

In some embodiments, the light source assembly 404 comprises a first, second, and third light emitter. The first and second light emitters may emit substantially collimated light in parallel but opposite directions (i.e., the first and second light emitters may emit light in antiparallel directions) such as to the left and right of the patient when the clutch 400 is coupled to the patient's dentition. In some embodiments, the first and second light emitters are collinear or are substantially collinear (e.g., offset by a small amount such as less than 5 micrometers, less than 10 micrometers, less than 25 micrometers, less than 50 micrometers, or less than 100 micrometers). The third light emitter may emit substantially collimated light in a direction of a line that intersects with or substantially intersects with lines corresponding to the direction of the first and second light emitters. Lines that intersect share a common point. Lines that substantially intersect do not necessarily share a common point, but would intersect if offset by a small amount such as less than 5 micrometers, less than 10 micrometers, less than 25 micrometers, less than 50 micrometers, or less than 100 micrometers. In some embodiments, the third light emitter emits light in a direction that is perpendicular to the first and second light emitters, such as toward the direction the patient is facing.

In some embodiments, the third light emitter emits light in a direction that is offset from the direction of the first light emitter so as to be directed toward the same side of the patient as the direction of the first light emitter. For example, the third light emitter may be offset from the first light emitter by an offset angle of less than 90 degrees such that the light emitted by both the first light emitter and the second light emitter intersect with the same screen (e.g., a planar screen having a rectangular shape and being disposed on a side of the patient). The third light emitter may be offset from the first light emitter by an offset angle. The offset angle may be an acute angle. For example, the offset angle may be between approximately 1 degree to 45 degrees. In some implementations, the offset angle is between 3 degrees and 30 degrees. In some implementations, the offset angle is between 5 degrees and 15 degrees. For example, the offset angle may be less than 10 degrees.

In some embodiments, one or more compensation factors are determined to compensate for an offset from the first and second light emitters being collinear, or an offset from the third light emitter emitting light in a direction of a line that intersects with the directions of the first and second light sources. A compensation factor may also be determined for the offset angle of the third light emitter with respect to the first and second light emitters. For example, an offset angle compensation factor may specify the angle between the direction of the third light emitter and a line defined by the first light emitter. In implementations in which the orientation of the third light emitter is directed perpendicular to or substantially perpendicular to the direction of the first light emitter, the offset angle compensation factor may be 90 degrees or approximately 90 degrees. In implementations in which the orientation of the third light emitter is directed toward a side of the patient, the offset angle compensation factor may, for example, be between approximately 5 and 45 degrees. The compensation factors may be determined specifically for each position indicator system manufactured to account for minor variation in manufacturing and assembly. The compensation factors may be stored in a datastore (such as on the motion determining device 106 or on a computer readable medium accessible by the motion determining device 106). Each position indicator system may be associated with a unique identifier that can be used to retrieve the associated compensation factor. The position indicator system 134 may include a label with the unique identifier or a barcode, QR code, etc. that specifies the unique identifier.

Some embodiments of the light source assembly 404 include a single light source and use one or more beam splitters such as prisms or reflectors such as mirrors to cause that light source to function as multiple light emitters by splitting the light emitted by that light source into multiple beams. In at least some embodiments, the emitted light emanates from a common point. As another example, some embodiments of the light source assembly 404 may comprise apertures or tubes through which light from a common source is directed. Some embodiments may include separate light sources for each of the light emitters.

In the example of FIG. 3, the light source assembly 404 includes light emitters 406a, 406b, and 406c (referred to collectively as light emitters 406) and a housing 410. The light emitter 406a is emitting a light beam L1, the light emitter 406b is emitting a light beam L2, and the light emitter 406c is emitting a light beam L3. The light beams L1 and L2 are parallel to each other, but directed in opposite directions. The light beam L3 is perpendicular to the light beams L1 and L2. In at least some embodiments, the housing 410 is configured to position the light emitters 406 so that the light beams L1, L2, and L3 are approximately co-planar with the occlusal plane of the patient's dentition. Although the light beam L3 is perpendicular to the light beams L1 and L2 in the example of FIG. 3, alternatives are illustrated and described with respect to at least FIGS. 22-28.

The housing 410 may be approximately cube shaped and includes apertures through which the light emitters 406 extend. In other embodiments, the light emitters do not extend through apertures in the housing 410 and instead light emitted by the light emitters 406 passes through apertures in the housing 410.

In the example of FIG. 3, the dentition coupling device 402 is rigidly coupled to the light source assembly 404 by an extension member 408. The extension member 408 extends from the dentition coupling device 402 and is configured to extend out of the patient's mouth when the dentition coupling device 402 is worn on the patient's dentition. In some embodiments, the extension member 408 is configured so as to be permanently attached to the light source assembly 404 such as by being formed integrally with the housing 410 or joined via welding or a permanent adhesive. In other embodiments, the extension member 408 is configured to removably attach to the light source assembly 404. Because the light source assembly 404 is rigidly coupled to the dentition coupling device 402, the position and orientation of the dentition coupling device 402 can be determined from the position and orientation of the light source assembly 404.

In some embodiments, the housing 410 and the dentition coupling device 402 are integral (e.g., are formed from a single material or are coupled together in a manner that is not configured to be separated by a user). In some embodiments, the housing 410 includes a coupling structure configured to removably couple to the extension member 408 of the dentition coupling device 402. In this manner, the dentition coupling device 402 can be a disposable component that may be custom fabricated for each patient, while the light source assembly 404 may be reused with multiple dentition coupling devices. In some embodiments, the housing 410 includes a connector that is configured to mate with a connector on the dentition coupling device 402. Additionally or alternatively, the housing 410 may couple to the dentition coupling device 402 with a magnetic clasp. Some embodiments include a registration structure that is configured to cause the housing 410 to join with the dentition coupling device 402 in a repeatable arrangement and orientation. In some embodiments, the registration structure comprises a plurality of pins and corresponding receivers. In an example, the registration structure includes a plurality of pins disposed on the housing 410 and corresponding receivers (e.g., holes) in the dentition coupling device 402 (or vice versa). In some embodiments, the registration structure comprises a plurality of spherical attachments and a plurality of grooves. In one example, the registration structure includes three or more spherical attachments disposed on the housing 410 and two or more v-shaped grooves disposed on the dentition coupling device 402 that are disposed such that the spherical attachments will only fit into the grooves when the housing 410 is in a specific orientation and position relative to the dentition coupling device 402. In some implementations, the registration structure includes a spring-mounted pin or screw that serves as a detent to impede movement of the housing 410 with respect to the dentition coupling device 402.

Figure 4:
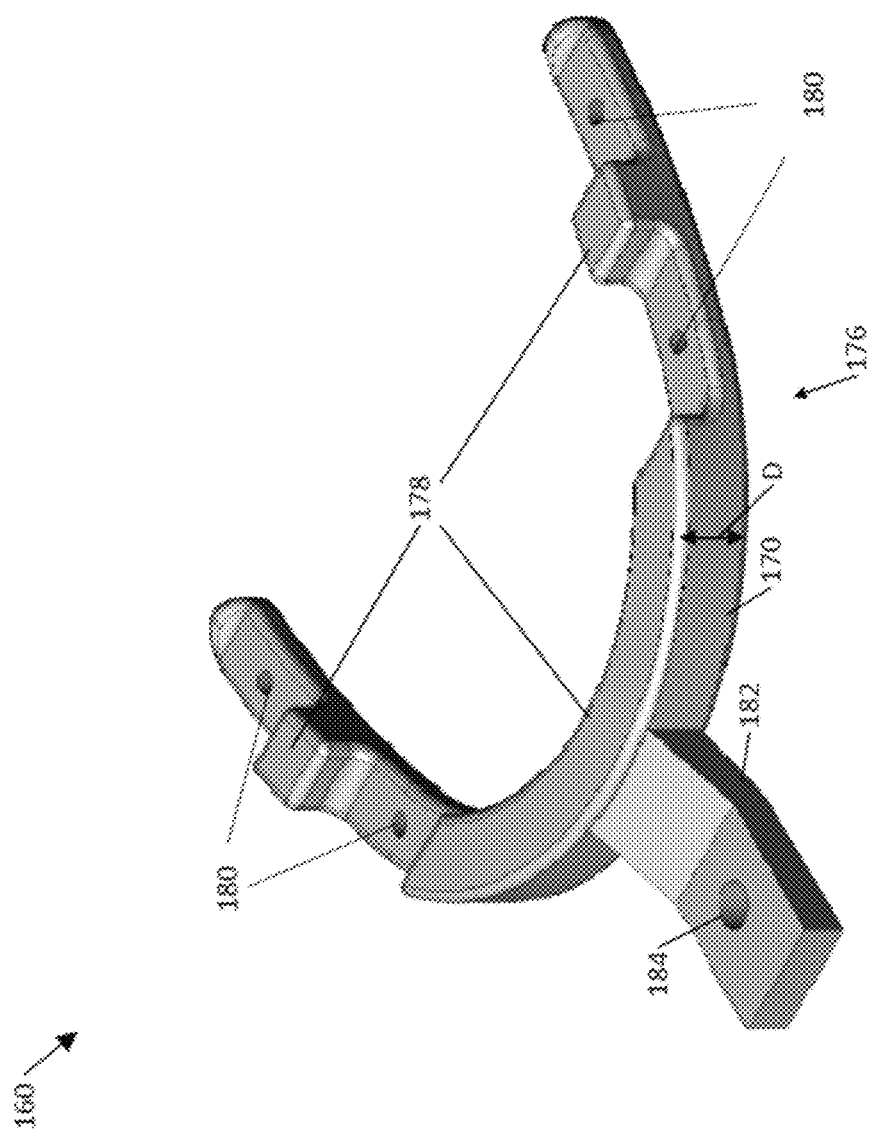
FIG. 4 illustrates an example embodiment of a dentition coupling framework of the clutch or reference structure of FIG. 2.

FIG. 4 illustrates an example embodiment of a dentition coupling framework 170 that can be included in a dentition coupling device 160. The dentition coupling device 160 is an example of the dentition coupling device 124 or the dentition coupling device 130. Some embodiments of a dentition coupling device also include an impression device 200 that is not shown in FIG. 4, but is illustrated and described with respect to at least FIG. 5.

The dentition coupling framework 170 includes a dentition facing surface 176, a contact surface 178, and an extension member 182. The dentition facing surface 176 is configured to align with the patient's dentition and face towards the occlusal surface of the patient's dentition. In this example, the dentition facing surface 176 is configured to hold an impression tray, which may be secured to the dentition coupling framework 170 using one or more fastening devices such as screws. In this example, the dentition facing surface 176 includes holes 180 that are configured for use with fastening devices to couple to an impression tray. In other embodiments, the dentition coupling framework 170 is configured to couple directly to the patient's dentition or is configured to attach to another type of coupling device such as a mold shaped to fit the patient's dentition.

The contact surface 178 is configured to contact the patient's opposing dentition or a structure coupled to the patient's opposing dentition such as the reference structure 122. In the example shown, the contact surface 178 includes three regions that have generally flat surfaces for contact. The holes 180 are recessed between these regions of the contact surface 178. In some embodiments, the regions of the contact surface 178 are generally parallel with the dentition facing surface. However, the contact surface 178 in this example faces in a direction opposite of the dentition facing surface 176. In some embodiments, the contact surface 178 is separated from the dentition facing surface 176 by a distance D. In some embodiments, this distance D corresponds to the height of the dentition coupling device in the occlusal dimension. In some embodiments, the distance D is selected so as to permit the top of a fastening device (e.g., screw heads or knobs) to extend up from the holes 180 without extending to the contact surface 178. Beneficially, such an arrangement prevents the fastening device from making contact with the patient's opposing dentition or the reference structure 122.

Additionally, in some embodiments, the distance D is selected to create a desired occlusal separation between the patient's lower dentition and upper dentition. In some embodiments, the distance D is equal to half of the desired occlusal separation so that the patient can wear a reference structure 122 that also has a similar height and in combination with a clutch that includes the dentition coupling device 160 causes the patent's lower dentition and upper dentition to be separated by a desired amount. In some embodiments, the desired amount of occlusal separation is configurable based on the patient's dental anatomy.

The extension member 182 extends from the dentition coupling framework 170 and is configured to extend out of the patient's mouth when the dentition coupling framework 170 is worn on the patient's dentition. In some embodiments, the extension member 182 is configured so as to be permanently attached to the housing 410 such as by being formed integrally or joined via welding or a permanent adhesive. In other embodiments, the extension member 182 is configured to removably attach to the housing 410. For example, as shown in FIG. 4, the extension member 182 includes a hole 184, which is configured to receive a fastening device (e.g., a screw) to fasten the extension member 182 to the housing 410. In some embodiments, one or both of the extension member 182 and the housing 410 includes alignment structures such as protrusions, ridges, detents, or notches that are configured to cause the extension member 182 and the housing 410 to join together in a uniform and repeatable manner. Additionally or alternatively, some embodiments use magnets to couple the extension member 182 and the housing 410.

Figure 5:
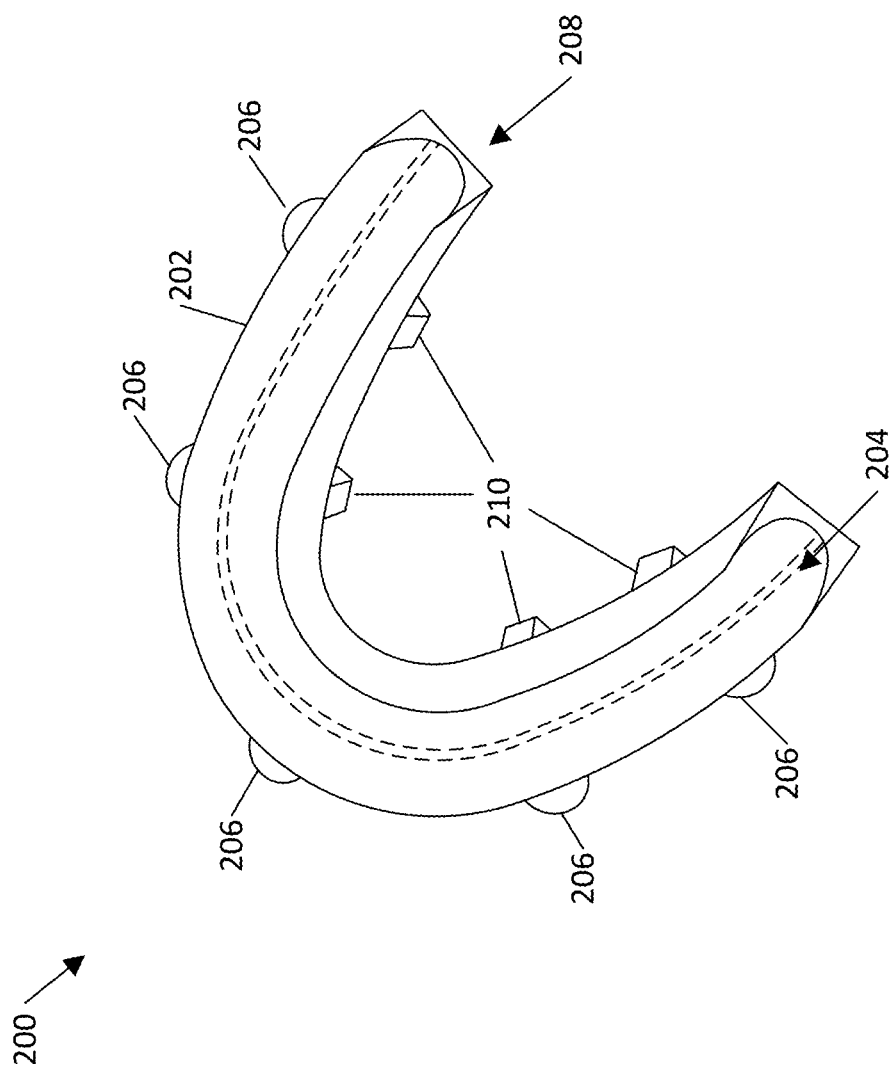
FIG. 5 illustrates an example impression device that is configured to mate with the dentition coupling framework of FIG. 3.

FIG. 5 illustrates an example impression device 200 that is configured to mate with the dentition coupling framework 170 to form an embodiment of the dentition coupling device 124. The illustration in FIG. 5 shows the part of the impression device 200 that would face the patient's dentition oriented toward the top. Thus, the illustration in FIG. 5 shows the impression device 200 rotated 180 degrees from how it would be oriented when mated with the dentition coupling framework 170 of FIG. 3.

In this example, the impression device 200 includes an inner surface 202 that forms a trough 204 that roughly approximates the shape of the dental arch. In some embodiments, the cross-sections of the inner surface 202 (i.e., that are made perpendicular to the dental arch) are also arch shaped. The trough 204 is configured to hold a securing material such as impression material or an adhesive material that operates to secure the impression device to the dentition of the patient. Additionally, in some embodiments, the impression device 200 also includes one or more internal fiducial markers 206, a mating surface 208, and one or more fastening structures 210.

The internal fiducial markers 206 may be spherical and may be sized so as to fit in the patient's mouth more comfortably. Additionally, in some embodiments, the internal fiducial markers 206 may be removable, so that the internal fiducial markers 206 can be removed when the impression device 200 is placed in a patient's mouth. The internal fiducial markers 206 are configured so that when imaged (e.g., by the imaging system 102), the position of the internal fiducial markers 206 can be determined. Various embodiments include various numbers of internal fiducial markers.

In some embodiments, the internal fiducial markers 206 are imaged when the impression device 200 is coupled to the dentition coupling framework 170 and a light source assembly to determine or confirm the relationship between the position of the impression device 200 and fiducial markers attached to the light source assembly or other physical structures of the light source assembly such as surfaces, edges, or corners. However, in some embodiments, the relationship between the position of the impression device 200 and a light source assembly is determined based on a known fixed relationship between the devices and thus it is not necessary to capture images containing both the internal fiducial markers 206 and the light source assembly.

In some embodiments, the internal fiducial markers 206 are imaged with an impression taken using the impression device 200 (e.g., hardened impression material in the trough 204) to determine a relationship between the position of the patient's dentition and the impression device 200 (and therefore the rest of the clutch).

The mating surface 208 is configured to fit against the dentition facing surface 176 when the impression device 200 is coupled to the dentition coupling framework 170. Additionally, the fastening structures 210 are configured to align with the holes 180 of the dentition coupling framework 170 and operate to join the impression device 200 to the dentition coupling framework 170. In some embodiments, the fastening structures 210 are knobs that fit through the holes 180 and may contain a hole for a screw or another fastener. Alternatively, the knobs and holes may be oblong shaped so that when mated the knobs can be twisted to secure the impression device 200 to the dentition coupling framework 170. Other embodiments include other fastening mechanisms.

Although the impression device 200 is configured to cover the occlusal surface of the patient's dentition, alternatives are possible. For example, an impression device may be configured to couple to the buccal or labial (i.e., the outer) surfaces of a patient's dentition without necessarily covering the occlusal surfaces. Beneficially, by not covering the occlusal surface, the patient's teeth may be closed into contact and move around without (or with less) interference from the impression device 200.

Figure 6:
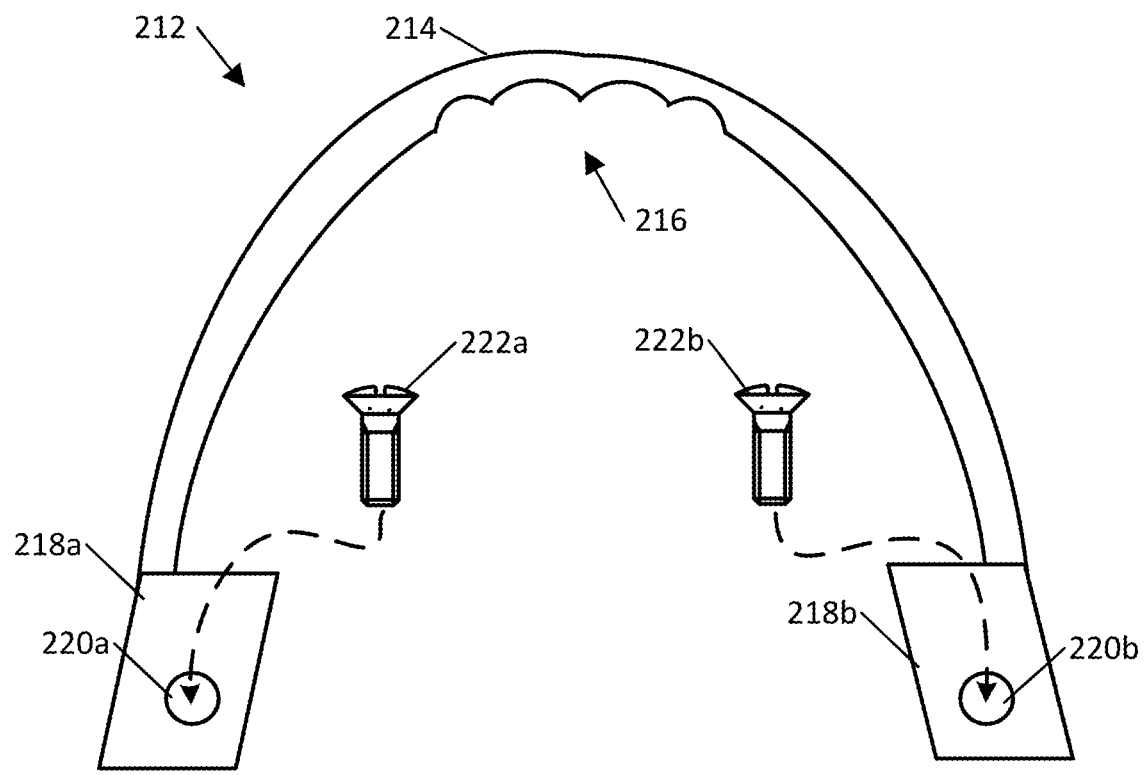
FIG. 6 illustrates an example embodiment of a dentition coupling framework of the clutch or reference structure of FIG. 3.

FIG. 6 illustrates an example dentition coupling device 212. The dentition coupling device 212 is an embodiment of a dentition coupling device such as the dentition coupling device 124. The dentition coupling device 212 is configured to couple to a patient's dentition using temporary anchorage devices such as temporary anchorage devices 222a and 222b. The dentition coupling device 212 includes an arch portion 214 and securing regions 218a and 218b. The arch portion 214 is a rigid structure and may be shaped to fit along a surface of the patient's dentition. The arch portion 214 may be custom fabricated for a patient based on an impression of the patient's dentition or measurements of the patent's dentition. The arch portion 214 may include a contoured portion 216 that has a shape that matches the lingual/buccal (outer) surfaces of at least some of the patient's teeth. For example, the dentition coupling device 212 may be produced using rapid fabrication technology based on an impression of the patient's dentition. However, in some embodiments, the dentition coupling device 212 does not include a contoured portion (e.g., when a patient is completely or primarily edentulous).

In some embodiments, the securing regions 218a and 218b include surfaces that match the contour of portions of the patient's dentition (e.g., based on a previously captured impression of the patient's dentition). The securing regions may align with an edentulous region of the patient's dentition or another portion of the patient's dentition. Although the example shown in FIG. 6 includes two securing regions, the dentition coupling device 212 can include just one securing region or more than two securing regions.

The securing regions 218a and 218b include fastener receivers 220a and 220b respectively. The fastener receivers 220a and 220b are configured to receive a fastener such as the temporary anchorage devices 222a and 222b. In some embodiments, the fastener receivers 220a and 220b are apertures through which the bone penetrating portions of the temporary anchorage devices 222a and 222b may pass. The fastener receivers 220a and 220b may be sized so as to prevent the heads of the temporary anchorage devices 222a and 222b from passing. In this manner, the temporary anchorage devices 222a and 222b secure the dentition coupling device 212 to the patient's dentition.

Alternatively, the fastener receivers 220a and 220b include clasps to couple to the heads of temporary anchorage devices 222a and 222b. In these embodiments, the temporary anchorage devices 222a and 222b may be inserted into the patient's bone tissue before the dentition coupling device 212 is placed on the patient's dentition. Then, the dentition coupling device 212 can be placed on the patient's dentition so that the clasps couple with the heads of the already implanted temporary anchorage devices 222a and 222b.

In these embodiments, the temporary anchorage devices 222a and 222b may be placed in the patient's dentition. After the temporary anchorage devices 222a and 222b are placed, an impression of the patient's dentition can be captured. The dentition coupling device 212 can then be custom designed based on that impression to match at least a portion of the contour of the patient's dentition and to include clasps to mate with the implanted temporary anchorage devices 222a and 222b. The dentition coupling device 212 can then be fabricated using for example rapid fabrication technologies.

The temporary anchorage devices 222a and 222b are fastening devices formed from a biocompatible material (e.g., titanium) that are configured to penetrate through the patient's gum tissue and into the patient's bone tissue. The temporary anchorage devices 222a and 222b may include threads that are configured to secure the temporary anchorage devices 222a and 222b. The temporary anchorage devices 222a and 222b may include heads with various configurations. For example, the temporary anchorage devices 222a and 222b may include a receiver for a tightening tool. Additionally or alternatively, the temporary anchorage devices 222a and 222b may include a head with a spherical shape that can serve as a fiducial for determining the relationship between the dentition coupling device 212 and the patient's dentition. Alternatively, when the dentition coupling device 212 is custom fabricated to fit a particular patient's dentition, the relationship between the dentition coupling device 212 and the patient's dentition may be inferred.

Figure 7:
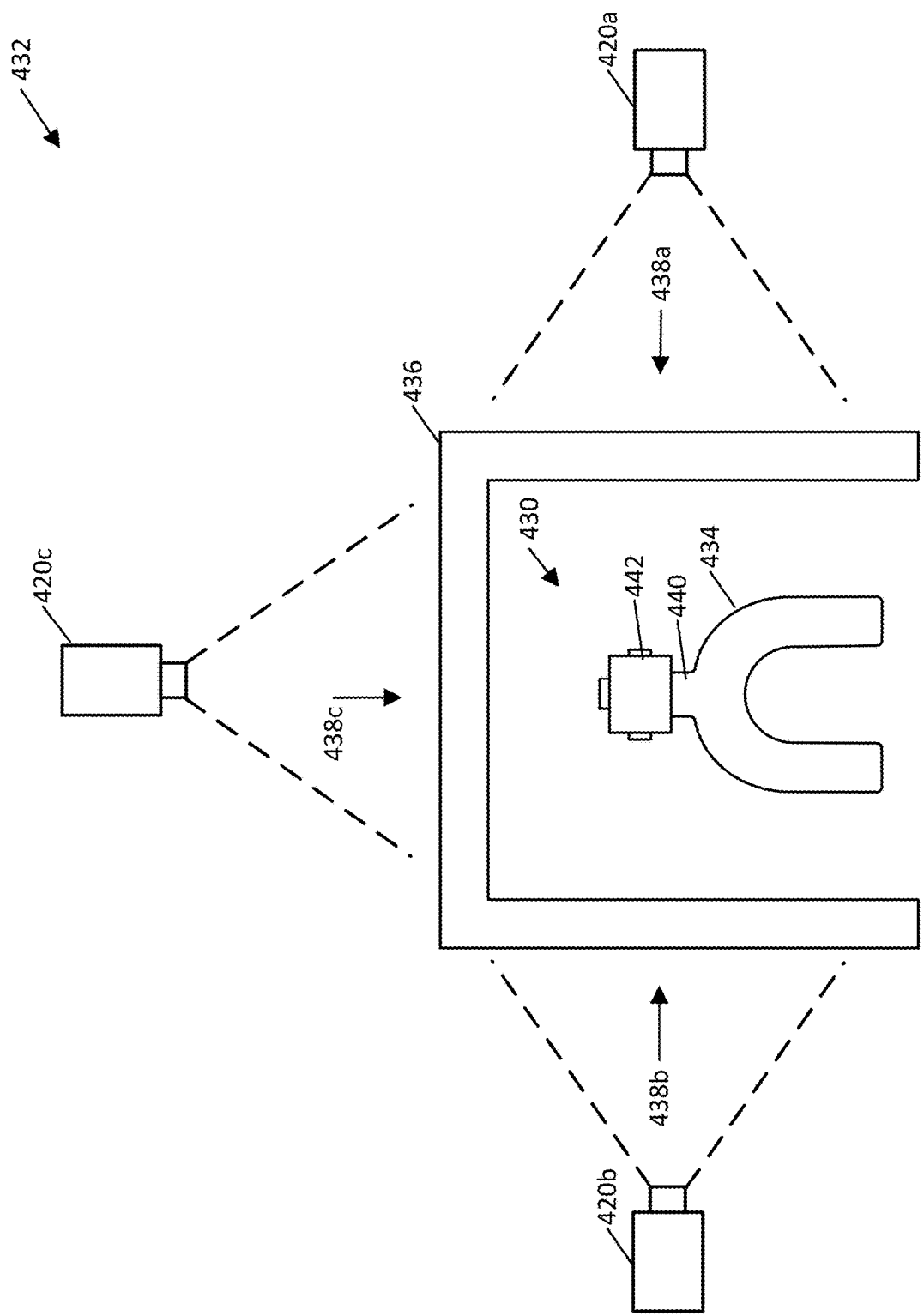
FIG. 7 illustrates a top view of an embodiment of the reference structure of FIG. 2 and an embodiment of the imaging system of FIG. 1.

FIG. 7 illustrates a top view of an embodiment of a reference structure 430 and an embodiment of an imaging system 432. The reference structure 430 is an example of the reference structure 122. The imaging system 432 is an example of the imaging system 102.

The reference structure 430 may be similar to the clutch 400, except that the reference structure 430 is configured to be worn on the opposite arch from the clutch 400. The reference structure 430 includes a dentition coupling device 434, an extension member 440, and a light source assembly 442. The dentition coupling device 434 is an example of the dentition coupling device 130 and may be similar to the example dentition coupling devices previously described with respect to embodiments of the clutch. The light source assembly 442 is an example of the position indicator system 134.

The dentition coupling device 434 is configured to removably couple to the dentition of the patient. The dentition coupling device 434 is coupled to the opposite arch of the patient's dentition as the clutch (e.g., the dentition coupling device 434 couples to the maxillary arch when the clutch 400 is coupled to the mandibular arch). In some embodiments, the dentition coupling device 434 is coupled to the extension member 440 that is configured to extend out through the patient's mouth when the dentition coupling device 434 is coupled to the patient's dentition. The extension member 440 may be similar to the extension member 408.

In the embodiment shown, the extension member 440 is rigidly coupled to a light source assembly 442. The light source assembly 442 may be permanently coupled to the extension member 440. In other embodiments, the extension member 440 is configured to removably couple to the light source assembly 442. For example, the extension member 440 may couple to the light source assembly 442 via a thumb screw or another type of fastener.

The imaging system 432 includes a screen framework 436, screens 438a, 438b, and 438c (referred to collectively as screens 438), and cameras 420a, 420b, and 420c (referred to collectively as cameras 420). The screen framework 436 and the screens 438 together are an example of the screen assembly 112. The cameras 420 are an example of the optical sensing assembly 110.

The screen framework 436 is a structure that positions the screens 438 to surround a patient's mouth so that light emitted by the reference structure 430 or a clutch (not shown) worn by the patient will intersect with the screens 438. Although alternatives are possible, the screen framework 436 may be U-shaped, having one side for each of the screens 438. In this example, the screen framework 436 orients the screen 438c at a right angle from the screen 438a and at a right angle from the screen 438b. In at least some implementations, the screens 438 are planar or substantially planar and have a rectangular shape. In some embodiments, the screen framework 436 is configured to connect to the top of the screens 438 (e.g., if the screens 438 are formed from a rigid material). Alternatively, the framework may partially or fully surround the screens 438 (e.g., if the screens 438 are formed from a flexible material).

Other embodiments may include different numbers of the screens 438 and different arrangements of the light source assembly 442. For example, some embodiments may include two light emitters and two screens. One of the screens may be disposed in front of the patient (i.e., in the anterior direction) and one may be disposed on one side of the patient (i.e., in a lateral direction). Additionally, some embodiments may include a third light source that emits light up or down (i.e., in the superior or inferior direction). Example embodiments that include two screens disposed on opposite sides of the patient and three light emitters are illustrated and described with respect to at least FIGS. 22-28.

The screens 438 may be formed from a translucent material so that the points where the light beams emitted by the light source assembly 442 intersect with the screens 438 may be viewed from outside of the screens 438. Images that include these points of intersection may be recorded by the cameras 420. The motion determining device 106 may then analyze these captured images to determine the points of intersection of the light beams with the screens 438 to determine the location of the light source assembly 442. The position of the light source assembly 404 of the clutch 400 (not shown) may be determined in a similar manner.

Figure 10:
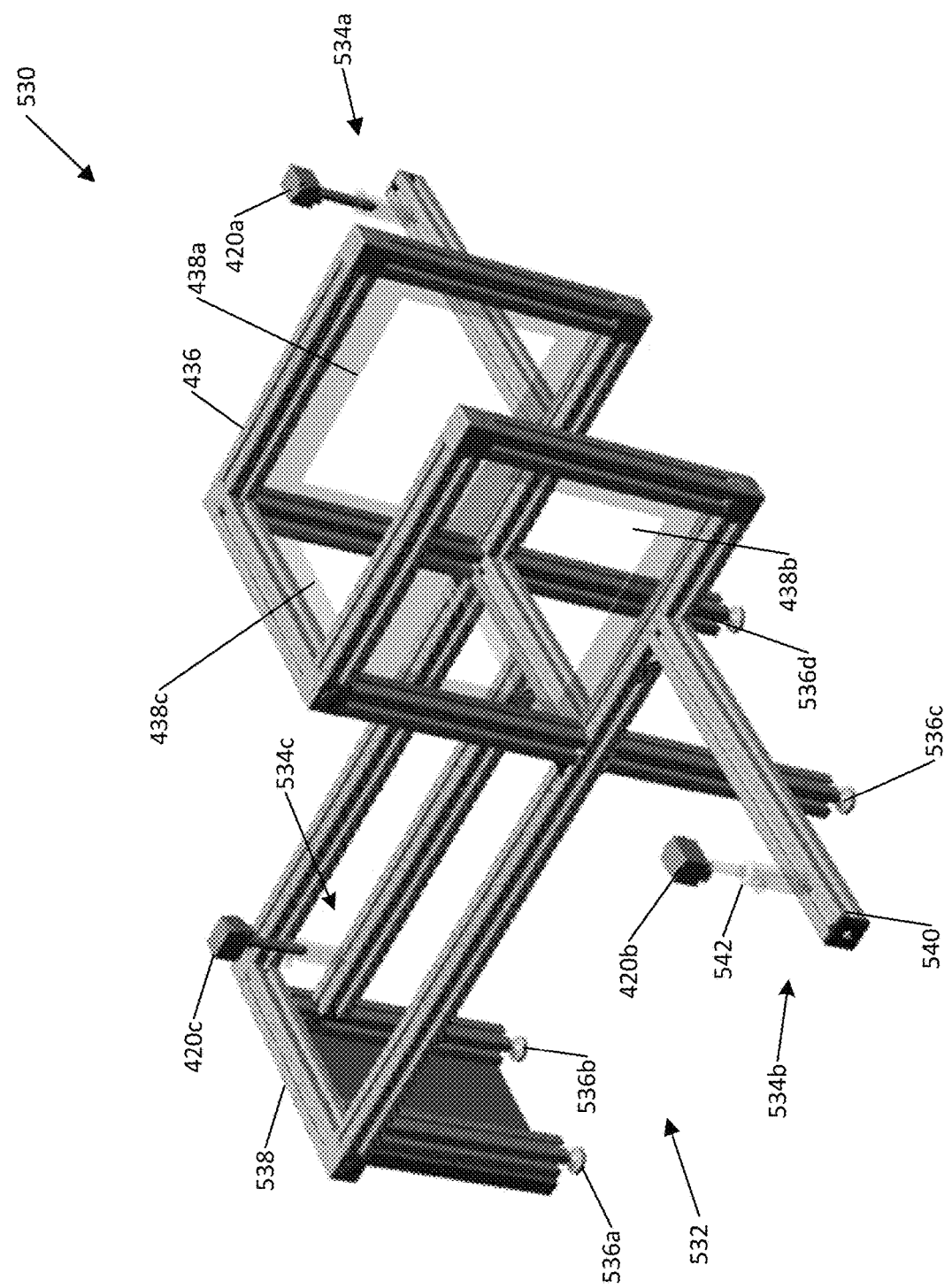
FIG. 10 illustrates an example of an imaging system of FIG. 1.

The cameras 420 are positioned and oriented to capture images of the screens 438. For example, the camera 420a is positioned and oriented to capture images of the screen 438a, the camera 420b is positioned and oriented to capture images of the screen 438b, and the camera 420c is positioned and oriented to capture images of the screen 438c. In some embodiments, the cameras 420 are mounted to the screen framework 436 so that they move with the screen framework 436. For example, each of the cameras 420 may be coupled to the screen framework 436 by a camera mounting assembly such as is shown in FIG. 10. In this manner, the position and orientation of the cameras 420 relative to the screens 438 does not change if the screen framework 436 is moved.

The cameras 420 may store a series of images or transmit images as the images are captured to a storage device or a computing device such as the motion determining device 106. In some embodiments, the cameras 420 transmit images over a wired network. In other embodiments, the cameras 420 transmit images over a wireless network.

The system 100 may include techniques to compensate for variations in the alignment of the cameras to the screens or the screens to one another. For example, a calibration pattern of known shape and dimensions may be projected onto the screens and captured with the cameras. The recorded images may be analyzed to identify deviations from the known shape and dimensions. A translation can then be generated to translate the captured image to the expected shape and dimensions. This is one example of a method to compensate for variations in alignment; other methods are used in other embodiments. Similar methods can be used to compensate for variations in the relative positions of the screens (e.g., by projecting a pattern of known relation on multiple screens). In one example, light that is expected to be collinear is projected on multiple screen simultaneously. Any deviations in the collinearity of the light in the captured images can then be compensated (e.g., using a transformation). Similar techniques can also be used to compensate for field of view distortion in the cameras. An example calibration plate is illustrated and described with respect to at least FIG. 19.

Figure 8:
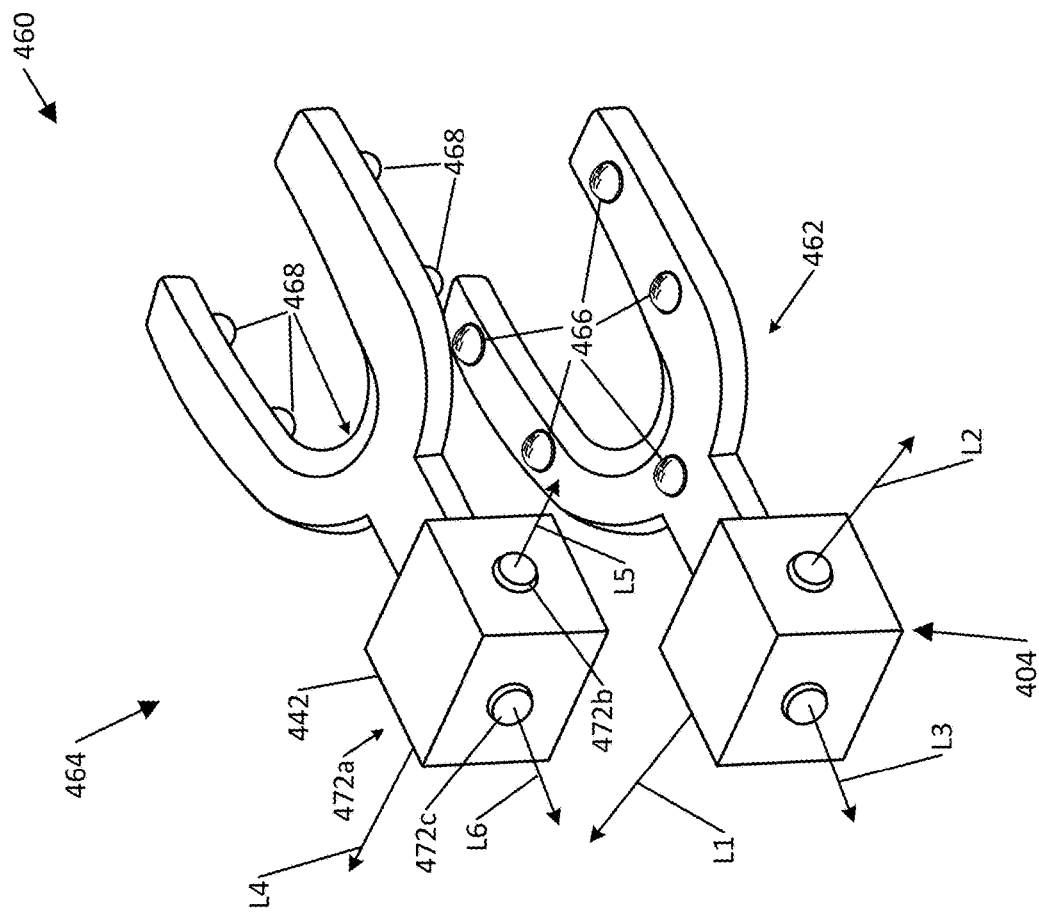
FIG. 8 illustrates another embodiment of the patient assembly of FIG. 1.

FIG. 8 illustrates an embodiment of the patient assembly 460. The patient assembly 460 is an example of the patient assembly 104. The patient assembly 460 includes a clutch 462 and a reference structure 464.

The clutch 462 may be similar to the clutch 400. However, the clutch 462 includes a plurality of internal fiducial markers 466. The internal fiducial markers 466 are usable to establish a static relationship between the clutch and the patient's dentition. The internal fiducial markers 466 may be similar to the internal fiducial markers 206. Additionally, the internal fiducial markers 466 may be used to establish a static relationship between a dentition coupling device of the clutch 462 and a light source assembly of the clutch 462. Various embodiments include various numbers of the internal fiducial markers 466.

The reference structure 464 may be similar to the reference structure 430. However, the reference structure 464 includes internal fiducial markers 468 that are usable to establish a static relationship between the reference structure 464 and the patient's dentition. The internal fiducial markers 468 may be similar to the internal fiducial markers 206. Various embodiments include various numbers of the internal fiducial markers 468.

Additionally, the reference structure 464 includes the light source assembly 442. The light source assembly 442 includes light emitters 472a, 472b, and 472c that emit light beams L4, L5, and L6. Similar to the light beams L1, L2, and L3 emitted by the clutch 462, the light beams L4, L5, and L6 are directed to intersect with screens (not shown) such as the screens 438.

The light beams L4, L5, and L6 may have a different color (i.e., have a different wavelength) than the light beams L1, L2, and L3. In this manner, the motion determining device 106 can distinguish the light beams L1, L2, and L3 from the light beams L4, L5, and L6 so that the relative positions of the light source assemblies on the clutch 462 and the reference structure 464.

Additionally or alternatively, the light source assembly 442 of the reference structure 464 and the light source assembly 404 of the clutch 462 may strobe on and off in a synchronized manner so that the motion determining device 106 may determine which points on the images of the screens 438 (not shown) correspond to the light source assembly 442 from the reference structure 464 and which correspond to the light source assembly 404 of the clutch 462. For example, the imaging system 102 may capture sequential frames of images, while the light source assembly on the clutch 462 may be activated during odd frames and the light source assembly on the reference structure 464 may be activated during even frames (or vice versa). For example, the light source assembly on the clutch 462 may emit light in phases (e.g., alternating between an on phase and an off phase) and the light sources assembly on the reference structure may emit light in phases (e.g., alternating between a reference on phase and a reference off phase) that are out of phase with each other (e.g., the light source assembly of the clutch is on when the light source assembly of the reference structure is off, and the light source assembly of the clutch is off when the light source assembly of the reference structure is on).

As another example, one of the light source assemblies may strobe, while the other does not, or both may strobe but at different frequencies or with different patterns. Another alternative is that the light beams emitted from the reference structure 464 are distinguished from the light beams emitted by the clutch 462 based on position (e.g., the beams that are higher may be determined to be emitted by the reference structure 464 as it is configured to attach to the upper arch).

Figure 9:
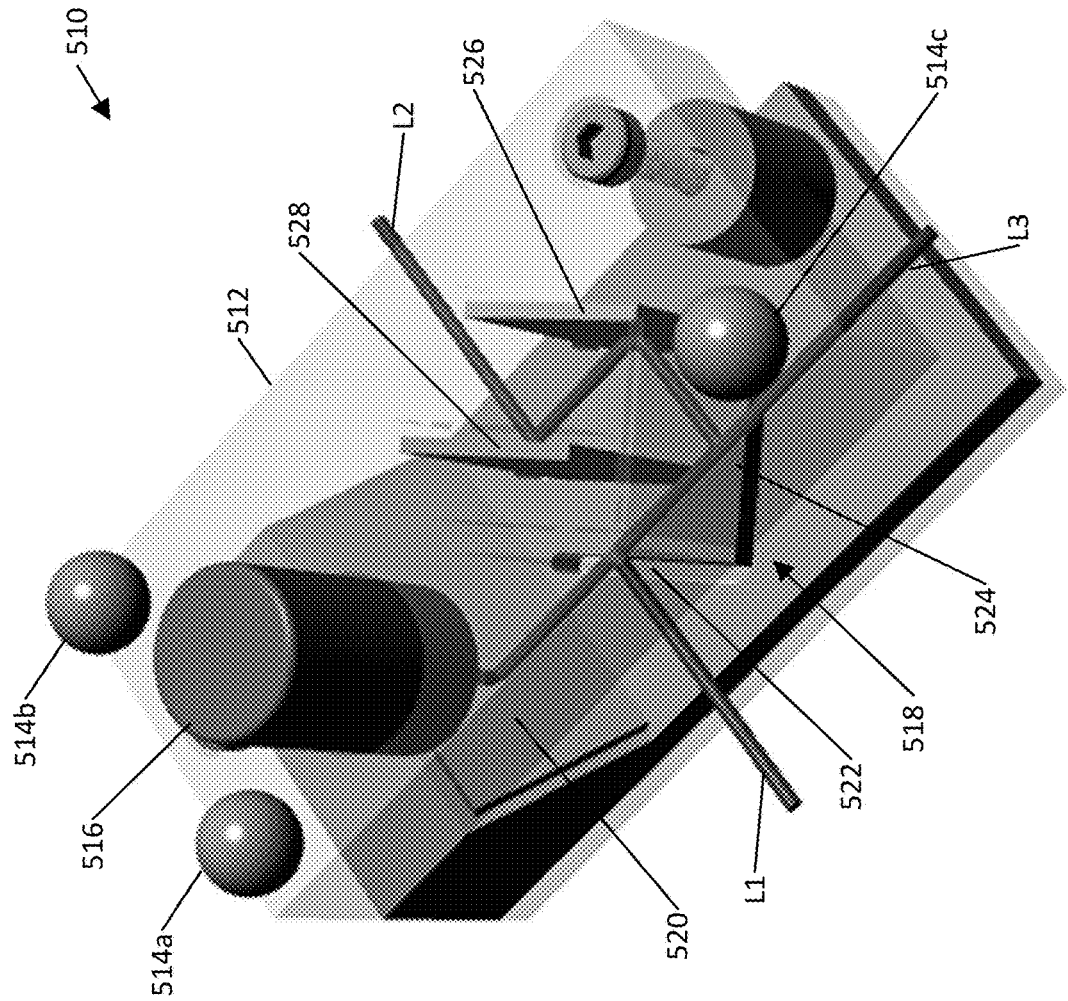
FIG. 9 illustrates an example of a light source assembly and an embodiment of the clutch position indicator of FIG. 2.

FIG. 9 illustrates an embodiment of a light source assembly 510 that uses a single laser source. The light source assembly 510 may be similar to the previously described light source assemblies such as the light source assembly 404. The light source assembly 510 emits three laser beams L1, L2, and L3 from a single laser emitter 516.

The light source assembly includes a housing 512, fiducial markers 514a, 514b, and 514c (referred to collectively as fiducial markers 514), the laser emitter 516, and a beam splitter assembly 518.

The housing 512 surrounds the light source assembly 510 and beam splitter assembly 518. The housing 512 may contain one or more apertures through which light may be emitted by the light source assembly 510. In some embodiments, the housing 512 is formed from a rigid or semi-rigid material, such as plastic, metal, ceramic, or a composite material. In some embodiments, the housing 512 may be a single integral component. Alternatively, the housing 512 may include a coupling structure configured to removably couple together the multiple components of the housing. In some embodiments, the top component of the housing 512 includes a connector that is configured to mate with a connector on the bottom component of the housing 512. The components of the housing may also include holes or receivers for screws or other fasteners to couple the components together.

In some implementations, the fiducial markers 514 are disposed on a surface of the housing 512 and can be used to establish the position of the light source assembly 510 relative to a clutch such as the clutch 400 or a reference structure such as the reference structure 430. Some embodiments do not include fiducial markers and the relationship between the light source assembly 510 and the clutch or reference structure is established in advance such as when the light source assembly 510 is permanently coupled to the clutch or reference structure. The relationship may be established based on the design of the clutch or reference structure. To address potential manufacturing variances, the clutch or the reference structure may be characterized using a touch probe or similar device. In some implementations one or more surfaces, edges, or corners of the housing 512 are used to define a relationship between the clutch or reference structure.

In the example of FIG. 9, the light source assembly 510 includes a single laser emitter 516. Although alternatives are possible, the laser emitter 516 may be a semiconductor laser emitter such as a laser diode emitter or a solid-state laser emitter such as diode-pumped solid-state laser emitter. The laser emitter 516 emits a beam of collimated light into the beam splitter assembly 518.

The beam splitter assembly splits the laser beam emitted by the laser emitter 516 into three separate light beams L1, L2, and L3. In some embodiments, the beam splitter assembly 518 contains three reflector surfaces 520, 526, and 528 and two beam splitters 522 and 524. In this example, the collimated light from the laser emitter 516 is initially emitted as a vertical light beam on to the first reflector surface 520. The vertical light beam is then reflected by the first reflector surface 520 to form a horizontal light beam. In some embodiments, the laser emitter 516 is orientated to emit the light beam horizontally and the first reflector surface 520 is omitted.

This horizontal light beam then passes through the first beam splitter 522. The first beam splitter 522 splits the horizontal light beam into two light beams that are substantially orthogonal to one another. One of the light beams is emitted out of the housing of the light source assembly 510 as light beam L1, while the other light beam continues in a direction that is the same as or similar to the direction of the horizontal light beam.

The horizontal light beam continues on until it reaches the second beam splitter 524. The second beam splitter 524 again splits the horizontal light beam into two light beams that are substantially orthogonal to one another. One of the light beams continues in the same direction as the incoming horizontal light beam and is emitted out of the housing of the light source assembly 510 as light beam L3. The other light beam travels in a direction that is substantially orthogonal to the light beam L3 and opposite the light beam L1. This light beam continues until it reaches the second reflector surface 526. The second reflector surface 526 reflects the light beam orthogonally such that it travels in the opposite direction as light beam L3 until reaching the third reflector surface 528. The third reflector surface 528 once again reflects the light beam orthogonally to produce the light beam L2 travelling in a direction that is substantially opposite to but collinear with the light beam L1. The reflected light beam is emitted out of the housing of the light source assembly 510 as light beam L2. In some aspects, the second beam splitter 524, the second reflector surface 526, and the third reflector surface 528 are disposed so as to cause the light beam L1 and the light beam L2 to be collinear.

In some embodiments, the light beams L1 and L2 are substantially parallel to each other, but directed in opposite directions, and the light beam L3 is substantially perpendicular to the light beams L1 and L2. Further, in some embodiments, the light beams L1 and L2 are collinear. In at least some embodiments, the light source assembly 510 is configured to position the laser emitter 516 so that the light beams L1, L2, and L3 are approximately co-planar with the occlusal plane of the patient's dentition.

Alternatively, some embodiments, are configured so that the light beams L1 and L2 are not collinear when emitted. These embodiments, may omit the second reflector surface 526 and the third reflector surface 528. Embodiments in which the light beam L3 is not perpendicular to the light beam L1 are further illustrated and described with respect to at least FIGS. 22-28.

FIG. 10 illustrates an embodiment of an imaging system 530. The imaging system 530 is another example of the imaging system 102.

This example embodiment of the imaging system 530 includes the cameras 420a, 420b and 420c, a stand 532, and camera mounting assemblies 534a, 534b, and 534c. The imaging system 530 also includes the screen framework 436, and the screens 438a, 438b, and 438c.

The stand 532 is a structure that positions the imaging system for use in capturing movement of a clutch and reference structure in a patient's mouth. The stand 532 includes legs 536a, 536b, 536c, 536d (referred to collectively as legs 536) and mounting framework 538.

The legs vertically position the mounting framework 538. Some embodiments of the stand 532 are designed to be placed on the floor and the legs 536 have a longer length. Other embodiments of the stand 532 are designed to be placed on an elevated surface such as a countertop or table top and the legs 536 have a shorter length. The length of the legs 536 may be fixed or adjustable.

The mounting framework 538 is a structure that other components of the imaging system 530 are mounted to. In some embodiments, the mounting framework 538 comprises a plurality of horizontally oriented elongate members. In other embodiments, the mounting framework 538 may include a surface as well. As shown in FIG. 10, the camera mounting assemblies 534 and the screen framework 436 are mounted to the mounting framework 538.

The camera mounting assemblies 534 are assemblies that position and orient the cameras 420 relative to the screens 438. The camera mounting assemblies 534 may include various components to adjust the position and orientation of the cameras 420. In at least some embodiments, the position of the cameras 420 on the camera mounting assemblies 534 is selected so that the field of view of the cameras 420 approximately coincides with the screens 438. Alternatively, the field of view of the cameras 420 may approximately coincide with a portion of the screen in which the light emitted by a clutch device would be likely to intersect.

For purposes of explanation, the camera mounting assembly 534b is described in greater detail herein. This discussion is equally applicable to the camera mounting assemblies 534a and 534b. The camera mounting assembly 534b includes a sliding rail 540 and a vertical positioning system 542.

The sliding rail 540 is mounted to the mounting framework 538 below the screen 438b. The sliding rail 540 extends away from the screen 438b in a direction that is approximately normal to the surface of the screen 438b. The sliding rail 540 includes a channel and a sliding element to which the bottom end of the vertical positioning system 542 is connected. The sliding element can slide through the channel to adjust the distance of the camera 420b from the screen 438b. The sliding rail 540 also includes a locking mechanism, which when engaged prevents the sliding element from moving through the channel.

The vertical positioning system 542 is mounted to the movable element on one end and the camera 420b on the other. The vertical positioning system 542 is a structure that vertically positions the camera 420b. In some embodiments, the height of the vertical positioning system 542 is adjustable. For example, the vertical positioning system 542 may include a telescoping component that slides up and down to adjust the height of the vertical positioning system 542. The vertical positioning system 542 may also include a locking component that prevents the telescoping element from moving so as to lock the height of the vertical positioning system 542.

Figure 11:
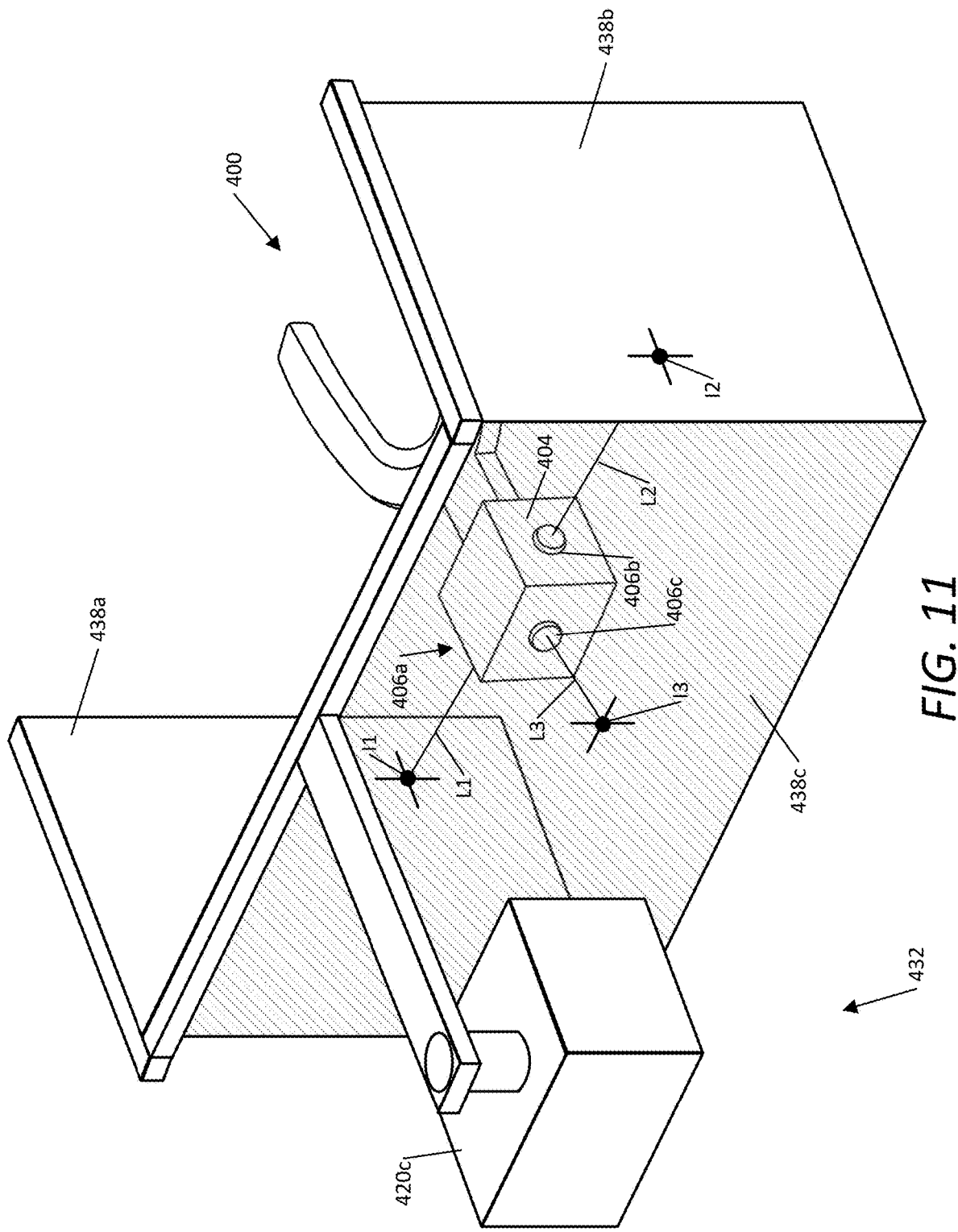
FIG. 11 illustrates a perspective view of part of the embodiment of the reference structure of FIG. 13 and an embodiment of the clutch of FIG. 2.

FIG. 11 illustrates a perspective view of the clutch 400 disposed within the screens 438 of the imaging system. In this example, the screen 438c is shown as transparent so that the clutch 400 can be seen.

In this example, the light emitter 406a is emitting a light beam L1, which intersects with the screen 438a at intersection point I1; the light emitter 406b is emitting a light beam L2, which intersects with the screen 438b at intersection point I2; and the light emitter 406c is emitting a light beam L3, which intersects with the screen 438c at intersection point I3. As the position and orientation of the clutch 400 change relative to the screens 438, the locations of at least some of the intersection points I1, I2, and I3 will change as well.

The camera 420c captures an image of the screen 438c, including the intersection point I3 of the light beam L3 emitted by the light emitter 406c. The camera 420c may capture a video stream of these images. Similarly, although not shown in this illustration, cameras 420a and 420b capture images of the screens 438a and 438b and the intersection points I1 and I2.

The captured images from the cameras 420 are then transmitted to the motion determining device 106. The motion determining device 106 may determine the location of the intersection points I1, I2, and I3, and from those points the location of the light source assembly 404. In some embodiments, a point of common origin within the light source assembly 404 for the light beams L1, L2, and L3 is determined based on the location of the intersection points I1, I2, and I3 (e.g., the point at which the light beams intersect). Based on the determined locations of the light beams, the location and orientation of the clutch 400 relative to the screens 438 can be determined.

In other embodiments, the motion determining device 106 fits the intersection points I1, I2, and I3 to a plane. The motion determining device 106 then determines the location of the light source assembly 404 by finding an intersection point of the light beam L3 with either of light beams L2 or L3.

Figure 12:
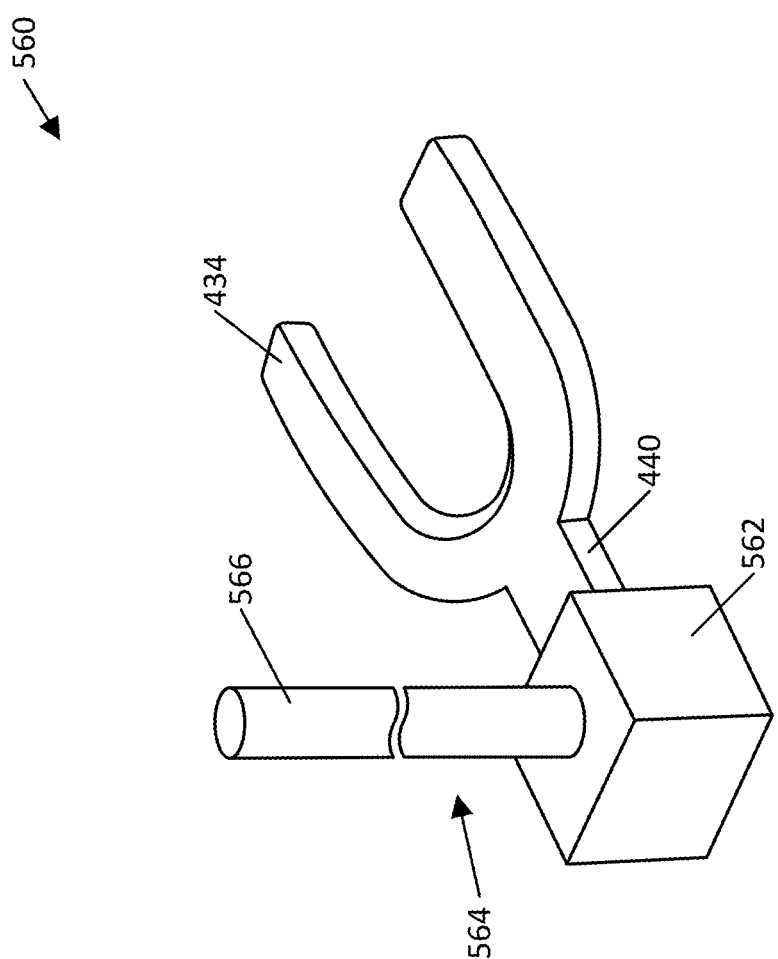
FIG. 12 illustrates a perspective view of part of the embodiment of the reference structure of FIG. 13.

FIG. 12 illustrates a perspective view of a reference structure 560. The reference structure 560 is configured to mount to an imaging system such as the imaging system 102. In some embodiments, the imaging system 102 is supported by and moves with the reference structure 560. In other embodiments, the imaging system 102 secures the reference structure 560 so that the reference structure 560 cannot move and consequently the patient's upper jaw and head cannot move.

The reference structure 560 includes the dentition coupling device 434, the extension member 440, a housing 562, and a framework mounting assembly 564. The housing 562 is a structure that includes a connector for connecting with the framework mounting assembly 564. The housing 562 may include features such as notches or ridges that operate to ensure that the connection to the framework mounting assembly 564 is repeatable and consistent (e.g., when connected the relative orientation and position of the housing 562 and framework mounting assembly 564 are always substantially the same). In some embodiments, the housing 562 is formed from a rigid or semi-rigid material, such as plastic, metal, ceramic, or a composite material. In some embodiments, the housing 562 and the dentition coupling device 434 are integral (e.g., are formed from a single material or are coupled together in a manner that is not configured to be separated by a user). Alternatively, the housing 562 may include a connector for establishing a consistent and repeatable connection with the extension member 440. Although not shown in FIG. 12, some embodiments of the housing 562 house a light source assembly such as the light source assembly 442 or other components as well.

In the embodiment shown, the framework mounting assembly 564 includes a framework mounting post 566. The framework mounting post 566 is a post that extends from the housing 562 approximately vertically up above a patient's mouth when the reference structure 560 is being worn by the patient. The framework mounting post 566 is configured to connect to the screen framework as shown in FIG. 13.

Figure 13:
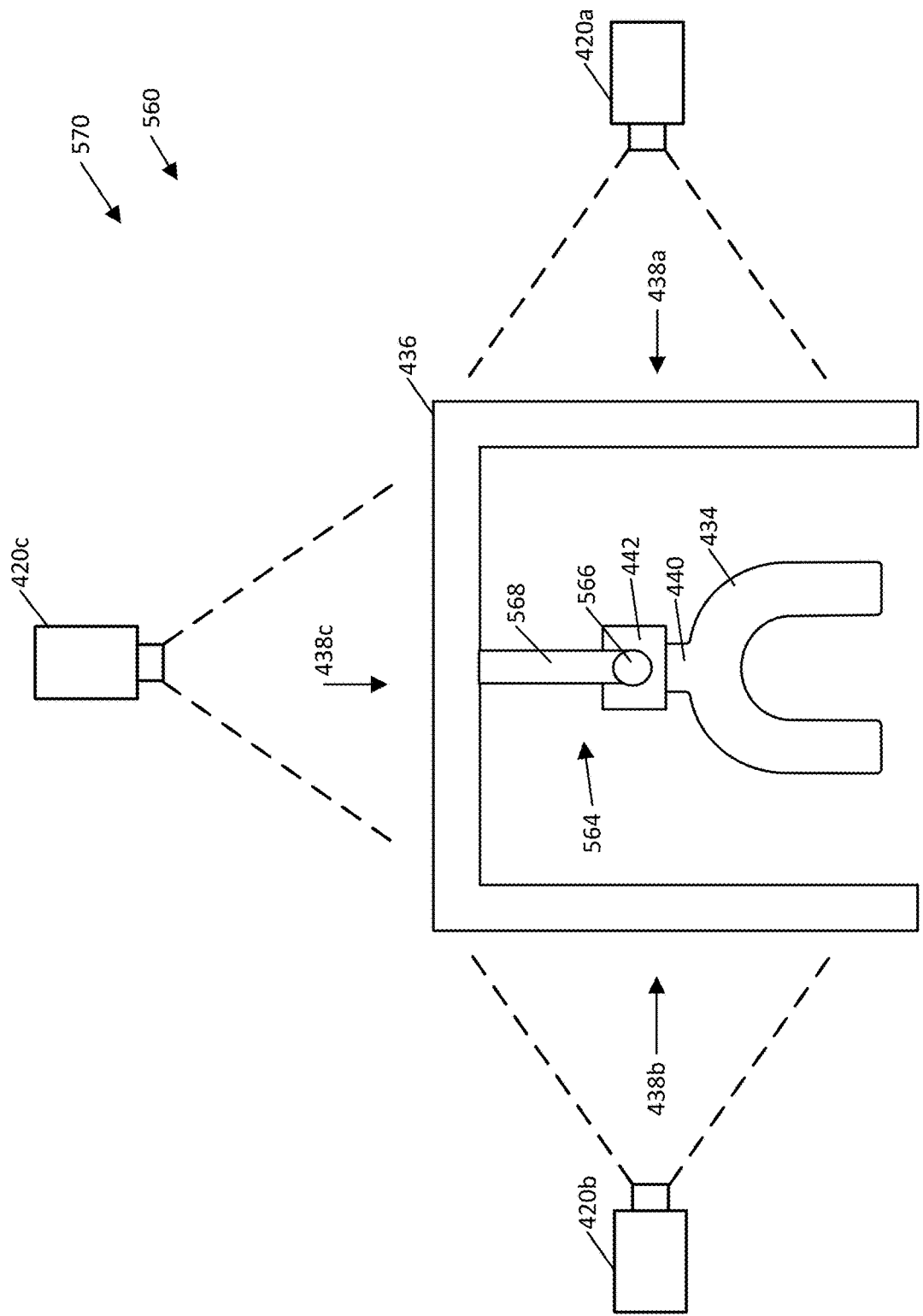
FIG. 13 illustrates a top view of an embodiment of the reference structure of FIG. 2 and an embodiment of the imaging system of FIG. 1.

FIG. 13 illustrates a top view of an embodiment of the reference structure 560 mounted to an imaging system 570. The imaging system 570 is another example of the imaging system 102.

The reference structure 560 is mounted to the imaging system 570 with the framework mounting assembly 564. In the embodiment shown, the framework mounting assembly 564 includes the framework mounting post 566 and a framework mounting extension member 568. The framework mounting assembly 564 is a rigid structure that operates to couple the screen framework 436 to the dentition coupling device 434. The framework mounting extension member 568 is joined to an end of the framework mounting post 566 that is opposite of the dentition coupling device 434. The framework mounting extension member 568 extends horizontally out away from the patient's mouth when the reference structure 560 is being worn by the patient.

The framework mounting extension member 568 may have different sizes in various embodiments as well and the size may depend on the size of the screens 438. For example, the framework mounting extension member 568 may have a length that positions the horizontal center of screens 438a and 438b to approximately line up with the patient's lips. In this manner, the framework mounting assembly 564 serves to help ensure the patient stays approximately centered in the screens during measurement operations.

Figure 14:
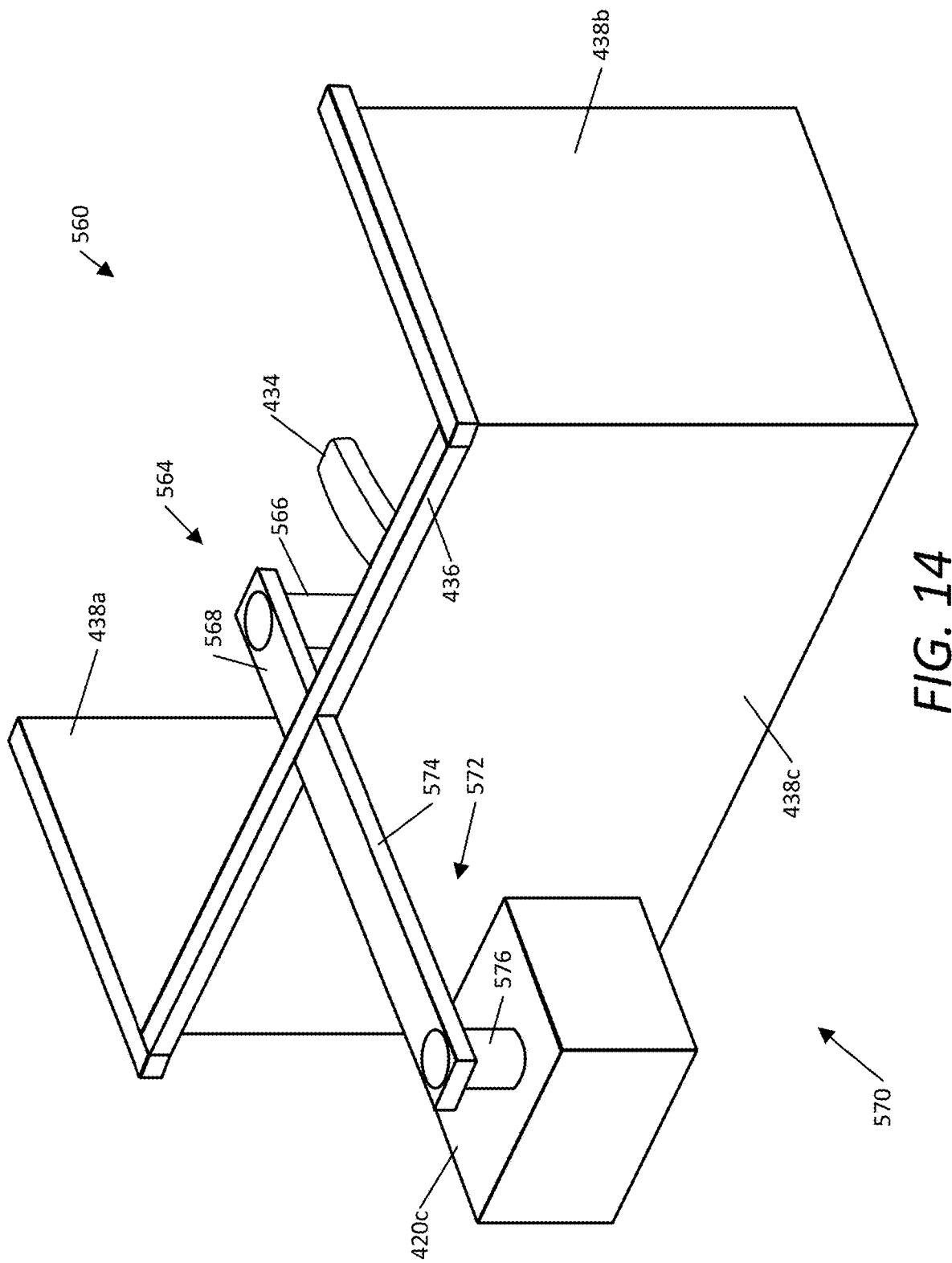
FIG. 14 illustrates a perspective view of part of the embodiment of the reference structure of FIG. 13 and of the imaging system of FIG. 12.

FIG. 14 illustrates a perspective view of part of the reference structure 560 and part of the imaging system 570.

The reference structure 560 includes a dentition coupling device 434. The dentition coupling device 434, the screen framework 436, the screens 438, the framework mounting assembly 564, the framework mounting post 566 and the framework mounting extension member 568 are similar to the examples previously described.

The framework mounting extension member 568 is attached to the screen framework 436. A camera mounting assembly 572 is also attached to the screen framework 436. The camera mounting assembly 572 includes a camera mounting extension member 574 and a camera mounting post 576. The camera mounting extension member 574 couples to the screen framework 436 and extends to position the camera 420c out away from the patient. The length of the camera mounting extension member 574 varies in various embodiments and depends on the size of the screen 438c and the angle of view of the camera 420c. In at least some embodiments, the length of the bracket is selected to position the camera 420c so that the field of view of the camera 420c approximately coincides with the screen 438c. Alternatively, the field of view of the camera 420c may approximately coincide with a portion of the screen in which the light emitted by a clutch device would be likely to intersect.

Figure 15:
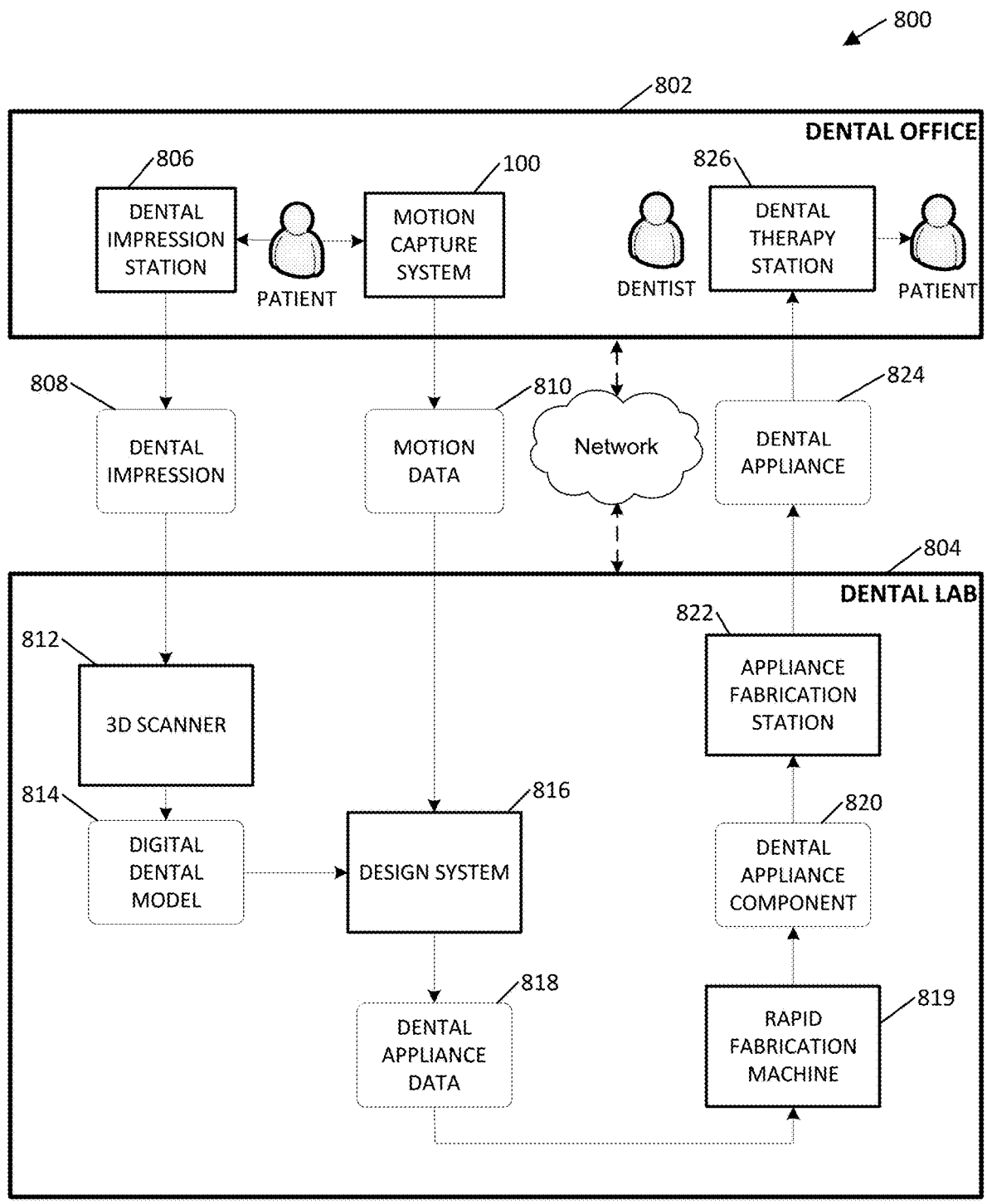
FIG. 15 is a schematic block diagram illustrating an example of a system for using jaw motion captured by the system of FIG. 1 to fabricate a dental appliance or provide dental therapy.

FIG. 15 is a schematic block diagram illustrating an example of a system 800 for using jaw motion captured by the motion capture system 100 to fabricate a dental appliance 824 or provide dental therapy. In this example, the system 800 includes a dental office 802 and a dental lab 804.

The example dental office 802 includes a dental impression station 806, the motion capture system 100, and a dental therapy station 826. Although shown as a single dental office in this figure, in some embodiments, the dental office 802 comprises multiple dental offices. For example, in some embodiments, one or both of the dental impression station 806 and the motion capture system 100 are in a different dental office than the dental therapy station 826. Further, in some embodiments, one or more of the dental impression station 806, the motion capture system 100, and the dental therapy station 826 are not in a dental office.

The example dental impression station 806 generates a dental impression 808 of the dentition of the patient. The dental impression 808 is a geometric representation of the dentition of the patient. In some embodiments, the dental impression 808 is a physical impression captured using an impression material, such as sodium alginate, or polyvinylsiloxane. In other embodiments, other impression materials are used as well. In some embodiments, the dental impression is captured by the impression device 200 of the motion capture system 100. In other words, some embodiments do not include a dental impression station 806 that is separate from the motion capture system 100.

In some embodiments, the dental impression 808 is a digital impression. In some embodiments, the digital impression is represented by one or more of a point cloud, a polygonal mesh, a parametric model, or voxel data. In some embodiments, the digital impression is generated directly from the dentition of the patient, using for example an intraoral scanner. Example intraoral scanners include the TRIOS Intra Oral Digital Scanner, the Lava Chairside Oral Scanner C.O.S., the Cadent iTero, the Cerec AC, the Cyrtina IntraOral Scanner, and the Lythos Digital Impression System from Ormco. In other embodiments, a digital impression is captured using other imaging technologies, such as computed tomography (CT), including cone beam computed tomography (CBCT), ultrasound, and magnetic resonance imaging (MRI). In yet other embodiments, the digital impression is generated from a physical impression by scanning the impression or plaster model of the dentition of the patient created from the physical impression. Examples of technologies for scanning a physical impression or model include three-dimensional laser scanners and computed tomography (CT) scanners. In yet other embodiments, digital impressions are created using other technologies.

The motion capture system 100 has been described previously and captures a representation of the movement of the dental arches relative to each other. In some embodiments, the motion capture station generates motion data 810.

In other embodiments, the motion capture system 100 generates motion data 810 representing the movement of the arches relative to one another. In some embodiments, the motion capture system 100 generates the motion data 810 from optical measurements of the dental arches that are captured while the dentition of the patient is moved. In some embodiments, the optical measurements are extracted from image or video data recorded while the dentition of the patient is moved. Additionally, in some embodiments, the optical measurements are captured indirectly. For example, in some embodiments, the optical measurements are extracted from images or video data of one or more devices (e.g., the patient assembly 104) that are secured to a portion of the dentition of the patient. In other embodiments, the motion data 810 is generated using other processes. Further, in some embodiments, the motion data 810 includes transformation matrices that represent the position and orientation of the dental arches. The motion data 810 may include a series of transformation matrices that represent various motions or functional paths of movement for the patient's dentition. Other embodiments of the motion data 810 are possible as well.

In some embodiments, still images are captured of the patient's dentition while the dentition of the patient is positioned in a plurality of bite locations. In some embodiments, image processing techniques are used to determine the positions of the patient's upper and lower arches relative to each other (either directly or based on the positions of the attached patient assembly 104). In some embodiments, the motion data 810 is generated by interpolating between the positions of the upper and lower arches determined from at least some of the captured images.

The motion data 810 may be captured with the patient's jaw in various static positions or moving through various motions. For example, the motion data 810 may include a static measurement representing a centric occlusion (i.e., the patient's mandible closed with teeth fully engaged) or centric relation (i.e., the patient's mandible nearly closed, just before any shift occurs that is induced by tooth engagement or contact) bite of a patient. The motion data 810 may also include static measurements or sequences of data corresponding to protrusive (i.e., the patient's mandible being shifted forward while closed), lateral excursive (i.e., the patient's mandible shifted/rotated left and right while closed), hinging (i.e., the patient's mandible opening and closing without lateral movement), chewing (i.e., the patient's mandible chewing naturally to, for example, determine the most commonly used tooth contact points), and border movements (i.e., the patient's mandible is shifted in all directions while closed, for example, to determine the full range of motion) of the patient's jaw. This motion data 810 may be used to determine properties of the patient's temporomandibular joint (TMJ). For example, hinging motion of the motion data 810 may be used to determine the location of the hinge axis of the patient's TMJ.

The example dental lab 804 includes a 3D scanner 812, a design system 816, a rapid fabrication machine 819, and an appliance fabrication station 822. Although shown as a single dental lab in this figure, in some embodiments, the dental lab 804 comprises multiple dental labs. For example, in some embodiments, the 3D scanner 812 is in a different dental lab than one or more of the other components shown in the dental lab 804. Further, in some embodiments, one or more of the components shown in the dental lab 804 are not in a dental lab. For example, in some embodiments, one or more of the 3D scanner 812, design system 816, rapid fabrication machine 819, and appliance fabrication station 822 are in the dental office 802. Additionally, some embodiments of the system 800 do not include all of the components shown in the dental lab 804.

The example 3D scanner 812 is a device configured to create a three-dimensional digital representation of the dental impression 808. In some embodiments, the 3D scanner 812 generates a point cloud, a polygonal mesh, a parametric model, or voxel data representing the dental impression 808. In some embodiments, the 3D scanner 812 generates a digital dental model 814. In some embodiments, the 3D scanner 812 comprises a laser scanner, a touch probe, or an industrial CT scanner. Yet other embodiments of the 3D scanner 812 are possible as well. Further, some embodiments of the system 800 do not include the 3D scanner 812. For example, in some embodiments of the system 800 where the dental impression station 806 generates a digital dental impression, the 3D scanner 812 is not included.

The design system 816 is a system that is configured to generate the dental appliance data 818. In some embodiments, the dental appliance data 818 is three-dimensional digital data that represents the dental appliance component 820 and is in a format suitable for fabrication using the rapid fabrication machine 819.

In some embodiments, the design system 816 comprises a computing device including user input devices. The design system 816 may include computer-aided-design (CAD) software that generates a graphical display of the dental appliance data 818 and allows an operator to interact with and manipulate the dental appliance data 818. For example, the design system 816 may include digital tools that mimic the tools used by a laboratory technician to physically design a dental appliance. For example, some embodiments include a tool to move the patient's dentition according to the motion data 810 (which may be similar to a physical articulator). Additionally, in some embodiments, the design system 816 includes a server that partially or fully automates the generation of designs of the dental appliance data 818, which may use the motion data 810.

The design system 816 may be usable to design one or more dental appliance and/or dental treatment concurrently. The motion data 810 may be used to evaluate the interaction between the one or more dental appliances and/or dental treatments. This may be particularly beneficial in designing complex appliances and planning complex dental treatments such as implant supported denture systems.

In some embodiments, the rapid fabrication machine 819 comprises one or more three-dimensional printers, such as the ProJet line of printers from 3D Systems, Inc. of Rock Hill, S.C. Another example of the rapid fabrication machine 819 is stereolithography equipment. Yet another example of the rapid fabrication machine 819 is a milling device, such as a computer numerically controlled (CNC) milling device. In some embodiments, the rapid fabrication machine 819 is configured to receive files in the STL format. Other embodiments of the rapid fabrication machine 819 are possible as well.

Additionally, in some embodiments, the rapid fabrication machine 819 is configured to use the dental appliance data 818 to fabricate the dental appliance component 820. In some embodiments, the dental appliance component 820 is a physical component that is configured to be used as part or all of the dental appliance 824. For example, in some embodiments, the dental restoration component is milled from zirconium or another material that is used directly as a dental restoration. In other embodiments, the dental appliance component 820 is a mold formed from wax or another material and is configured to be used indirectly (e.g., through a lost wax casting or ceramic pressing process) to fabricate the dental appliance 824. Further, in some embodiments, the dental appliance component 820 is formed using laser sintering technology.

In some embodiments, the appliance fabrication station 822 operates to fabricate a dental appliance 824 for the patient. In some embodiments, the appliance fabrication station 822 uses the dental appliance component 820 produced by the rapid fabrication machine 819. In some embodiments, the dental appliance 824 is a filling, partial crown, full crown, veneer, bridge, complete denture, partial denture, implant framework, surgical splint, implant guide, or orthotic splint such as a deprogramming splint or a temporomandibular disorder (TMD) splint. For example, the implant frameworks may support complete or partial dentures and may be designed using implant framework design software applications. Other embodiments of the dental appliance 824 are possible as well. In some embodiments, the dental appliance 824 is formed from an acrylic, ceramic, or metallic material. In some embodiments, the dental impression 808 is used in the fabrication of the dental appliance 824. In some embodiments, the dental impression 808 is used to form a plaster model of the dentition of the patient. Additionally, in some embodiments, a model of the dentition of the patient is generated by the rapid fabrication machine 819. In some embodiments, the appliance fabrication station 822 includes equipment and processes to perform some or all of the techniques used in traditional dental laboratories to generate dental appliances. Other embodiments of the appliance fabrication station 822 are possible as well.

In some embodiments, the dental appliance 824 is seated in the mouth of the patient in the dental therapy station 826 by a dentist. In some embodiments, the dentist confirms that the occlusal surface of the dental appliance 824 is properly defined by instructing the patient to engage in various bites. Additionally, in some embodiments, the dentist D uses the dental appliance 824 to provide a dental therapy such as orthognathic surgery or placement of one or more dental implants.

Additionally, in some embodiments, the dental office 802 is connected to the dental lab 804 via a network.

In some embodiments, the network is an electronic communication network that facilitates communication between the dental office 802 and the dental lab 804. An electronic communication network is a set of computing devices and links between the computing devices. The computing devices in the network use the links to enable communication among the computing devices in the network. The network can include routers, switches, mobile access points, bridges, hubs, intrusion detection devices, storage devices, standalone server devices, blade server devices, sensors, desktop computers, firewall devices, laptop computers, handheld computers, mobile telephones, and other types of computing devices.

In various embodiments, the network includes various types of links. For example, the network can include one or both of wired and wireless links, including Bluetooth, ultra-wideband (UWB), 802.11, ZigBee, and other types of wireless links. Furthermore, in various embodiments, the network is implemented at various scales. For example, the network can be implemented as one or more local area networks (LANs), metropolitan area networks, subnets, wide area networks (such as the Internet), or can be implemented at another scale.

Figure 16:
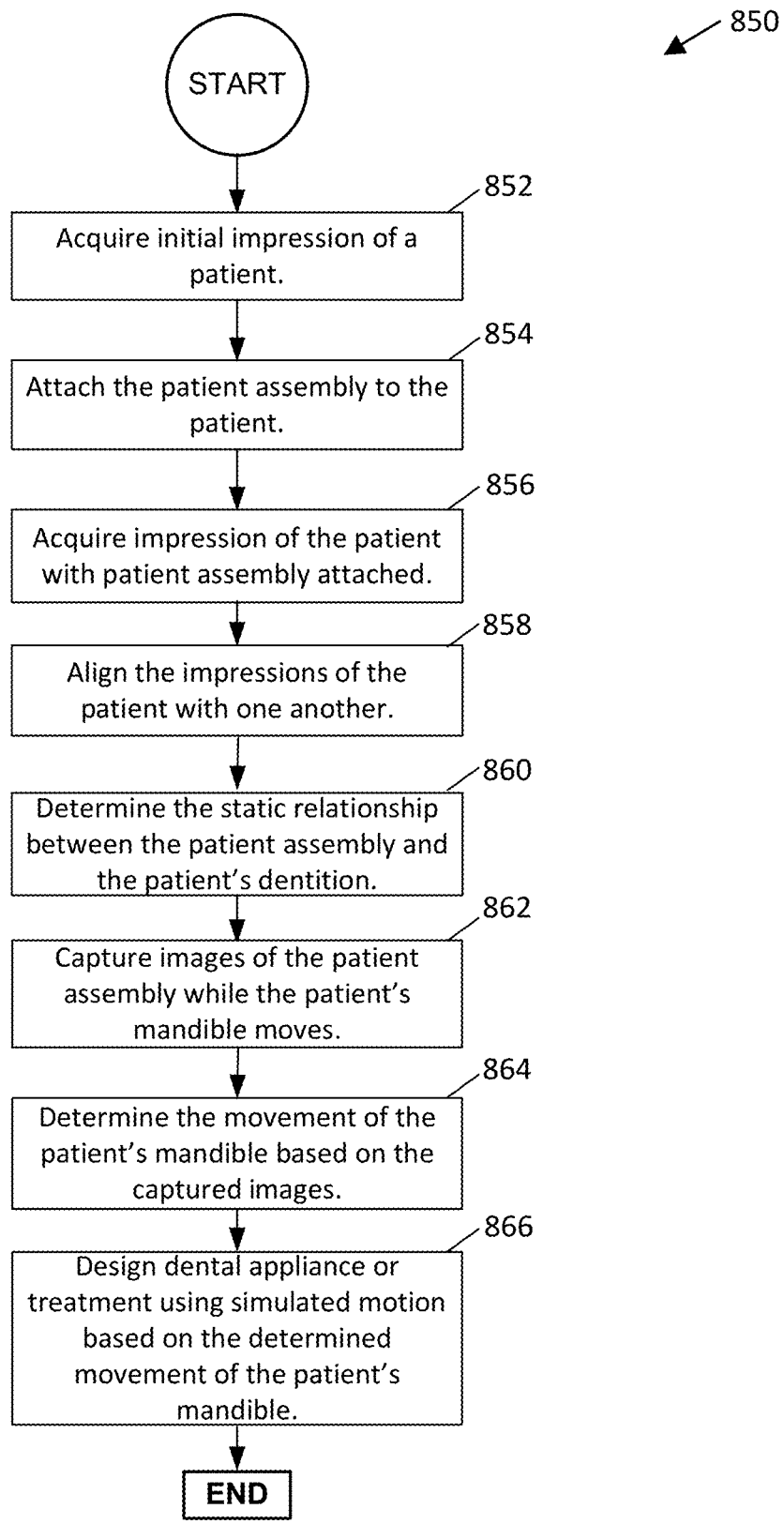
FIG. 16 is an example process for designing a dental appliance or treatment based on captured jaw motion performed by embodiments of the system of FIG. 1.

FIG. 16 is an example process 850 for designing a dental appliance or treatment based on captured jaw motion. In some embodiments, the process 850 is performed by the system 800.

At operation 852, an initial impression of a patient is acquired. In some aspects, the initial impression is captured using a digital or physical impressioning technique. Alternatively, the initial impression is acquired from a storage location such as a database that stores dental impression data (e.g., from a previous patient visit).

At operation 854, the patient assembly 104 is attached to the patient. As has been described previously, the patient assembly 104 may be attached to the patient's upper and lower dentition so as to capture relative jaw motion.

At operation 856, a second impression of the patient is captured while the patient assembly 104 is attached to the patient. As has been described previously, the patient assembly may include various internal markers (e.g., fiducial markers) the location of which may be captured in the second impression. The patient does not necessarily wear the entire patient assembly during this operation. For example, the patient may wear the dentition coupling device of the clutch and the dentition coupling device of the reference structure for the second impression. In some implementations, the second impression is captured using an intraoral scanner. The second impression may capture fiducial markers of the patient assembly 104 or other features of the patient assembly that are usable to establish a static relationship between the position indicator system 134 (and/or the position indicator system 128) of the patient assembly 104 and the patient's dentition. For example, the second impression may include a corner of a housing of the position indicator system.

At operation 858, the initial impression and the second impression are aligned with one another. Various techniques may be used to align the impressions. In some embodiments, the shape or approximate shape of the attached patient assembly is subtracted from the second impression before performing the alignment. Boolean operations may be used to subtract the shape of the attached patient assembly. The position of the patient assembly in the second impression may be determined based on the location of the fiducials in the second impression. Additionally or alternatively, only portions of the second impression that are determined to not be part of the patient assembly may be used to align the second impression to the first impression.

In some implementations, the initial impression and the second impression may be aligned in phases. For example, in a first alignment phase, the initial impression and the second impression may be approximately aligned based on an estimating orientations and identifying border points of the patient's dentition (e.g., the most anterior point in the impression and the left-most and right-most points). After the first alignment phase, the initial impression and the second impression may be roughly aligned. A second alignment phase may then be performed to refine the alignment of the initial impression and the second impression. For example, the alignment phase may include performing iterative closest point alignment on the initial impression and the second impression. Iterative closest point alignment may be performed by iteratively (e.g., repeatedly) associating selected points (e.g., vertices) from the initial impression with the closest points from the second impression, estimating a transformation (e.g., a rotation and translation) of the second impression to more closely align the associated points from the second impression the selected points from the initial impression, applying the transformation to the second impression.

At operation 860, a static relationship between the patient assembly and the patient's dentition is determined. In some embodiments, the static relationship is determined based on the alignment of the initial impression to the second impression. Alternatively or additionally, the static relationship may be determined based on the design of the patient assembly. For example, in some embodiments, the patient assembly 104 is custom fabricated to fit a patient's dentition in a particular manner. In these embodiments, when the patient assembly 104 is properly attached to the patient's dentition, the static relationship between the patient assembly and the patient's dentition can be determined based on that design. In these embodiments, it may not be necessary to capture an impression of the patient with the patient assembly attached. Additionally, in some embodiments, the static relationship between the patient assembly and the patient's dentition is determined later in the process 850 such as by capturing images of the inside of the impression device 200 after the patient assembly has been removed from the patient.

At operation 862, images are captured while the patient's mandible moves. In some embodiments, the patient's mandible is first moved in a hinge motion (e.g., opened straight up) one or more times. The patient may move his or her jaw in accord with directions from the dentist. Additionally or alternatively, the dentist may move the patient's jaw. Based on the motion data captured by the patient, the location of the screw axis of the temporomandibular joint may be determined.

In some embodiments, images are also captured while the patient's mandible is moved excursively and protrusively. Additionally, in some embodiments, images are captured while the patient engages in a chewing motion such as by chewing on a bolus of wax or a similar substance. In this manner, images are captured throughout a range of patient mandibular movements. Images may also be captured while the patient's jaw is in centric occlusion or centric relation and while the patient's jaw performs border movements.

At operation 864, the movement of the patient's mandible is determined based on the captured images. In some embodiments, the movement of the patient's mandible is determined by analyzing the captured images to determine the location of intersection points on screens in the images. Based on the determined locations of the intersection points, the relative positions and orientation of portions of the patient assembly can be determined. Using the determined static relationship between the patient assembly 104 and the patient's dentition, the position and orientation of the patient's dentition can be determined in each of the images (or sets of simultaneously captured images). Based on multiple images, the motion of the patient's mandible relative to the maxilla can be determined.

At operation 866, a dental appliance is designed or a dental treatment is planned based on digitally simulating the movement of the patient's mandible.

If desired, condyle displacement can be determined and analyzed during post processing by receiving or inferring the condyle locations relative to the patient's dentition and applying the recorded motion transformations to those condyle locations. These locations may be received via user input in a user interface. The user input may be based on clinical physical measurements. These locations may also be determined by integrating three-dimensional images of at least a portion of the patient's craniofacial anatomy that includes the condyles with the three-dimensional image of the patient's dentition.

The three-dimensional images of the patient's craniofacial anatomy may include a combination of three-dimensional surface scans of the patient's dentition, computed tomography (CT) data, cone beam computed tomography (CBCT) data, and three-dimensional photos. These three-dimensional images of the patient's craniofacial anatomy may be aligned relative to one another and the three-dimensional images of the patient's dentition by matching common surfaces that are common to multiple images. Additionally, the approximate condyle locations may be inferred based on the recorded motion when the jaw is opened and closed.

In some aspects, CBCT or CT data is captured while the patient is wearing a device that includes one or more fiducial markers. For example, the CBCT or CT data may be captured while the patient is wearing the impression device 200 (illustrated in FIG. 5) or the clutch 462 (illustrated in FIG. 8). The CBCT or CT data can then be converted to a mesh using an appropriate mesh creation algorithm such as the marching cubes algorithm. This mesh from the CBCT or CT data can then be aligned with a mesh representing an impression of the patient while the patient is wearing the impression device 200. These two meshes can be aligned using various techniques such as an iterative closest point alignment technique. Once aligned, the motion data captured while the patient was wearing the impression device 200 can be applied to the mesh of the CBCT or CT data. In this manner, the movement of the condyle can be visualized in the condyle. The combined movement data and CBCT or CT data can be used to, for example, plan implant treatments and evaluate various other types of restorations. In some embodiments, once an implant is positioned relative to the CBCT or CT data, the implant can move with the CBCT or CT data.

Although the process 850 determines the static relationship between the patient assembly and the patient's dentition before capturing images while the patient's jaw in motion, other embodiments determine the static relationship at another point in time such as after capturing images of the patient's jaw is in motion.

Figure 17:
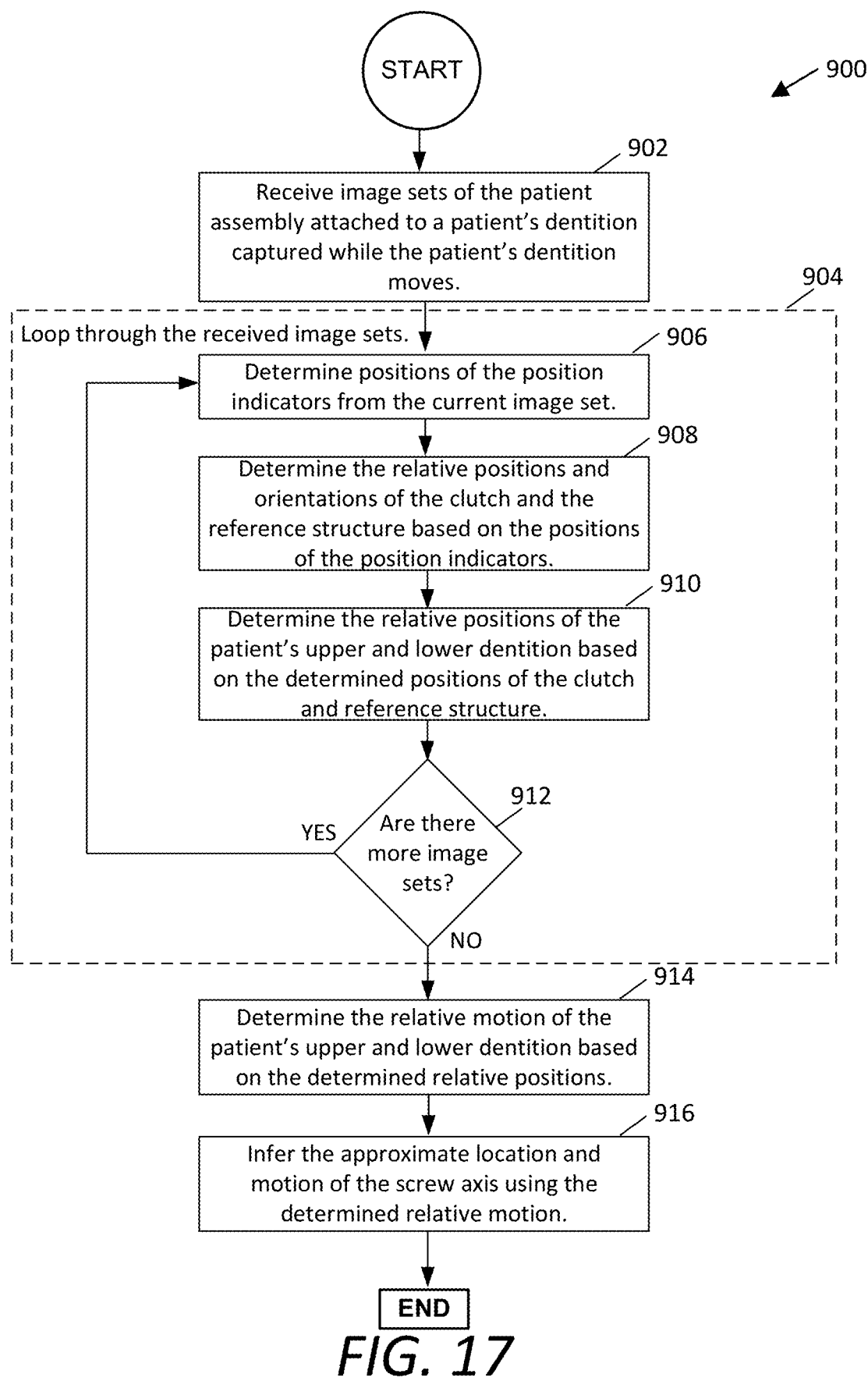
FIG. 17 is an example process for determining relative motion of the patient's upper and lower dentition based on images captured by the imaging system of FIG. 1 that is performed by embodiments of the motion determining device of FIG. 1.

FIG. 17 is an example process 900 for determining the relative motion of the patient's upper and lower dentition based on images captured by the imaging system 102. In some embodiments, the process 900 is performed by the motion determining device 106.

At operation 902, image sets of the patient assembly attached to a patient's dentition captured while the patient's dentition moves are received. In some embodiments, each of the image sets comprises a single image. In other embodiments, each of the image sets comprises multiple images that were captured simultaneously (e.g., at the same or approximately the same time) by different cameras.

At operation 904, a loop processes each of the received image sets. Within this description of the loop of operation 904, the received image set that is being processed is referred to as the current image set.

At operation 906, the positions of the position indicators are determined by processing the images in the current image set. For example, each image in the current image set may capture a different screen of the imaging system 102. For example, in an implementation with three screens, the current image set may include three images. In an implementation with two screens, the current image set may include two images. The locations within the images where light projected by the patient assembly 104 intersects the screens may be determined based, for example, on color, intensity, or contrast values. Each image may include one or more points of intersection. For example, a single image may include an intersection point from a clutch and from a reference structure. In implementations with fewer than three screens, a single image may include even more intersection points. In some embodiments, a color of the intersection point is analyzed to determine whether the light beam was emitted by a light emitter of the clutch or reference structure. Additionally, the position of the intersection point may be used to distinguish between intersection points from light emitters on the clutch and intersection points on the reference structure. Similarly, positions of the intersection points may be used to distinguish between intersection points from different light emitters of the same clutch or reference structure.

In some implementations, the position and orientation of a clutch is determined based on mapping the two-dimensional coordinates of the points of intersection in the images to three-dimensional coordinates with respect to the screen assembly. This mapping can be performed because each of the screen are positioned at a known position with respect to the screen framework. A plane can then be identified using three of the three-dimensional coordinates of intersection points from a specific light emitter (e.g., a light emitter of the clutch or of the reference structure). Then, a line on the plane can be defined based on the intersection points of the collinear light beams (e.g., light beams L1 and L2 of the clutch or light beams L4 and L5 of the reference structure). Then, an intersection point can be found between the line and the remaining light beam using the offset angle compensation factor. That intersection point will be at a known position with respect to the light emitter, which itself is at a known position with respect to the patient's dentition.

Additionally, a coordinate system for the light emitter can be determined based on three intersection points of the light beams. A first axis of the coordinate system can be defined based on the line between the collinear light beams (this axis will roughly correspond to the left-right axis with respect to the patient). A second axis of the coordinate system can be defined based on the cross-product of the first axis and a vector between either of the intersection points of the collinear light beams and the intersection point of the other light beam (this axis will be normal to the plane identified from the intersection points and roughly correspond to the up-down axis with respect to the patient). A third axis of the coordinate system can be defined based on the cross-product of the first axis and the second axis (this axis will roughly correspond to the anterior-posterior or front-to-back axis with respect to the patient).

At operation 908, the relative positions and orientations of the clutch and the reference structure are determined based on the positions of the position indicators. As described previously, based on determining the intersection points of the light beams with the screens, the relative position and orientation of the clutch relative to the reference structure can be determined.

At operation 910, the relative positions of the patient's upper and lower dentition are determined based on the determined positions of the clutch and reference structure. In some embodiments, the relative positions are determined based on information about the static relationship between the patient assembly and the patient's dentition.

At operation 912, it is determined whether there are more image sets to process through the loop. If so, the process 900 returns to operation 906 to process the next image set. If not, the process continues to operation 914.

At operation 914, the relative motion of the patient's upper and lower dentition is determined based on the determined relative positions in the image sets. In some embodiments, a series of transformation matrixes are generated that correspond to the relative movement of the patient's lower dentition relative to the upper dentition in each of the image sets. This series of transformation matrixes can then be sequentially applied to a digital model of the patient's lower dentition to cause the lower dentition to digitally move in accordance with the captured motion. In this manner, the motion data is used as a digital articulator.

At operation 916, the approximate location and motion of the screw axis (or hinge axis) of the patient's TMJ is inferred using the determined relative motion. In some embodiments, at least a portion of the image sets is captured while the patient's mandible is moving in a hinge motion (i.e., simply opening and closing without any excursive or protrusive movement). These image sets may be labeled, stored separately, or otherwise distinguished from the other image sets. The motion data for the image sets corresponding to this hinge movement can be analyzed to determine the approximate location of the screw axis. For example, the motion data can be fit to a circular arc. The location of the center of the circular arc can then be determined. In some embodiments, it is then determined that the screw axis passes through the center of the circle along a line that is orthogonal to the plane of the circular arc. Once the screw axis is inferred, the movement of the screw axis can be inferred as well. The relative motion data for the mandible relative to the maxilla can be applied to the screw axis to determine the movement of the screw axis.

Figure 18:
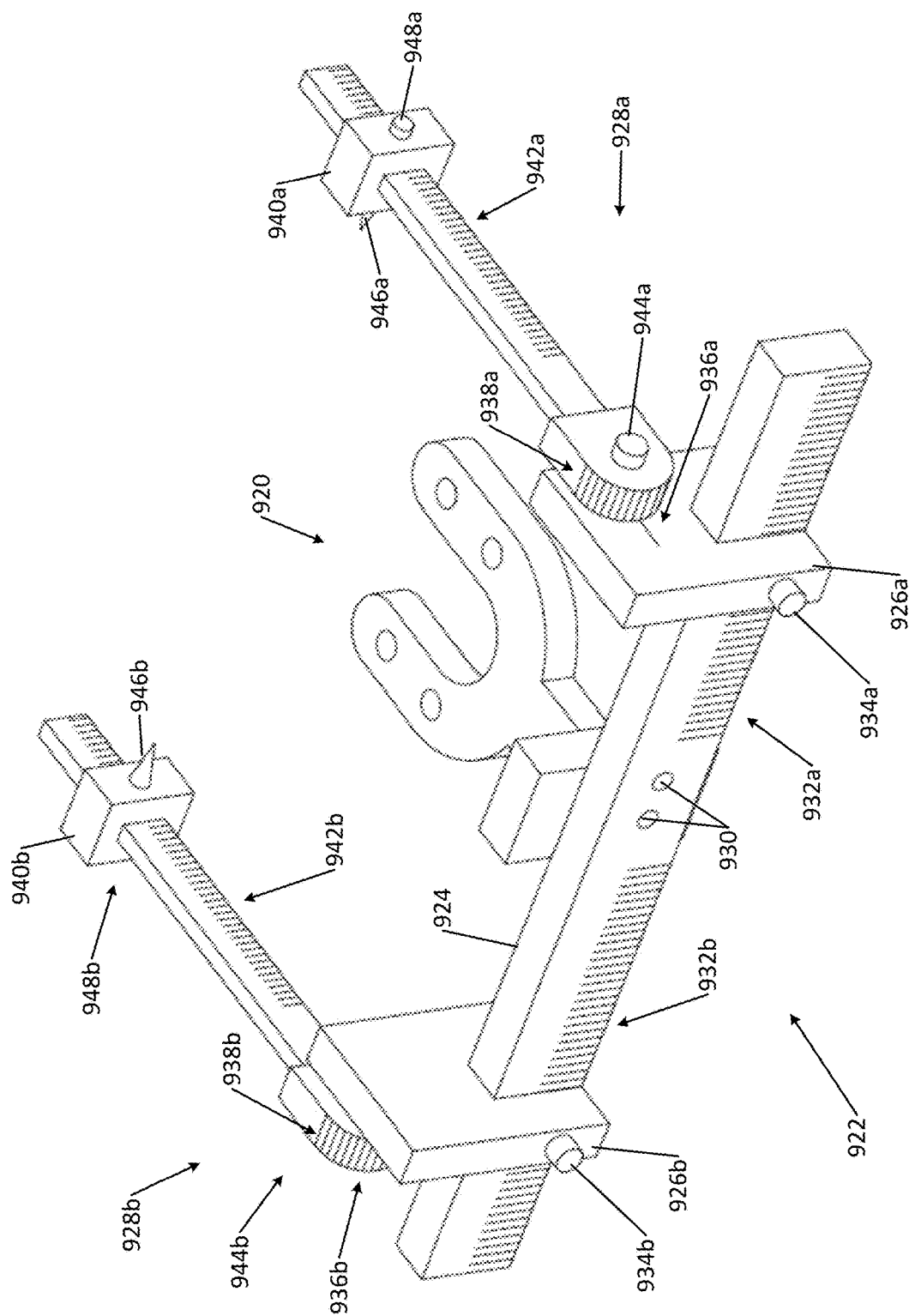
FIG. 18 illustrates an example transfer assembly usable with embodiments of a clutch of the patient assembly of FIG. 1.

FIG. 18 illustrates an example clutch 920 and an example transfer assembly 922. The clutch 920 is example of a clutch such as the clutch 462 shown in FIG. 8. The clutch 920 may include fiducial markers similar to the internal fiducial markers 466.

The transfer assembly 922 is usable to transfer coordinate information to a physical articulator. The coordinate information may be digitally derived based on the movement data and/or the inferred screw axis location. For example, the transfer assembly 922 may be usable to position the clutch 920 relative to a physical articulator in a position that allows the physical articulator to closely match the movement derived using the system 100.

The transfer assembly 922 includes a main body 924, sliding blocks 926a, 926b, and pivot arms 928a, 928b. The main body 924 is usable to adjust the width of the transfer assembly 922. The main body 924 may be a horizontally aligned linear body. The main body 924 includes a mounting assembly 930 and translation markings 932a, 932b. The mounting assembly 930 is usable to mount the clutch 920 to the transfer assembly 922. In some embodiments, the mounting assembly 930 comprises one or more apertures through which pins or keyed pins of the clutch 920 can removably fit to mount the clutch 920 to the transfer assembly 922. Typically, the mounting assembly is configured to mount the clutch 920 in a precise known relationship to the transfer assembly 922.

The translation markings 932a, 932b comprise a series of markings to indicate the width of the transfer assembly 922. In various embodiments, the translation markings 932a, 932b are disposed at different locations. For example, the translation markings 932a, 932b may each include a plurality of markings at 1 mm intervals. Other distances are possible too.

The sliding blocks 926a, 926b slide along the main body 924 to define the width of the transfer assembly 922. In some embodiments, the sliding blocks 926a, 926b include locking assemblies 934a, 934b and alignment indicators 936a, 936b. Although alternatives are possible, the sliding blocks 926a, 926b typically move independently of each other. In use, the sliding blocks 926a, 926b slide along the main body 924 to a specified position, which can be determined with reference to the translation markings 932a, 932b. In this manner, the sliding blocks 926a, 926b define the width of the transfer assembly 922. In some embodiments, the sliding blocks 926a, 926b include locking assemblies 934a, 934b to lock the sliding blocks 926a, 926b in a position relative to the translation markings 932a, 932b. In some embodiments, the locking assemblies 934a, 934b comprise one or more knobs or thumb screws.

The alignment indicators 936a, 936b are usable to indicate the rotational position of the pivot arms 928a, 928b. In some embodiments, the alignment indicators 936a, 936b each comprise a single line to mark a place by which the rotation of the pivot arms 928a, 928b can be compared.

The pivot arms 928a, 928b rotate to adjust the position of the transfer assembly 922. Although alternatives are possible, in this example, the pivot arms are rotatably connected to the sliding blocks 926a, 926b. In some embodiments, the pivot arms 928a, 928b include angle markings 938a, 938b, sliding blocks 940a, 940b, translation markings 942a, 942b, and locking assemblies 944a, 944b.

In this example, the angle markings 938a, 938b are disposed on a rounded end of the pivot arm. The angle markings 938a, 938b rotate with the pivot arm. The angle markings 938a, 938b can then be compared to the alignment indicators 936a, 936b to determine the rotation of the pivot arms 928a, 928b relative to the sliding blocks 926a, 926b (and therefore to the main body 924). Once the pivot arms 928a, 928b are rotated to a specified position, the locking assemblies 944a, 944b can be used to lock the rotation of the pivot arms 928a, 928b. The locking assemblies 944a, 944b may be similar to the locking assemblies 934a, 934b.

The sliding blocks 940a, 940b slide along the pivot arms 928a, 928b to adjust the depth of the transfer assembly 922. As mentioned above, the pivot arms 928a, 928b include translation markings 942a, 942b, which can be used as a reference in aligning the sliding blocks 940a, 940b at a specified distance from the main body 924. The translation markings 942a, 942b may be similar to the translation markings 932a, 932b.

In some embodiments, the sliding blocks 940a, 940b include articulator couplers 946a, 946b and locking assemblies 948a, 948b. The articulator couplers 946a, 946b are configured to mate with a feature of a target articulator. Depending on the target articulator, the articulator couplers 946a, 946b will have different forms.

The locking assemblies 948a, 948b are configured to lock the sliding blocks 940a, 940b at a specified position along the pivot arms 928a, 928b. The locking assemblies 948a, 948b may be similar to the locking assemblies 934a, 934b.

In some embodiments, the motion determining device 106 or another component of the system 100 determines parameters for the transfer assembly 922. Examples parameters include the positions of the sliding blocks 926a, 926b relative to the translation markings 932a, 932b; the rotation of the pivot arms 928a, 928b relative to the sliding blocks 926a, 926b, which can be evaluated with reference to the angle markings 938a, 938b and the alignment indicators 936a, 936b; and the positions of the sliding blocks 940a, 940b relative to the translation markings 942a, 942b. These parameter settings can be displayed on a display device of a computing device, printed on a report, or otherwise communicated to a user. The user can then adjust the transfer assembly 922 to match the specified settings. Once setup, the transfer assembly can be used to mount a stone model of the upper dentition to an articulator at the position associated with the specified settings. A stone model of the lower dentition can then be mounted relative to the stone model of the upper dentition (e.g., using a bite record). In this manner, the transfer assembly 922 can be used to mount stone models of the dentition on an articulator so as to match the movement data captured using the system 100.

In some embodiments of the transfer assembly 922, some or all of the translation markings 932a, 932b, 942a, 942b and angle markings 938a, 938b are replaced with digital readouts that are based on linear and/or rotary encoders.

Figure 19:
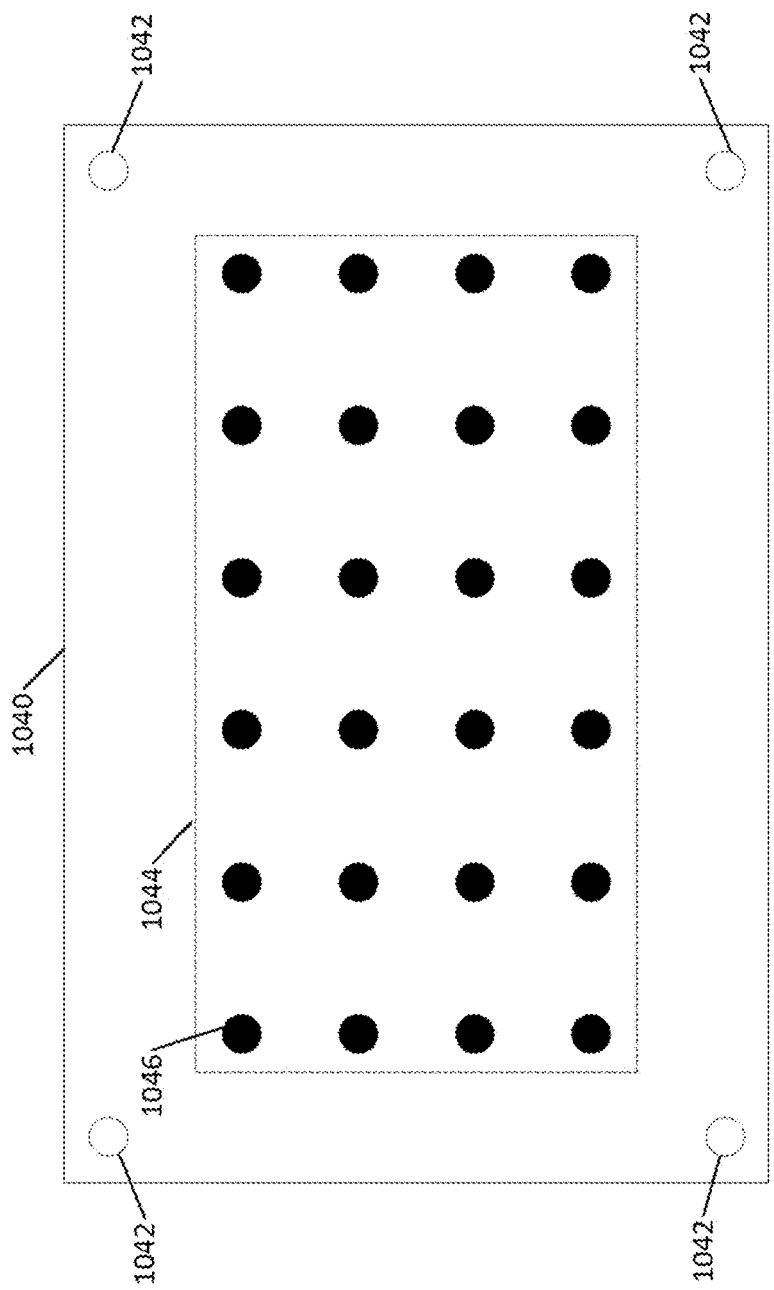
FIG. 19 illustrates a calibration plate usable with embodiments of the system of FIG. 1.

FIG. 19 illustrates a calibration assembly 1040 that is usable with embodiments of the system of FIG. 1. The calibration assembly 1040 is used to calibrate the image coordinates of images captured by the imaging system 102 to real-world coordinates on the screens 438. Once the system 100 has been calibrated, the pixels in the images captured by the cameras 420 can be mapped to real-world coordinates on the screens 438. For example, the real-world coordinates of the intersection points on the screens 438 of the light beams emitted by the light source assembly 404 can be determined based on the pixel of the images that includes the light beam.

In some embodiments, the calibration assembly 1040 is configured to attach to the screen framework 436. After the calibration assembly 1040 is attached, a calibration image is captured by at least one of the cameras 420. The calibration assembly 1040 includes a calibration region 1044. In some embodiments, the calibration region 1044 includes a plurality of markings 1046 disposed at known positions. In this example, the calibration region 1044 includes four rows of six markings 1046. Other embodiments include different numbers of and arrangements of markings 1046. For example, some embodiments include ten rows of thirteen markings 1046. In some embodiments, the calibration region 1044 is sized to cover the portion of the screen in which light beams are expected to intersect.

In some embodiments, the markings 1046 are configured to be identifiable in images of the calibration assembly 1040. Although alternatives are possible, in this example, the markings 1046 are dots that contrast with the rest of the calibration region 1044. For example, the markings 1046 can be black over a white background. The markings 1046 have known dimensions and positions. For example, in some embodiments, the markings 1046 are round circles having a known diameter (e.g., five millimeters) and known spacing (e.g., spaced apart by twenty millimeters). In some embodiments, the positions are known relative to each other. In some embodiments, the positions are known relative to the screen framework 436 when the calibration assembly 1040 is attached. In some embodiments, the markings 1046 include raised or indented portions. In these embodiments, a coordinate measurement system can identify the markings 1046 and measure the locations of the markings 1046.

In some embodiments, image processing techniques are used to determine the pixel coordinates of the centers of the markings 1046 in a calibration image captured by one of the cameras 420. For example, a circle can be best fit to each of the contrasting regions in the image. The pixel corresponding to the center point of each of the circles can then be determined. In some embodiments, a map is then built to map from the determined center points to real-world positions based on the known information about the calibration markings.

In some embodiments, the calibration region 1044 includes calibration markings that are lines that form a grid pattern or squares that form a checkerboard pattern. Other arrangements of the calibration region are possible as well.

The calibration assembly 1040 also includes an attachment assembly 1042. The attachment assembly 1042 is a physical structure that is configured to removably couple the calibration assembly 1040 to the screen framework 436. In this example, the attachment assembly 1042 includes a plurality of apertures through which fasteners can be used to attach the calibration assembly 1040 to the screen framework 436. Examples of fasteners include bolts, such as shoulder bolts, and screws. In some embodiments, the screen framework 436 includes registration structures (e.g., pegs) that are configured to mate with the attachment assembly 1042 to attach the calibration assembly 1040 to the screen framework 436. In at least some embodiments, the calibration region 1044 is disposed at a known distance from an edge or other landmark of the calibration assembly 1040. In this manner, when the calibration assembly 1040 is registered to the screen framework 436, the position of the calibration region 1044 (and the markings 1046 therein) can be determined relative to the screen framework 436.

In some embodiments, the screens 438 are configured to be removed from the screen framework 436 by a user (e.g., the screens 438 can also include attachment assemblies that are similar to the attachment assembly 1042). In some embodiments, the screens 438 are removed from the screen framework 436 and replaced by the calibration assembly 1040 during a calibration process. In some embodiments, the calibration assembly 1040 is attached to the screen framework 436 between the cameras 420 and the screens 438. In some embodiments, the calibration assembly 1040 is attached to the screen framework 436 so that one of the screens 438 is disposed between the calibration assembly 1040 and one of the cameras 420. In these embodiments, the calibration images of the calibration assembly 1040 are captured through the screens 438.

Figure 20:
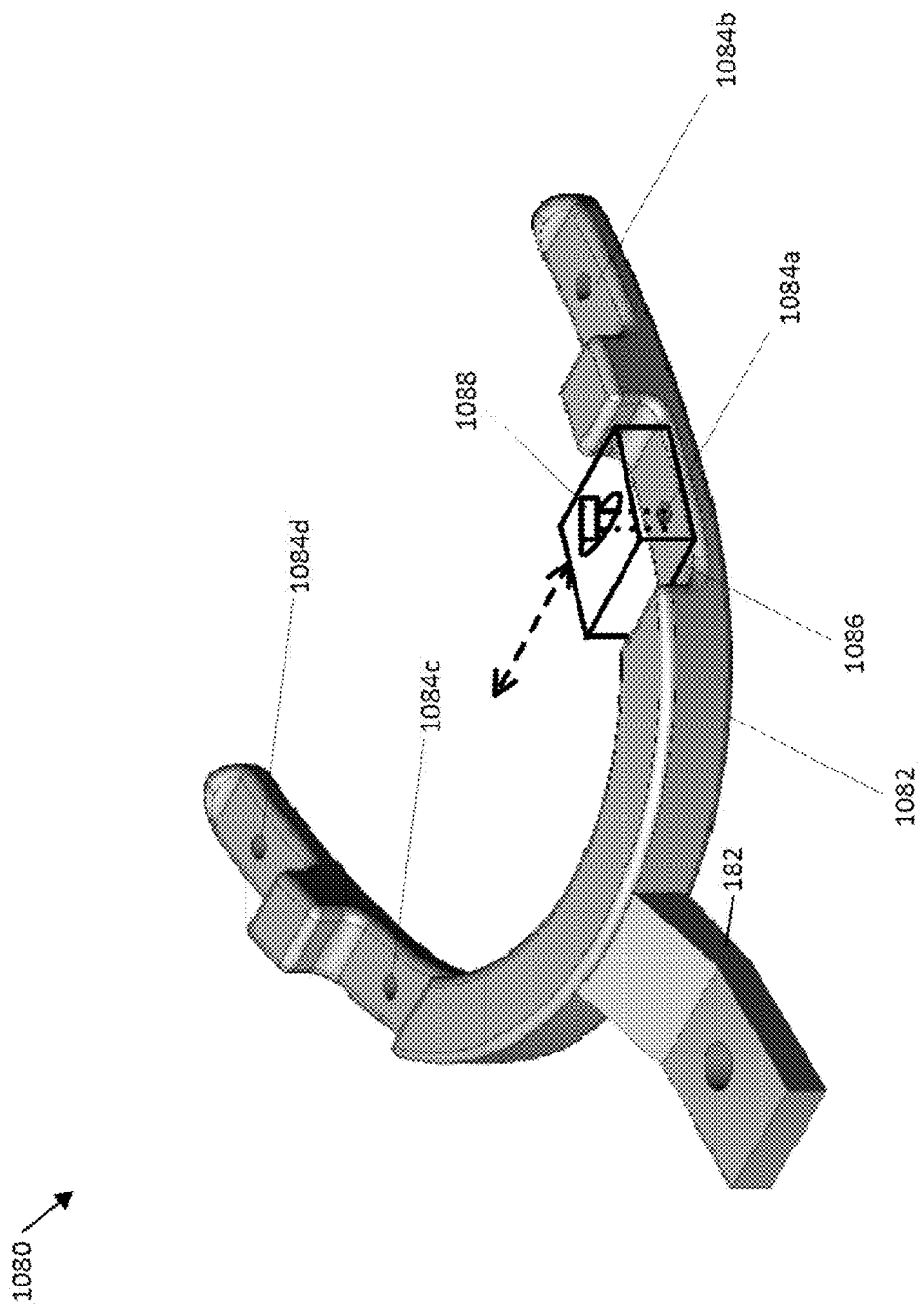
FIG. 20 illustrates an example embodiment of a dentition coupling framework of the clutch or reference structure of FIG. 2.

FIG. 20 illustrates an example embodiment of a dentition coupling device 1080 such as the dentition coupling device 124 or the dentition coupling device 130.

The dentition coupling device 1080 couples to a patient's dentition. In some embodiments, the dentition coupling device 1080 includes the extension member 182, an arch portion 1082, a plurality of apertures 1084*a*, 1084*b*, 1084*c*, and 1084*d*, an adjustable block 1086, and a fastener 1088. The extension member 182 has been previously described.

The arch portion 1082 is shaped to approximate the dental arch of a patient and is sized to fit around the outside of the patient's dentition. For example, in some embodiments, the arch portion 1082 is sized to fit around the buccal surfaces of at least a portion of the patient's dentition. The arch portion includes multiple recesses that include the apertures 1084*a*, 1084*b*, 1084*c*, and 1084*d*. In this example, there are four recesses, each having one aperture. However, other embodiments include different numbers of recesses and/or apertures.

At least some of the recesses include an adjustable block such as the adjustable block 1086. Although only one adjustable block is shown in this figure, some embodiments include more than one adjustable block. For example, in some embodiments, there is one adjustable block for each recess. The position of the adjustable block 1086 can be adjusted relative to the arch portion 1082 so that a surface of the adjustable block 1086 contacts the buccal or labial surfaces of a portion of the patient's dentition. In some embodiments, the adjustable block is secured in contact with the patient's dentition using fastener 1088. The adjustable block 1086 may include a slot that receives the fastener 1088 and allows for sliding movement of the adjustable block 1086 until the fastener is fully engaged. In some embodiments, the adjustable blocks are positioned and then adhered to the patient's dentition using an adhesive material such as a light-cured bonding agent. In this manner, the dentition coupling device 1080 can be coupled to the patient's dentition. Beneficially, the dentition coupling device 1080 can be reused with multiple patients after sufficient cleaning and sterilization.

Figure 21:
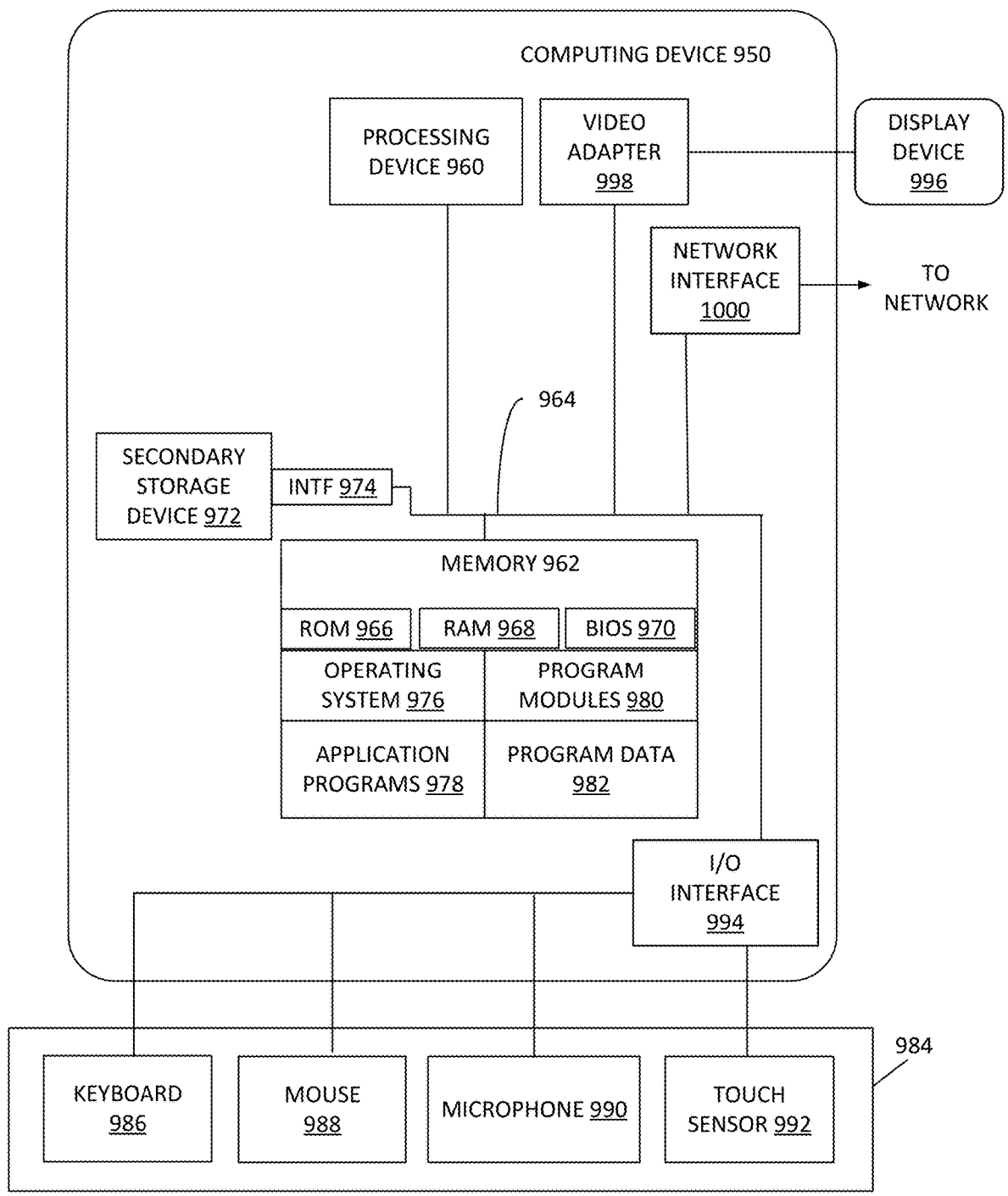
FIG. 21 illustrates an example architecture of a computing device, which can be used to implement aspects according to the present disclosure.

FIG. 21 illustrates an example architecture of a computing device 950 that can be used to implement aspects of the present disclosure, including any of the plurality of computing devices described herein, such as a computing device of the motion determining device 106, the design system 816, or any other computing devices that may be utilized in the various possible embodiments.

The computing device illustrated in FIG. 21 can be used to execute the operating system, application programs, and software modules described herein.

The computing device 950 includes, in some embodiments, at least one processing device 960, such as a central processing unit (CPU). A variety of processing devices are available from a variety of manufacturers, for example, Intel or Advanced Micro Devices. In this example, the computing device 950 also includes a system memory 962, and a system bus 964 that couples various system components including the system memory 962 to the processing device 960. The system bus 964 is one of any number of types of bus structures including a memory bus, or memory controller; a peripheral bus; and a local bus using any of a variety of bus architectures.

Examples of computing devices suitable for the computing device 950 include a desktop computer, a laptop computer, a tablet computer, a mobile computing device (such as a smart phone, an iPod® or iPad® mobile digital device, or other mobile devices), or other devices configured to process digital instructions.

The system memory 962 includes read only memory 966 and random-access memory 968. A basic input/output system 970 containing the basic routines that act to transfer information within computing device 950, such as during start up, is typically stored in the read only memory 966.

The computing device 950 also includes a secondary storage device 972 in some embodiments, such as a hard disk drive, for storing digital data. The secondary storage device 972 is connected to the system bus 964 by a secondary storage interface 974. The secondary storage devices 972 and their associated computer readable media provide non-volatile storage of computer readable instructions (including application programs and program modules), data structures, and other data for the computing device 950.

Although the example environment described herein employs a hard disk drive as a secondary storage device, other types of computer readable storage media are used in other embodiments. Examples of these other types of computer readable storage media include magnetic cassettes, flash memory cards, digital video disks, Bernoulli cartridges, compact disc read only memories, digital versatile disk read only memories, random access memories, or read only memories. Some embodiments include non-transitory computer-readable media. Additionally, such computer readable storage media can include local storage or cloud-based storage.

A number of program modules can be stored in secondary storage device 972 or system memory 962, including an operating system 976, one or more application programs 978, other program modules 980 (such as the software engines described herein), and program data 982. The computing device 950 can utilize any suitable operating system, such as Microsoft Windows™, Google Chrome™ OS or Android, Apple OS, Unix, or Linux and variants and any other operating system suitable for a computing device. Other examples can include Microsoft, Google, or Apple operating systems, or any other suitable operating system used in tablet computing devices.

In some embodiments, a user provides inputs to the computing device 950 through one or more input devices 984. Examples of input devices 984 include a keyboard 986, mouse 988, microphone 990, and touch sensor 992 (such as a touchpad or touch sensitive display). Other embodiments include other input devices 984. The input devices are often connected to the processing device 960 through an input/output interface 994 that is coupled to the system bus 964. These input devices 984 can be connected by any number of input/output interfaces, such as a parallel port, serial port, game port, or a universal serial bus. Wireless communication between input devices and the interface 994 is possible as well, and includes infrared, BLUETOOTH® wireless technology, 802.11a/b/g/n, cellular, ultra-wideband (UWB), ZigBee, or other radio frequency communication systems in some possible embodiments.

In this example embodiment, a display device 996, such as a monitor, liquid crystal display device, projector, or touch sensitive display device, is also connected to the system bus 964 via an interface, such as a video adapter 998. In addition to the display device 996, the computing device 950 can include various other peripheral devices (not shown), such as speakers or a printer.

When used in a local area networking environment or a wide area networking environment (such as the Internet), the computing device 950 is typically connected to the network through a network interface 1000, such as an Ethernet interface or WiFi interface. Other possible embodiments use other communication devices. For example, some embodiments of the computing device 950 include a modem for communicating across the network.

The computing device 950 typically includes at least some form of computer readable media. Computer readable media includes any available media that can be accessed by the computing device 950. By way of example, computer readable media include computer readable storage media and computer readable communication media.

Computer readable storage media includes volatile and nonvolatile, removable and non-removable media implemented in any device configured to store information such as computer readable instructions, data structures, program modules or other data. Computer readable storage media includes, but is not limited to, random access memory, read only memory, electrically erasable programmable read only memory, flash memory or other memory technology, compact disc read only memory, digital versatile disks or other optical storage, magnetic cassettes, magnetic tape, magnetic disk storage or other magnetic storage devices, or any other medium that can be used to store the desired information and that can be accessed by the computing device 950.

Computer readable communication media typically embodies computer readable instructions, data structures, program modules or other data in a modulated data signal such as a carrier wave or other transport mechanism and includes any information delivery media. The term "modulated data signal" refers to a signal that has one or more of its characteristics set or changed in such a manner as to encode information in the signal. By way of example, computer readable communication media includes wired media such as a wired network or direct-wired connection, and wireless media such as acoustic, radio frequency, infrared, and other wireless media. Combinations of any of the above are also included within the scope of computer readable media.

The computing device illustrated in FIG. 21 is also an example of programmable electronics, which may include one or more such computing devices, and when multiple computing devices are included, such computing devices can be coupled together with a suitable data communication network so as to collectively perform the various functions, methods, or operations disclosed herein.

In a non-limiting example, a clutch is attached to a light emitter assembly (or projector) that projects three laser beams. Two of the laser beams are co-linear and project in opposite directions. The third laser beam is perpendicular to the first two laser beams. All three laser beams are co-planar. A clutch and light emitter assembly is attached to each arch of the patient's dentition. The light emitters project laser dots onto three translucent screens such that one upper arch and one lower arch laser dot appears on each screen. Each screen is viewed by a separate video camera. The cameras are synchronized such that they capture frames simultaneously or nearly simultaneously. In some embodiments, the cameras include a synchronization input port and the system includes a synchronization system that is configured to simultaneously transmit a signal to the synchronization input port of each of the cameras, causing the cameras to begin to capture video synchronously.

In some embodiments, variations in the alignment of the screens to each other and the cameras is compensated for in software. Camera field-of-view distortion may also be compensated for in software. The upper arch dot is distinguished from the lower arch dot on each screen using one or more of the following techniques: upper arch dots are assumed to be those highest on the screens and lower arch dots are assumed to be those lowest on the screens; upper arch dots are projected in one color and lower arch dots are projected in a different color; and dots are pulsed such that upper arch dots are projected and imaged after which lower arch dots are projected and imaged. Other implementations are possible too.

An example motion capture system (or motion mapping device) may include two small laser projectors that are temporarily attached to a patient's upper and lower dentition via disposable clutches for the duration of a recording. The projectors are example of the position indicator system. Each projector projects laser spots onto two translucent screens mounted in a frame that is external to the patient. The laser spots are examples of intersection points. The frame with the screens mounted therein is an example of a screen assembly. Cameras mounted inside the external frame track the position of the laser spots. The cameras are an example of an optical sensing assembly. These laser spot locations are then used to construct a three-dimensional coordinate system for each projector. Each three-dimensional coordinate system, updated for each new video frame, is used to animate a three-dimensional full arch digital model previously obtained from a three-dimensional intra-oral scanner or physical impression.

To optimize accuracy, a unique field-of-view (FOV) calibration may be done for each camera lens to correct lens distortion. A unique calibration may also be done for the frame of the screen assembly to correct mechanical errors. The use of two projectors allows the system to accurately report the position and orientation differences between the two projectors. This, in turn, allows a patient's head to move during a recording without affecting the relative motion recorded between the patient's upper and lower arches.

Figure 22:
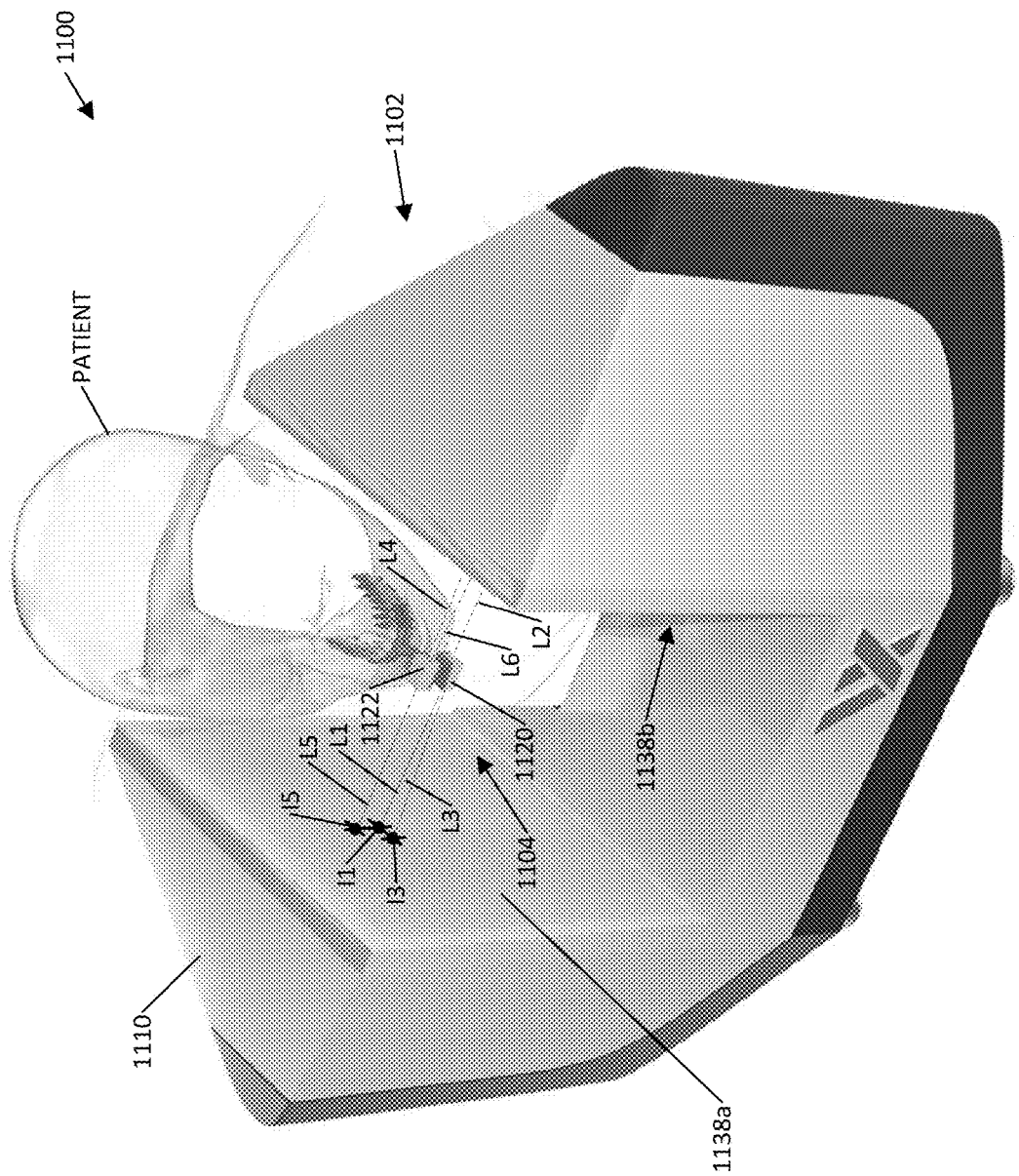
FIG. 22 includes an example of the motion capture system of FIG. 1 in which two screens are used.

FIG. 22 illustrates an implementation of a motion capture system 1100 for capturing jaw movement in which only two screens are used. The motion capture system 1100 is an example of the system 100. The motion capture system 1100 includes an imaging system 1102 and a patient assembly 1104. In this example, the imaging system 1102 includes a housing 1110. The imaging system also includes screen 1138a and a screen 1138b (collectively referred to as screens 1138), which are positioned so as to be on opposite sides of the patient's face (e.g., screen 1138b to the left of the patient's face and screen 1138a to the right of the patient's face). In some implementations, a screen framework is disposed within the housing 1110 to position the screens 1138 with respect to each other and the housing 1110.

As can be seen in FIG. 22, this implementation does not include a screen disposed in front of the patient's face. Beneficially, by not having a screen in front of a patient's face, the system 1100 which may allow better access to the patient's face by a caregiver. Also shown, is patient assembly 1104 of the motion capture system 1100.

In at least some implementations, the patient assembly 1104 includes a clutch 1120 and a reference structure 1122, each of which include a light source assembly having three light emitters. The clutch 1120 is an example of the clutch 120 and the reference structure 1122 is an example of the reference structure 122. In FIG. 22, the clutch 1120 is attached to the patient's mandible (i.e., lower dentition) and is emitting light beams L1, L2, and L3. Light beams L1 and L3 are directed toward the screen 1138a, intersecting at intersection points I1 and I3, respectively. Light beam L2 is directed toward the screen 1138b. Although alternatives are possible, in this example, the light beams L1 and L3 are offset from each other by approximately 15 degrees. The light beams L1 and L2 are collinear and directed in opposite directions (i.e., L2 is offset from L1 by 180 degrees).

The reference structure 1122 is attached to the patient's maxilla (i.e., upper dentition) and is emitting light beams L4, L5, and L6. Light beams L4 and L6 are directed toward the screen 1138b. Light beam L5 is directed toward the screen 1138a, intersecting at intersection point I5. Although alternatives are possible, in this example, the light beams L4 and L6 are offset from each other by approximately 15 degrees. The light beams L4 and L5 are collinear and directed in opposite directions (i.e., L4 is offset from L5 by 180 degrees).

As the patient's dentition moves around, the clutch 1120 and the reference structure 1122 will move in concert with the patient's dentition, causing the lights beams to move and the intersection points to change. An optical sensing assembly of the motion capture system 1100 (e.g., cameras embedded within the housing 1110 of the system 1100 behind the screens 1138a and 1138b) may capture images of the screens 1138 so that the intersection points can be determined. The location of a first axis associated with the clutch 1120 may be identified based on the intersection points from the light beams L1 and L2. An intersection coordinate between the light beams L1 and L3 may then be determined based on the distance between the intersection points I1 and I3 on the screen 1138a. For example, the distance from the intersection point I1 along the first axis can be determined based on the distance between the points I1 and I3 and the angle between I1 and I3. As described in more detail elsewhere herein, the angle between I1 and I3 is determined for the clutch 1120 and may be stored in a data store, for example, on a non-transitory computer-readable storage medium. Using this distance, the intersection coordinate can be found, which will have a known relationship to the clutch 1120 and therefore the patient's dentition. As has been described earlier, a coordinate system for the clutch 1120 can be determined based on the intersection points too (e.g., a second axis is defined by the cross product of the first axis and a vector between the intersection points I1 and I3, and a third axis is defined by the cross product of the first axis and the second axis). In a similar manner, the position and orientation of the reference structure 1122 can be determined based on the intersection points of the light beams L4, L5, and L6 with the screens 1138a and 1138b.

In some implementations, three-dimensional coordinate systems for the clutch and the reference structure are determined using only two screens. In some implementations, the motion capture system includes only two screens and the motion capture system does not include a third screen. In some implementations, the imaging system captures images of only two screens. Some implementations identify intersection points using images captured of only two screens. For example, two intersection points from light beams emitted by a reference structure are identified on an image of the same screen.

In some implementations, a light emitter being oriented to emit light in a first direction toward the screen means the light emitter is oriented to emit light in a first direction toward the screen when the light emitter is attached to a patient (or other structure) and positioned for motion tracking with respect to the imaging system.

Figure 23:
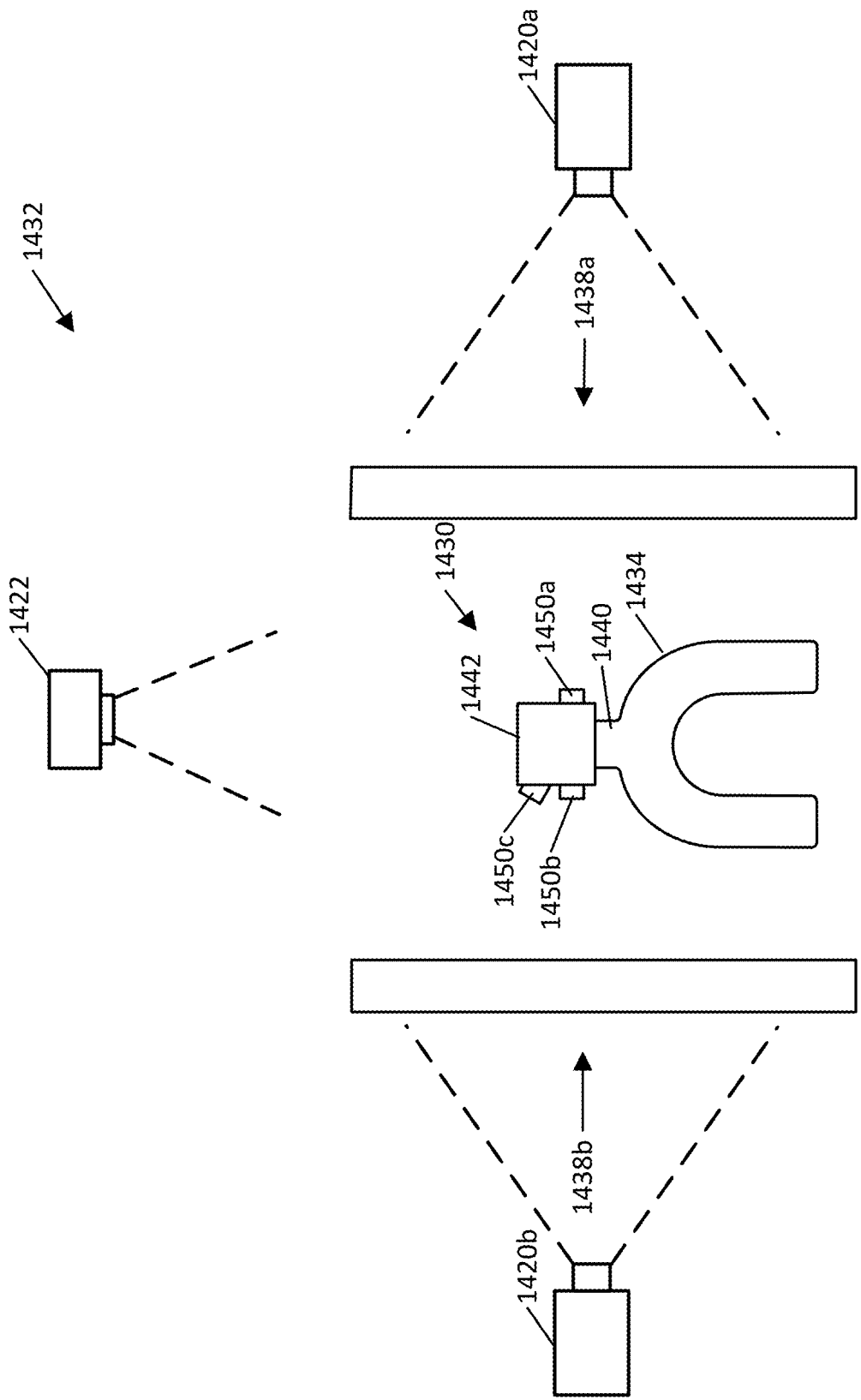
FIG. 23 illustrates a top view of an embodiment of the reference structure of FIG. 22 and an embodiment of the imaging system of FIG. 1.

FIG. 23 illustrates a top view of an embodiment of a reference structure 1430 and an embodiment of an imaging system 1432. The reference structure 1430 is an example of the reference structure 1122. The imaging system 1432 is an example of the imaging system 1102.

The reference structure 1430 includes a dentition coupling device 1434, an extension member 1440, and a light source assembly 1442. The dentition coupling device 1434 is an example of the dentition coupling device 130 and may be similar to the example dentition coupling devices previously described with respect to embodiments of the clutch. The light source assembly 1442 is an example of the position indicator system 134. In this example, the light source assembly 1442 includes light emitters 1450a, 1450b, and 1450c (collectively referred to as light emitters 1450).

The dentition coupling device 1434 is configured to removably couple to the dentition of the patient. The dentition coupling device 1434 is coupled to the opposite arch of the patient's dentition as the clutch (e.g., the dentition coupling device 1434 couples to the maxillary arch when the clutch 1400 is coupled to the mandibular arch). In some embodiments, the dentition coupling device 1434 is coupled to the extension member 1440 that is configured to extend out through the patient's mouth when the dentition coupling device 1434 is coupled to the patient's dentition. The extension member 1440 may be similar to the extension member 408.

The imaging system 1432 includes screens 1438a and 1438b (referred to collectively as screens 1438), and cameras 1420a and 1420b (referred to collectively as cameras 1420). Also shown is a patient camera 1422, which may be included in some embodiments. The patient camera 1422 may capture images or video of the patients face during a motion capture procedure. The images or videos may be processed to identify the locations of the patient's pupils, which then may be used to determine a horizontal axis with respect to the patient's pupils.

In this example, the screen 1438a is oriented parallel to the screen 1438b. In some embodiments. The imaging system 1432 may also include a screen framework (not shown) that positions the screens 1438 with respect to each other. For example, the screen framework may extend beneath the reference structure 1430 and couple to the bottoms of the screens 1438. Together, the screens 1438 and the screen framework are an example of the screen assembly 112. The cameras 1420 are an example of the optical sensing assembly 110.

The screens 1438 may be formed from a translucent material so that the points where the light beams emitted by the light source assembly 1442 intersect with the screens 1438 may be viewed from outside of the screens 1438. Images that include these points of intersection may be recorded by the cameras 1420. The motion determining device 106 may then analyze these captured images to determine the points of intersection of the light beams with the screens 1438 to determine the location of the light source assembly 1442. The position of the light source assembly of a clutch (not shown) may be determined in a similar manner.

The cameras 1420 are positioned and oriented to capture images of the screens 1438. For example, the camera 1420*a* is positioned and oriented to capture images of the screen 438*a*, and the camera 1420*b* is positioned and oriented to capture images of the screen 1438*b*. In some embodiments, the cameras 1420 are mounted to the screen framework so that they are position and orientation of the cameras 1420 are fixed with respect to the screens. For example, each of the cameras 1420 may be coupled to the screen framework by a camera mounting assembly such as is shown in FIG. 10. In this manner, the position and orientation of the cameras 1420 relative to the screens 1438 does not change if the screen framework is moved. In some implementations, the screen framework includes a housing (e.g., as shown at 1110 in FIG. 22), within which the cameras 1420 are disposed.

Figure 24:
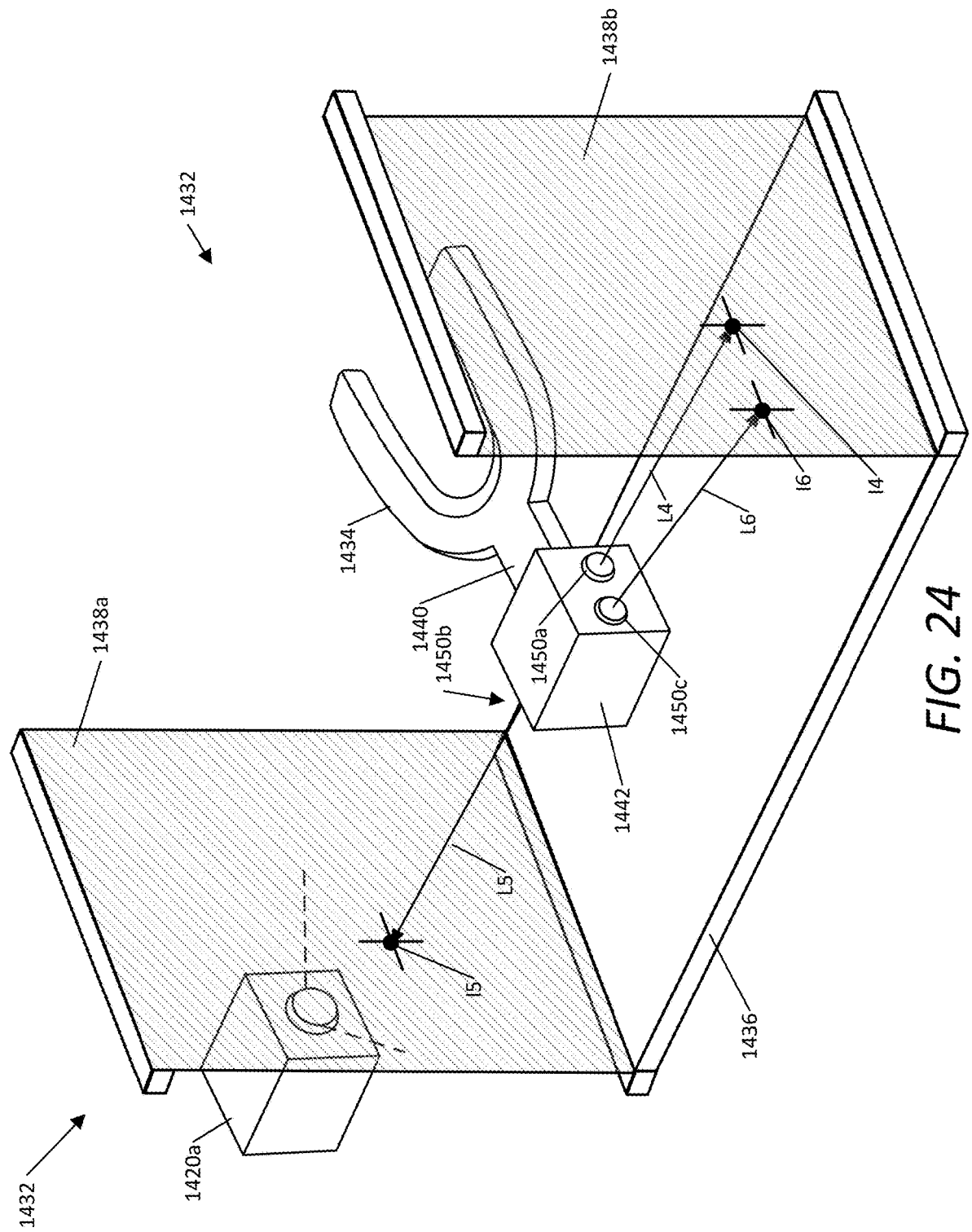
FIG. 24 illustrates a perspective view of the reference structure of FIG. 22 disposed between the screens of the imaging system of FIG. 22.

FIG. 24 illustrates a perspective view of the reference structure 1430 disposed between the screens 1438 of the imaging system 1432. The screens 1438 are joined together by a screen framework 1436 that positions and orients the screens 1438 with respect to one another. In this example, the light emitter 1450*a* is emitting a light beam L4, which intersects with the screen 1438*b* at intersection point I4; the light emitter 1450*b* is emitting a light beam L5, which intersects with the screen 1438*a* at intersection point I5; and the light emitter 1450*c* is emitting a light beam L6, which intersects with the screen 1438*a* at intersection point I6. As the position and orientation of the reference structure 1430 change relative to the screens 1438, the locations of at least some of the intersection points I4, I5, and I6 will change as well.

The camera 1420*a* captures images of the screen 1438*a*, including the intersection point I5 of the light beam L5 emitted by the light emitter 1450*b*. The camera 1420*a* may capture a video stream of these images. Similarly, although not shown in this illustration, the cameras 1420*b* captures images of the screens 1438*b* and the intersection points I4 and I6.

The captured images from the cameras 1420 are then transmitted to the motion determining device 106. The motion determining device 106 may determine the location of the intersection points I4, I5, and I6, and from those points the location of the light source assembly 1442. In some embodiments, a point of common intersection for the light beams L4, L5, and L6 is determined based on the location of the intersection points I4, I5, and I6 (e.g., the point at which the light beams intersect or would intersect if extended). Based on the determined locations of the light beams, the location and orientation of the reference structure 1430 relative to the screens 1438 can be determined.

Figures 25A, 25B:
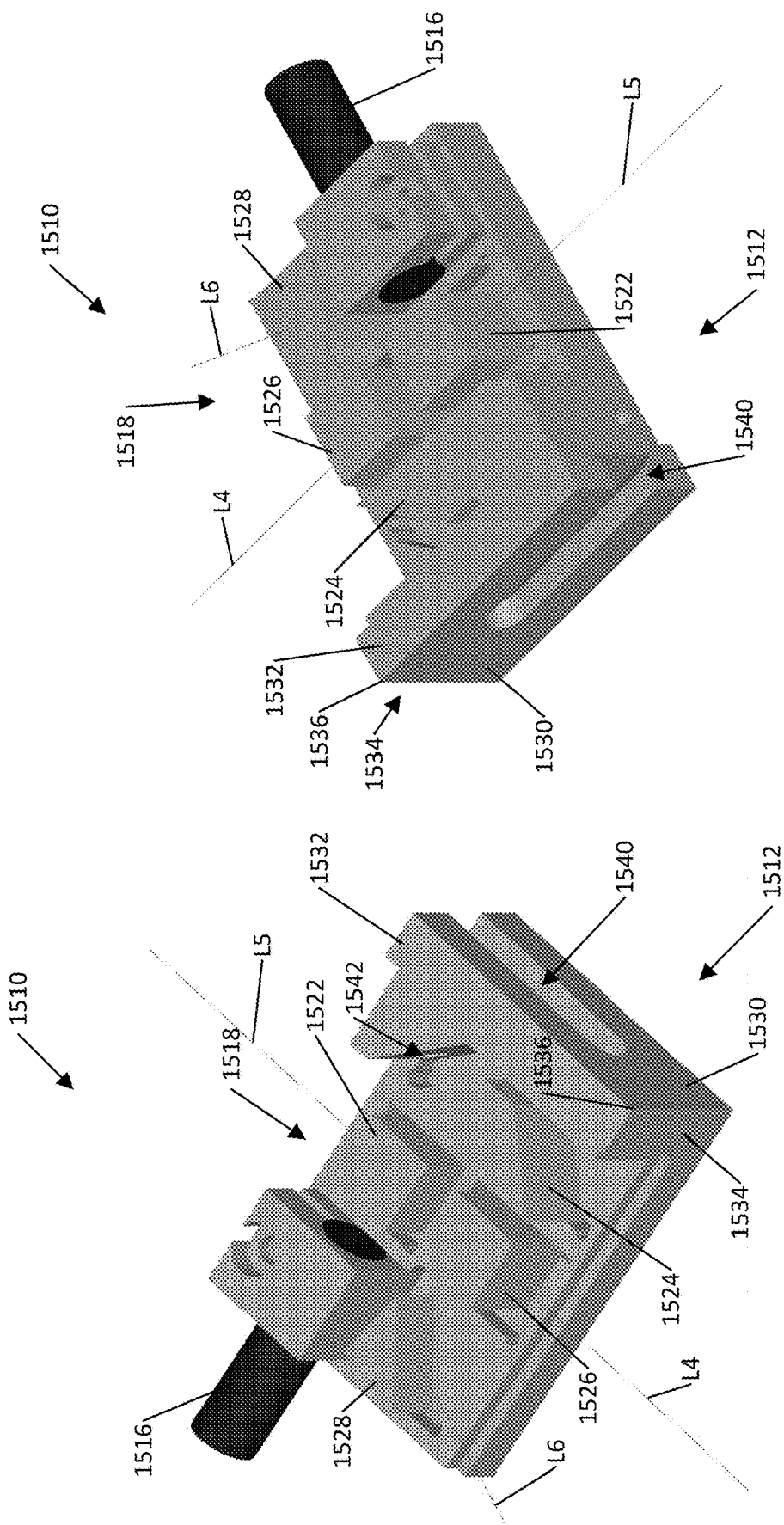
FIGS. 25A and 25B are schematic diagrams of an orthographic projection of an embodiment of a light source assembly that uses a single laser source, which can be used to implement the clutch or reference structure of FIG. 22.

FIGS. 25A and 25B are schematic diagrams of an orthographic projection of an embodiment of a light source assembly 1510 that uses a single laser source. In FIG. 25B the light source assembly 1510 is rotated by 90 degrees with respect to its orientation in FIG. 25A. The light source assembly 1510 may be similar to previously described light source assemblies such as the light source assembly 404. The light source assembly 1510 emits three laser beams L4, L5, and L6 from a single laser emitter 1516.

The light source assembly 1510 includes a framework 1512, the laser emitter 1516, and a beam splitter assembly 1518. In some implementations, the light source assembly 1510 may also include a housing that joins to a portion of the framework 1512 to enclose components of the beam splitter assembly 1518. In embodiments that include the housing, the housing may be similar to previously described housings such as the housing 512.

In some implementations, the light source assembly 1510 also includes one or more fiducial indicators that can be used to visually establish a relationship between the light source assembly 1510 and the patient's dentition. In this example, the light source assembly includes surfaces 1530, 1532, and 1534 that meet at a corner 1536 to establish a relationship between the light source assembly 1510 and the patient's dentition. The surfaces 1530, 1532, and 1534, and the corner 1536 are examples of fiducial indicators.

In the example of FIGS. 25A and 25B, the light source assembly 1510 includes a single laser emitter 1516. Although alternatives are possible, the laser emitter 1516 may be a semiconductor laser emitter such as a laser diode emitter or a solid-state laser emitter such as diode-pumped solid-state laser emitter. The laser emitter 1516 emits a beam of collimated light into the beam splitter assembly 1518.

The beam splitter assembly splits the laser beam emitted by the laser emitter 1516 into three separate light beams L4, L5, and L6. In some embodiments, the beam splitter assembly 1518 contains two reflectors 1524 and 1528 and two beam splitters 1522 and 1526. Examples of the reflectors 1524 and 1528 include prisms and flat mirrors. Examples of the beam splitters 1522 and 1526 include cube beam splitters and plate beam splitters (e.g., cylindrical or circular plate beam splitters), both of which may be formed with one or more prisms.

In this example, the collimated light from the laser emitter 1516 is initially emitted as a horizontal light beam into the first beam splitter 1522, where the first beam splitter 1522 splits the horizontal light beam into two light beams the are substantially orthogonal to one another. One of the light beams is emitted out from the light source assembly 1510 as the light beam L5, while the other light beam continues in a direction that is the same as or similar to the direction of the horizontal light beam.

The horizontal light beam continues on into the first reflector 1524, which includes two reflective surfaces that are arranged to reverse the direction of and offset the horizontal light beam so that it is directed in a parallel but opposite direction. The reflected horizontal light beam then enters the second beam splitter 1526. The second beam splitter 1526 splits the light beam into two light beams the are substantially orthogonal to one another. One of the light beams is emitted out from the light source assembly 1510 as the light beam L4, while the other light beam continues in a direction that is the same as or similar to the direction of the light beam that entered the second beam splitter 1526. In some implementations, the first beam splitter 1522, the first reflector 1524, and the second beam splitter 1526 are arranged within the framework 1512 so as to cause the light beam L5 and the light beam L4 to be collinear.

The light beam then continues to the second reflector 1528. The second reflector 1528 includes a reflective surface that is oriented to reflect the light beam by ninety degrees plus or minus an offset angle. For example, the offset angle may be in the range of approximately 5 degrees to 45 degrees. The reflected light beam is emitted out of the light source assembly 1510 as the light beam L6. The light beam L6 will be directed in a direction that is offset from the direction of the light beam L6 by the offset angle.

In some implementations, the light source assembly 1510 also includes an attachment assembly 1540. The attachment assembly 1540 may be configured to couple to a clutch or reference structure via, for example, an extension member that is sized and oriented to protrude out through a patient's mouth when the patient is wearing the clutch or reference structure. The attachment assembly may include a slot in which the extension member may slide. The slot may have a dove-tailed profile or another profile that is configured to couple to a corresponding profile on a portion of the extension member. The profile may, for example, ensure that light source assembly 1510 attaches to the extension member in a specific orientation. Additionally, the attachment assembly may include a detent structure 1542 that is arranged to lock (or at least impede movement of) the light source assembly 1510 in a specific position with respect to the extension member. Here, the detent structure 1542 includes an aperture through which a spring-loaded pin (not shown) may extend. While the extension member is sliding into the slot, the spring-loaded pin may be depressed into the aperture. Once the extension member is fully slid into the position, the spring-loaded pin may be free to fully extend through the aperture and into the slot, blocking or impeding movement of the extension member in the slot.

In some implementations, the slot 1540 and detent structure 1542 may be disposed in a different location on the light source assembly 1510. For example, the opening of the slot 1540 may be on or near the surface 1534. The detent structure 1542 may be on this side too. This arrangement may allow for better access to the spring-loaded pin as the detent structure 1542 will be further from the laser emitter 1516 and its supporting structure.

Although not shown in FIGS. 25A and 25B, some implementations of the light source assembly 1510 also include a power source such as a battery that provides power for the laser emitter 1516. Some implementations include a cord that provides power from an external source.

Figure 26:
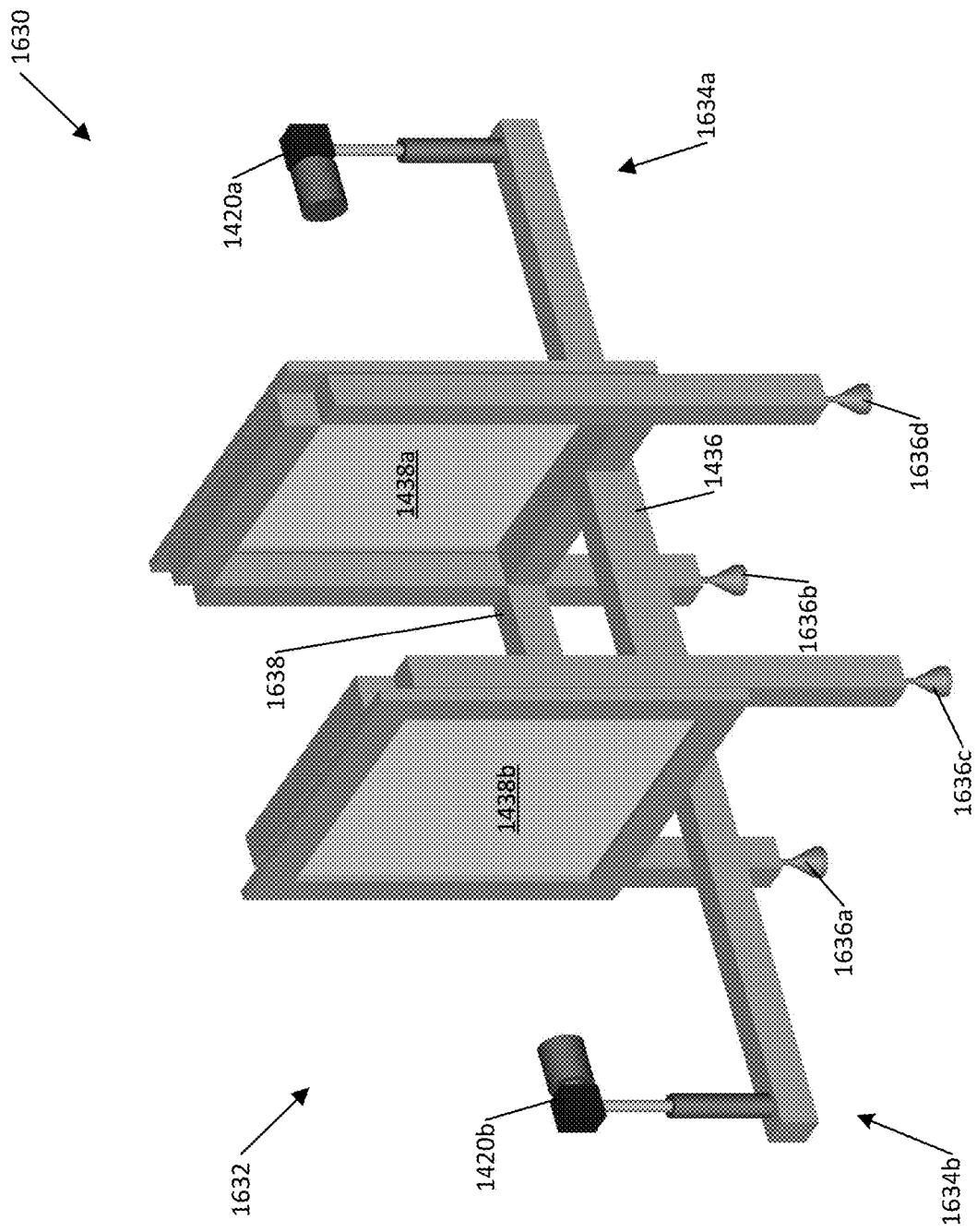
FIG. 26 illustrates an embodiment of an imaging system usable with the system of FIG. 22.

FIG. 26 illustrates an embodiment of an imaging system 1630. The imaging system 1630 is another example of the imaging system 102.

This example embodiment of the imaging system 1630 includes the cameras 1420a and 1420b, a stand 1632, and camera mounting assemblies 1634a and 1634b (referred to collectively as camera mounting assemblies 1634). The imaging system 1630 also includes the screen framework 1436, and the screens 1438a and 1438b.

The stand 1632 is a structure that positions the imaging system for use in capturing movement of a clutch and reference structure mounted to the patient's mouth. The stand 1632 includes legs 1636a, 1636b, 1636c, 1636d (referred to collectively as legs 1636) and mounting framework 1638.

The legs 1636 vertically position the mounting framework 1638. Some embodiments of the stand 1632 are designed to be placed on the floor and the legs 1636 have a longer length. Other embodiments of the stand 1632 are designed to be placed on an elevated surface such as a countertop or table top and the legs 1636 have a shorter length. The length of the legs 1636 may be fixed or adjustable.

The mounting framework 1638 is a structure that other components of the imaging system 1630 are mounted to. In some embodiments, the mounting framework 1638 comprises a plurality of horizontally oriented elongate members. In other embodiments, the mounting framework 1638 may include a surface as well. As shown in FIG. 26, the camera mounting assemblies 1634 and the screen framework 1436 are mounted to the mounting framework 1638.

The camera mounting assemblies 1634 are assemblies that position and orient the cameras 1420 relative to the screens 1438. The camera mounting assemblies 1634 may include various components to adjust the position and orientation of the cameras 1420. In at least some embodiments, the position of the cameras 1420 on the camera mounting assemblies 1634 is selected so that the fields of view of the cameras 1420 approximately coincide with the screens 1438. Alternatively, the fields of view of the cameras 420 may approximately coincide with portions of the screen in which the lights emitted by a clutch or reference structure would be likely to intersect.

The camera mounting assemblies 1634 may be similar to the camera mounting assemblies 534 that are illustrated and described in more detail with respect to at least FIG. 10.

In some implementations, the imaging system 1630 may include a housing that surrounds the cameras and at least one side of the screens (e.g., as shown in FIG. 22).

Figure 27:
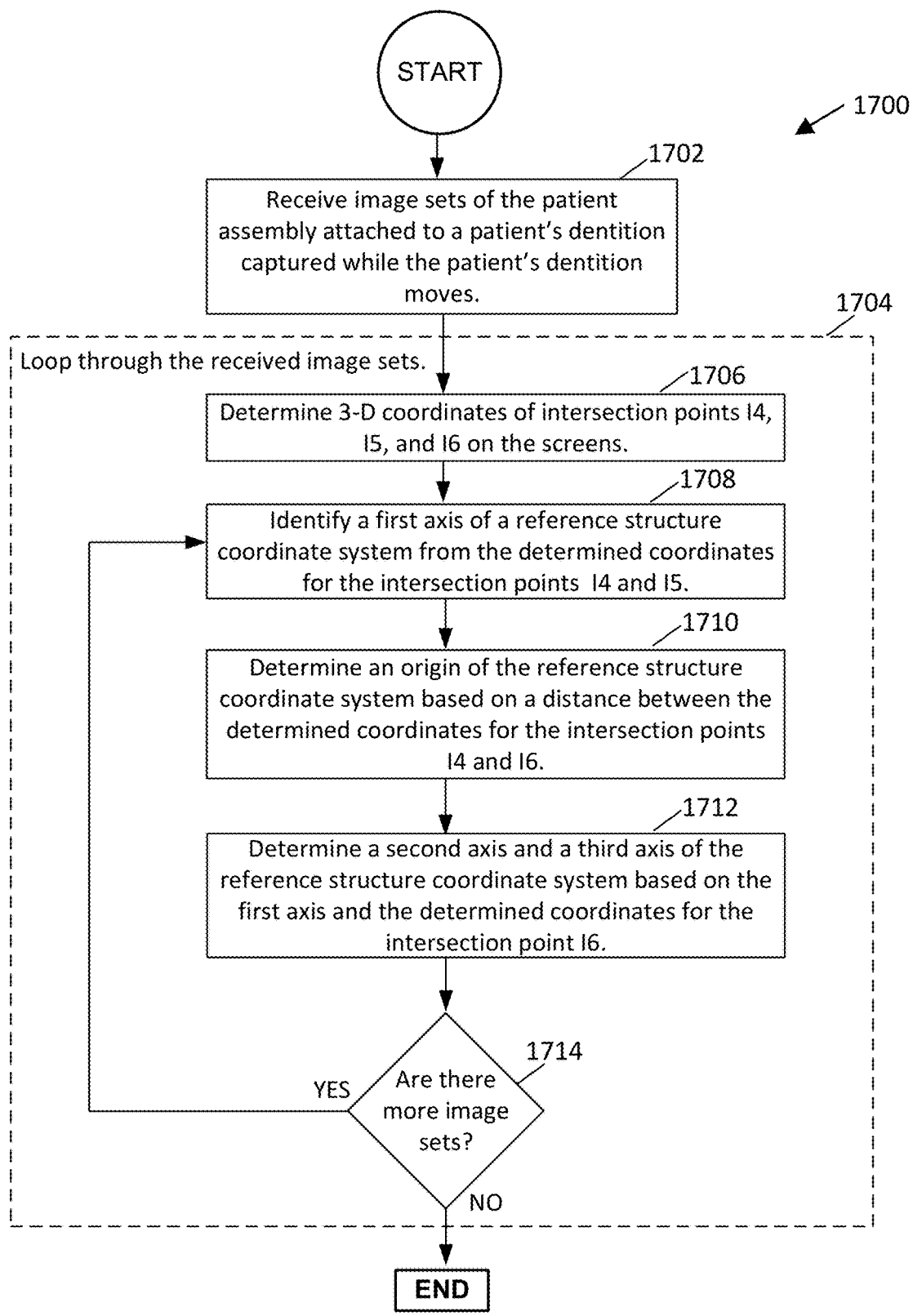
FIG. 27 is an example process for determining a position and orientation of a reference structure attached to a patient's dentition based on images captured by embodiments of the imaging system of FIG. 22.

FIG. 27 is an example process 1700 for determining a position and orientation of a reference structure attached to a patient's dentition based on images captured by an imaging system having two screens, such as the imaging system 1102.

In some embodiments, the process 1700 is performed by the motion determining device 106 while determining the relative motion of the patient's upper and lower dentition with respect to each other. Although the process 1700 is described with respect to a reference structure, a similar process may be performed to determine the position and orientation of a clutch from images captured by the imaging system. In at least some implementations, the same images are used to determine the positions and orientations of both the clutch and the reference structure. Based on the determined positions and orientations, the relative motions of the clutch and the reference structure may be determined and the location of the condyle hinge axis may be inferred.

At operation 1702, image sets of the patient assembly attached to a patient's dentition captured while the patient's dentition moves are received. The operation 1702 may be similar to the previously described operation 902.

At operation 1704, a loop processes each of the received image sets. Within this description of the loop of operation 1704, the received image set that is being processed is referred to as the current image set.

At operation 1706, the three-dimensional coordinates of the intersection points I4, I5, and I6 are determined by processing the images in the current image set. For example, each image in the current image set may capture a different screen of the imaging system. For example, in an implementation with two screens, the current image set may include two images. The intersection points I4, I5, and I6 within the images where light projected by the patient assembly 104 intersects the screens may be determined based, for example, on color, intensity, or contrast values.

Each image may include at least one of the intersection points I4, I5, and I6. In some implementations, the images will also include at least one of intersection points I1, I2, and I3 generated by light emitted by a clutch opposite the reference structure. For example, a single image of a first screen may include an intersection point from the clutch and two intersection points from the reference structure. Another image of a second screen may include two intersection points from the clutch and one intersection point from the reference structure. In some embodiments, a color of the intersection point is analyzed to determine whether the light beam was emitted by a light emitter of the clutch or reference structure. Additionally, the position of the intersection point may be used to distinguish between intersection points from light emitters on the clutch and intersection points on the reference structure. Similarly, positions of the intersection points may be used to distinguish between intersection points from different light emitters of the same clutch or reference structure.

The three-dimensional coordinates may be determined with respect to a coordinate space associated with the imaging system 102. In some implementations, at least some of the pixels of the captured images are mapped to a three-dimensional coordinate within the coordinate space associated with the imaging system 102. This mapping may be determined during an initial calibration process (e.g., as described with respect to at least FIG. 19).

At operation 1708, a first axis of a coordinate system associated with the reference structure is identified based on the intersection points I4 and I5. As described elsewhere, the intersection points I4 and I5 are generated by light beams that are substantially collinear but oriented in opposite directions. Accordingly, the intersection points I4 and I5 will be with screens on opposites of the patient. A first axis of the reference structure can be determined based on identifying a line extending through the intersection points I4 and I5. This first axis will roughly correspond to the lateral axis (or side-to-side axis) for the patient's dentition.

At operation 1710, an origin of the reference structure coordinate system based on a distance between the determined coordinates for the intersection points I4 and I6. As described elsewhere, the intersection points I4 and I6 are generated by light beams that are directed toward the same screen but are separated by an offset angle. Based on the distance between the intersection points I4 and I5 and the offset angle, a distance to the light emitter of the reference structure can be determined (e.g., a distance from the light emitter of the reference structure to the intersection point I4 can be found heuristically, using a binary search, or based on trigonometric relationships of the offset angle (which is known) and the distance between points I4 and I5). The origin of the reference structure coordinate system can then be identified along the first axis using the determined distance from the point I4. This origin of the reference structure coordinate system will be at a fixed position with respect to the patient's dentition.

At operation 1712, a second axis and a third axis of the reference structure coordinate system can then be determined based on the first axis and the determined coordinated for the intersection point I6. The three intersection points I4, I5, and I6 define a plane. There are various ways to define the axes of the coordinate system of that plane. For example, a second axis of the coordinate system may be identified based on the cross-product of the first axis and a vector between the determined coordinates of the intersection point I6 and any point along the first axis (e.g., the origin or the determined coordinates of either of the intersection points I4 and I5. In this case, the second axis will be normal to the plane defined by the three intersection points I4, I5, and I6. This second axis will roughly correspond to the vertical axis of the patient's dentition. A third axis can then be identified based on the cross-product of the first axis and the second axis. This third axis will roughly correspond to the anterior-to-posterior (or front-to-back) dimension for the patient's dentition.

At operation 1714, it is determined whether there are more image sets to process through the loop. If so, the process 1700 returns to operation 1706 to process the next image set. If not, the process ends.

Figure 28:
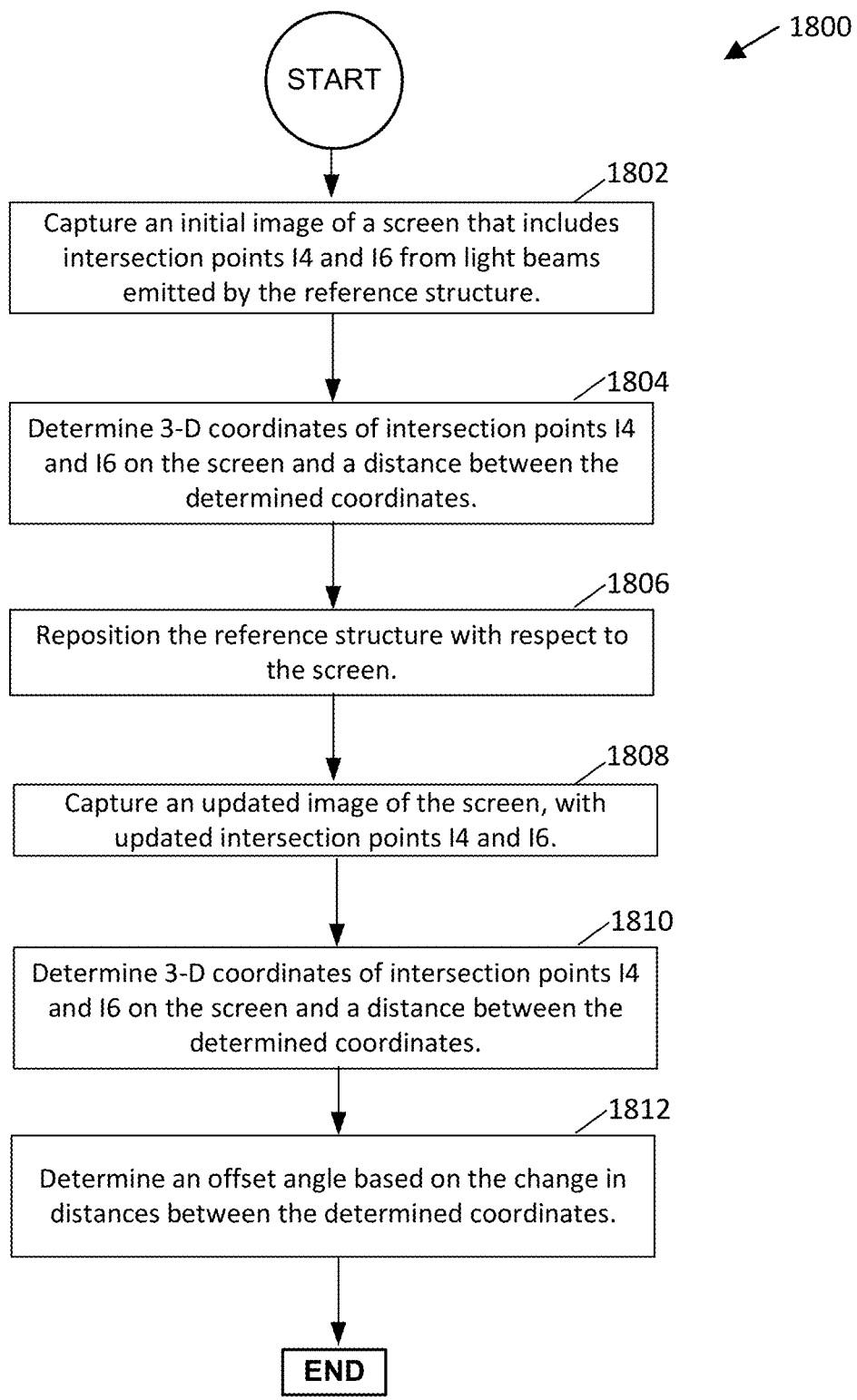
FIG. 28 is an example process for determining the offset angle of a reference structure using images captured with embodiments of the imaging system of FIG. 22.

FIG. 28 is an example process 1800 for determining the offset angle of a reference structure, such as the reference structure 1122, using images captured with an imaging system, such as the imaging system 1102. In some implementations, the offset angle is determined during an initial calibration process for the reference structure. The determined offset angle may then be stored in a data store, where the offset angle can be retrieved for use in determining the position and orientation of the reference structure (e.g., as described in the process 1700). Although the process 1800 is described with respect to a reference structure, a similar process may be performed to determine an offset angle for a clutch using images captured by the imaging system. In some embodiments, the process 1800 is performed by the motion determining device 106.

At operation 1802, an initial image of a screen that includes intersection points I4 and I6 from light beams emitted by the reference structure is captured. The reference structure may be positioned at or approximately at a known distance from the screen. In some implementations, the reference structure may be positioned using a linear slide. The linear slide may be orientated to position the reference structure along an axis that is normal or approximately normal to the plane of the screen.

At operation 1804, three-dimensional coordinates of intersection points I4 and I6 on the screen are determined and an initial distance between the determined coordinates is determined. The three-dimensional coordinates may be determined in a manner similar to that described previously with respect to the operation 1706 of the process 1700 illustrated in FIG. 27.

At operation 1806, the reference structure is repositioned with respect to the screen. For example, the reference structure may be moved a fixed distance along a linear slide.

At operation 1808, an updated image of the screen that includes updated intersection points I4 and I6 is captured.

At operation 1810, three-dimensional coordinates of the updated intersection points I4 and I6 on the screen are determined and an updated distance between the determined coordinates is calculated. The operation 1810 may be performed in a manner similar to the operation 1804.

At operation 1812, an offset angle for the reference structure is determined based on the change in distances between the determined coordinates. For example, a trigonometry function can be used to determine the offset angle based on the ratio of the change in distances between the initial intersection points and the updated intersection points and the distance the reference structure was moved. As described previously, the offset angle can then be stored for later use in determining the position and orientation of the reference structure from images of the intersection points.

Figure 29:
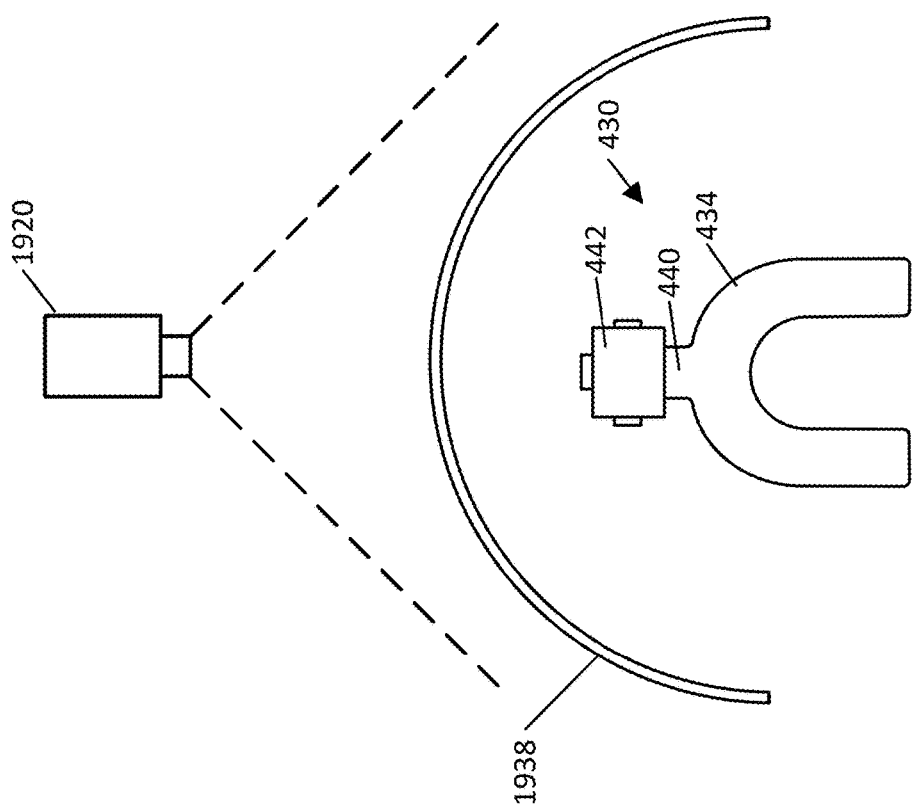
FIG. 29 illustrates a top view of another embodiment the imaging system of FIG. 1.

FIG. 29 illustrates a top view of an embodiment an imaging system 1932. The imaging system 1432 is an example of the imaging system 1102.

The imaging system 1932 includes the reference structure 430, screen 1938, and a camera 1920. In this example, the screen 1938 is curved. Although alternatives are possible, the screen has a semi-cylindrical shape in the embodiment shown. The imaging system 1932 may also include a screen framework (not shown) that positions the screen with respect to the camera 1920. Together, the screens 1938 and the screen framework (if any) are an example of the screen assembly 112. The camera 1920 is an example of the optical sensing assembly 110.

In this example, the camera 1920 is positioned at the mid-point of the screen 1938 and offset in a direction normal to the surface of the screen 1938. From this position, with a sufficiently wide-angle lens, the camera 1920 can capture images that include all or nearly all of the screen 1938. An initial calibration process may be used to map pixels of the images captured by the camera 1920 to positions on the screen 1938. Some implementations include multiple cameras that are positioned at various points with respect to the arc of the screen 1938.

3D Platform

Implementations described herein may use a 3D Platform to develop a variety of 3D applications able to run natively on popular operating systems (e.g., Microsoft Windows, Apple OS-X, etc.). The software may be written in any language such as object-oriented C++ and may use industry standard Qt and OpenGL libraries to provide user interface widgets (menus, icons, etc.) and 3D interactive graphics, respectively.

This 3D platform may be used to provide a 3D motion capture user interface for the motion mapping technology device. This same 3D platform may also be used to provide 3D data processing applications geared toward specific dental needs such as:

Treatment planning;
Crown and bridge design;
Digital setups (orthodontic simulations) for aligners and indirect bonding;
Implant location planning for implant supported dentures; and
Splints for oral surgery and TMJ disorder treatment.

The 3D platform may include a rich set of core library tools that operate on some or all of the following types of data:

Polylines—ordered sets of 3D points;
Splines—smooth 3D curves;
Meshes—networks of interconnected 3D triangles;
Planes—3D planes;
Datums—3D locations/coordinate systems;
Dimensions—3D distance and angle annotation; and
Notes—Used to document important features on a 3D model.

The 3D platform may include tools to provide functions to do one or more of the following: copy, move, rotate, translate, scale, trim, merge, intersect, offset, smooth, and filter. Many other tools may also be provided.

Implementations of the 3D platform may also include other library tools to allow the application developer to:

Capture and record live video data from digital cameras;
Correct 3D opto-mechanical errors via calibration;
Generate formatted reports;
Read and write all 3D data in an efficient, proprietary or non-proprietary binary file format;
Read and write 3D mesh data using open standard STL files; and
Generate files used to 3D print or CNC mill physical objects.

Implementations may also include higher level tools that are specifically tailored to dental applications. For instance, instead of manipulating a mesh, spline or plane, the application developer can more naturally manipulate a "tooth", "arch wire", or "occlusal plane". These higher-level tools may include features to:

Segment/isolate teeth from a full arch model;
Reposition teeth to simulate orthodontic or surgical treatment;
Place orthodontic brackets on teeth;
Reshape teeth to simulate restorative dental work; and
Measure anatomical features and report critical distances/angles/ratios.

Having a "core" foundation upon which the motion mapping technology dental applications are built provides tremendous flexibility to provide "specialist modules" that target specific types of dental applications (restorative, orthodontics, oral surgery, etc.) or even applications outside of dentistry (orthopedics, product engineering/testing, animation, etc.) with relative ease.

Case Portal

Some implementations include a case portal system that provides a means for clinicians and laboratories to:

Share patient records (motion data, 3D models, photos, x-rays, treatment plans, etc.) via the internet in a Health Insurance Portability and Accountability Act (HIPAA) compliant manner;
Limit access to records based on client-defined group permission policies; and
Manage case work via a messaging system that provides automated notifications/reminders.

Implementations of the case portal system may provide a web interface that has sheets (tabs) for each type of record (3D models, x-rays, photos, etc.) taken on a patient. Within each sheet stacks may be used to further organize records chronologically. For instance, the "Photos" sheet might contain an "Anterior" stack that includes anterior photos taken of a patient at different points in time.

Since patient record files can be very large, they may be stored on a local server in the clinic that is then synched periodically with a cloud server. This provides rapid access to local records and offers the convenience and data security of remote cloud storage.

Although the examples in this disclosure relate primarily to jaw motion tracking, the disclosed technology may be used in other applications too. For example, the light source assembly may be used to evaluate or measure motion of any joints (or moving portions) of human or animal bodies. In some implementations, the light source assembly is rigidly coupled to a body part other than the jaw using an appropriate coupling device. For example, a light source assembly may be coupled to a first side of a joint and a second side of a joint, such as above and below a knee. The light source assembly may be used to precisely identify the location of the hinge axis of a joint. In various implementations, one, two, or more than two light source assemblies may be used to capture motion depending on where motion or flexure is expected.

A dentition coupling device is a non-limiting example of a coupling device. The light source assembly may be used to capture information to, for example, evaluate or improve physiological performance by determining range of motion, laxity, or other properties, of a joint. Some embodiments may use the information captured using the light source assembly for treatment planning, surgical planning, physical therapy, or to design surgical guides. The light source assembly may also be used during surgery to evaluate, track, and guide the position of surgical instruments with respect to a patient's body.

The light source assembly may also be used to accurately capture motion of human or animal, such as horse, bodies to guide the movement of three-dimensional models for computer generated animation or video games.

Embodiments of the technology disclosed herein may also be used in various engineering and industrial applications, such as engineering testing. For example, one or more light source assemblies may be affixed to mechanical components, such as airplane wings, automobile parts, or sports equipment, to evaluate flexure under various conditions. In some implementations, the screen assembly may be formed from walls or other architectural structures of the building or room in which the component being tested is disposed. In at least some of these implementations, the imaging system may be disposed on the same side of the screen assembly as the light source assemblies.

The various embodiments described above are provided by way of illustration only and should not be construed to limit the claims attached hereto. Those skilled in the art will readily recognize various modifications and changes that may be made without following the example embodiments and applications illustrated and described herein, and without departing from the true spirit and scope of the following claims.

Some non-limiting examples are provided below:

Example 1

An apparatus comprising: a screen; an imaging system configured to capture an image of the screen; and a position indicating system that includes: a housing; a first light emitter disposed within the housing and oriented to emit light in a first direction toward the screen; a second light emitter disposed within the housing and oriented to emit light in a second direction, the second direction being collinear with and opposite to the first direction; and a third light emitter disposed within the housing and oriented to emit light in a third direction, the third direction being different than the first direction and the second direction; wherein the screen is disposed between the position indicating system and the imaging system.

Example 2

The apparatus of example 1, wherein the third light emitter is positioned so that a line corresponding to the third direction intersects with a line corresponding to the first direction.

Example 3

The apparatus of example 2, wherein the third light emitter is oriented so that the third direction is perpendicular to the first direction.

Example 4

The apparatus of example 2, wherein the third light emitter is oriented to emit light toward the screen.

Example 5

The apparatus of example 4, wherein the third light emitter is oriented so that the third direction is offset from the first direction by an offset angle of less than 90 degrees.

Example 6

The apparatus of example 5, wherein the third light emitter is oriented so that the third direction is offset from the first direction by an offset angle that is an acute angle. In some examples, the offset angle is angle of less than 45 degrees.

Example 7

The apparatus of example 6, wherein the third light emitter is oriented so that the third direction is offset from the first direction by an offset angle of between 5 degrees and 15 degrees.

Example 8

The apparatus of example 6, wherein the third light emitter is oriented so that the third direction is offset from the first direction by an offset angle of less than 10 degrees.

Example 9

The apparatus of example 4, further comprising a motion determining device configured to process the image of the screen to determine motion of the imaging system based on identifying intersection points of light emitted by the first light emitter and light emitted by the third light emitter.

Example 10

The apparatus of example 1, further comprising a reference position indicating system that includes a reference light emitter configured to emit light toward the screen.

Example 11

The apparatus of example 1, wherein the screen is curved and the second light emitter being positioned and oriented to emit light toward the screen.

Example 12

The apparatus of example 11, wherein the screen has a semi-cylindrical shape.

Example 13

An apparatus comprising: a screen assembly including a first planar screen and a second planar screen; an imaging system including a first camera configured to capture images of the first screen and a second camera configured to capture images of the second screen; a position indicating system including: a first light emitter positioned and oriented to emit light in a first direction toward the first screen; a second light emitter positioned and oriented to emit light in a second direction toward the second screen, the second direction being collinear with and opposite to the first direction; and a third light emitter positioned and oriented to emit light in a third direction toward the first screen, the third direction being different than the first direction and the second direction.

Example 14

The apparatus of example 13, wherein the third light emitter is oriented so that the third direction is offset from the first direction by an offset angle of less than 45 degrees.

Example 15

The apparatus of example 13, further comprising a motion determining device configured to: process the first image to determine a first intersection point, the first intersection point corresponding to an intersection of light emitted by the first light emitter with the first planar screen; process the second image to determine a second intersection point, the second intersection point corresponding to an intersection of light emitted by the second light emitter with the second planar screen; process the first image to determine a third intersection point, the third intersection point corresponding to an intersection of light emitted by the third light emitter with the first planar screen; determine a position of the position indicating system relative to the screen assembly based on the first intersection point and the third intersection point; and determine an orientation of the position indicating system relative to the screen assembly based on the first intersection point, the second intersection point, and the third intersection point.

Example 16

The apparatus of example 15, wherein the motion determining device being configured to determine a position of the position indicating system relative to the screen assembly based on the first intersection point and the third intersection point includes the motion determining device being configured to: determine an identifier for the position indicating system; retrieve an offset angle compensation factor associated with the identifier of the position indicating system; determine a distance between the first intersection point and the third intersection point; and determine a distance from the first planar screen to the position indicating system based on the retrieved offset angle compensation factor and the determined distance between the first intersection point and the third intersection point.

Example 17

An apparatus configured to be worn on a dentition of a patient, the apparatus comprising: a dentition coupling device configured to couple to the dentition of the patient, the dentition coupling device including an extension member configured to protrude out from the patient's mouth; and a position indicating system rigidly connected to the dentition coupling device, the position indicating system including: a housing configured to rigidly connect to the extension member of the dentition coupling device; a first light emitter disposed within the housing and oriented to emit light in a first direction; a second light emitter disposed within the housing and oriented to emit light in a second direction, the second direction being collinear with and opposite to the first direction; and a third light emitter disposed within the housing and oriented to emit light in a third direction, the third direction being different than the first direction and the second direction and offset from the first direction by an offset angle that is an acute angle. In some examples, the offset angle is an angle of less than 45 degrees.

Example 18

The apparatus of example 17, wherein the third light emitter is oriented so that the third direction is offset from the first direction by an offset angle of between 5 degrees and 15 degrees.

Example 19

The apparatus of example 17, wherein the third light emitter is oriented so that the third direction is offset from the first direction by an offset angle of less than 10 degrees.

Example 20

The apparatus of example 17, wherein: the third light emitter is positioned so that a line corresponding to the third direction intersects with a line corresponding to the first direction; the housing includes at least three planar surfaces that meet in a corner; and the position indicating system is associated with a compensation factor that relates the position of the corner with the position of the intersection of the line corresponding to the third direction with the line corresponding to the first direction.

Example 21

The apparatus of any of examples 1-20, wherein the first light emitter, the second light emitter, and the third light emitter emit substantially collimated light.

Example 22

The apparatus of example 21, wherein the first light emitter, the second light emitter, and the third light emitter emit laser beams.

Example 23

The apparatus of example 22, wherein the first light emitter includes a first laser diode, the second light emitter includes a second laser diode, and the third light emitter includes a third laser diode. Example 24: The apparatus of example 21, wherein the first light emitter is a first aperture of a beam splitter assembly, the second light emitter is a second aperture of the beam splitter assembly, and the third light emitter is a third aperture of the beam splitter assembly.

Example 25

A method comprising: capturing a first image of a first screen of a screen assembly; capturing a second image of a second screen of the screen assembly; identifying in the first image a first intersection point, the first intersection point corresponding to an intersection of light emitted by a first light emitter of a position indicating system with the first screen; identifying in the second image a second intersection point, the second intersection point corresponding to an intersection of light emitted by a second light emitter of the position indicating system with the second screen; identifying in the first image a third intersection point, the third intersection point corresponding to an intersection of light emitted by a third light emitter of the position indicating system with the first screen; and determining a position and orientation of the position indicating system relative to the screen assembly based on the first intersection point, the second intersection point, and the third intersection point.

Example 26

The method of example 25, wherein the determining a position and orientation of the position indicating system relative to the screen assembly includes: determining a position of the position indicating system relative to the screen assembly based on the first intersection point and the third intersection point; and determining an orientation of the position indicating system relative to the screen assembly based on the first intersection point, the second intersection point, and the third intersection point.

Example 27

The method of example 25, further comprising: determining a three-dimensional coordinate of the first intersection point with respect to the screen assembly; determining a three-dimensional coordinate of the second intersection point with respect to the screen assembly; and determining a three-dimensional coordinate of the third intersection point with respect to the screen assembly.

What is claimed is:

1. An apparatus comprising:
a screen;
an imaging system configured to capture an image of the screen; and
a position indicating system that includes:
a housing;
a first light emitter disposed within the housing and oriented to emit light in a first direction toward the screen;
a second light emitter disposed within the housing and oriented to emit light in a second direction, the second direction being collinear with and opposite to the first direction; and
a third light emitter disposed within the housing and oriented to emit light in a third direction, the third direction being different than the first direction and the second direction;
wherein the screen is disposed between the position indicating system and the imaging system.

2. The apparatus of claim 1, wherein the third light emitter is positioned so that a line corresponding to the third direction intersects with a line corresponding to the first direction.

3. The apparatus of claim 2, wherein the third light emitter is oriented so that the third direction is perpendicular to the first direction.

4. The apparatus of claim 2, wherein the third light emitter is oriented to emit light toward the screen.

5. The apparatus of claim 4, wherein the third light emitter is oriented so that the third direction is offset from the first direction by an offset angle of less than 90 degrees.

6. The apparatus of claim 5, wherein the third light emitter is oriented so that the third direction is offset from the first direction by an offset angle of less than 45 degrees.

7. The apparatus of claim 6, wherein the third light emitter is oriented so that the third direction is offset from the first direction by an offset angle of between 5 degrees and 15 degrees.

8. The apparatus of claim 6, wherein the third light emitter is oriented so that the third direction is offset from the first direction by an offset angle of less than 10 degrees.

9. The apparatus of claim 4, further comprising a motion determining device configured to process the image of the screen to determine motion of the imaging system based on identifying intersection points of light emitted by the first light emitter and light emitted by the third light emitter.

10. The apparatus of claim 1, further comprising a reference position indicating system that includes a reference light emitter configured to emit light toward the screen.

11. The apparatus of claim 1, wherein the screen is curved and the second light emitter being positioned and oriented to emit light toward the screen.

12. The apparatus of claim 11, wherein the screen has a semi-cylindrical shape.

13. An apparatus comprising:
a screen assembly including a first planar screen and a second planar screen;
an imaging system including a first camera configured to capture images of the first planar screen and a second camera configured to capture images of the second planar screen;
a position indicating system including:
a first light emitter positioned and oriented to emit light in a first direction toward the first planar screen;
a second light emitter positioned and oriented to emit light in a second direction toward the second planar screen, the second direction being collinear with and opposite to the first direction; and
a third light emitter positioned and oriented to emit light in a third direction toward the first planar screen, the third direction being different than the first direction and the second direction.

14. The apparatus of claim 13, wherein the third light emitter is oriented so that the third direction is offset from the first direction by an offset angle of less than 45 degrees.

15. The apparatus of claim 13, further comprising a motion determining device configured to:
process a first image to determine a first intersection point, the first intersection point corresponding to an intersection of light emitted by the first light emitter with the first planar screen;
process a second image to determine a second intersection point, the second intersection point corresponding to an intersection of light emitted by the second light emitter with the second planar screen;
process the first image to determine a third intersection point, the third intersection point corresponding to an intersection of light emitted by the third light emitter with the first planar screen;
determine a position of the position indicating system relative to the screen assembly based on the first intersection point and the third intersection point; and
determine an orientation of the position indicating system relative to the screen assembly based on the first intersection point, the second intersection point, and the third intersection point.

16. The apparatus of claim 15, wherein the motion determining device being configured to determine a position of the position indicating system relative to the screen assembly based on the first intersection point and the third intersection point includes the motion determining device being configured to:
determine an identifier for the position indicating system;
retrieve an offset angle compensation factor associated with the identifier of the position indicating system;
determine a distance between the first intersection point and the third intersection point; and
determine a distance from the first planar screen to the position indicating system based on the retrieved offset angle compensation factor and the determined distance between the first intersection point and the third intersection point.

* * * * *